(12) United States Patent
Iglesias et al.

(10) Patent No.: US 7,723,068 B2
(45) Date of Patent: May 25, 2010

(54) GENE CLUSTER INVOLVED IN SAFRACIN BIOSYNTHESIS AND ITS USES FOR GENETIC ENGINEERING

(75) Inventors: Ana Velasco Iglesias, Madrid (ES); Fernando de la Calle, Madrid (ES); Tomás Aparicio Pérez, Madrid (ES); Carmen Schleissner Sánchez, Madrid (ES); Paloma Acebo Páis, Madrid (ES); Pilar Rodríguez Ramos, Madrid (ES); Fernando Reyes Benítez, Madrid (ES); Rubén Henríquez Peláez, Madrid (ES)

(73) Assignee: PharmaMar, S.A., Madrid (ES)

( * ) Notice: Subject to any disclaimer, the term of this patent is extended or adjusted under 35 U.S.C. 154(b) by 15 days.

(21) Appl. No.: 10/540,092

(22) PCT Filed: Dec. 19, 2003

(86) PCT No.: PCT/GB03/05563

§ 371 (c)(1),
(2), (4) Date: Sep. 22, 2005

(87) PCT Pub. No.: WO2004/056998

PCT Pub. Date: Jul. 8, 2004

(65) Prior Publication Data

US 2006/0134764 A1 Jun. 22, 2006
US 2008/0182302 A2 Jul. 31, 2008

(30) Foreign Application Priority Data

Dec. 20, 2002 (GB) .................................. 0229793.5

(51) Int. Cl.
*C12P 21/06* (2006.01)

(52) U.S. Cl. ...................... 435/69.1; 435/6; 435/320.1; 536/23.1

(58) Field of Classification Search ...................... None
See application file for complete search history.

(56) References Cited

U.S. PATENT DOCUMENTS 6,551,795 B1 * 4/2003 Rubenfield et al. ......... 435/69.1

FOREIGN PATENT DOCUMENTS

EP 055299 A1 7/1982
WO WO 0069862 11/2000

OTHER PUBLICATIONS

Seffernick et al., J. Bacteriology, vol. 183, pp. 2405-2410, 2001.*
Wells, Biochemistry, vol. 29, pp. 8509-8517, 1990.*
Pospiech et al. (Microbiology, vol. 141, pp. 1793-1803, Feb. 18, 1999.*
Andreas Pospiech et al., Two multifunctional peptide synthatases and an O-methyltransferase are involved in the biosynthesis of the DNA-binding antibiotic and antitumour agent saframycin Mx1 from *Myxococcus xanthus*, Microbiology, 142, 741-746, 1996.
Marahiel, M., Protein templates for the biosynthesis of peptide antibiotics, Chemistry and Biology, 4, 561-567, Aug. 1997.
Tang et al., "Engineered Biosynthesis of Regioselectively Modified Aromatic Polyketides Using Bimodular Polyketide Synthases," PLOS Biology, vol. 2, Issue 2, pp. 227-238, Feb. 2004.
Roche Applied Science, "DIG Application Manual for Nonradioactive In Situ Hybridization," 3rd Edition, Chapter 3: Nucleic Acid Hybridization- General Aspects, pp. 33-37, downloaded from internet <<http://www.roche-applied-science.com/PROD_INF/MANUALS/InSitu/pdf/ISH_33-37.pdf>> on Mar. 26, 2008.

* cited by examiner

*Primary Examiner*—Hope A Robinson
(74) *Attorney, Agent, or Firm*—King & Spalding, LLP; Kenneth H. Sonnenfeld; Michael A. Willis

(57) ABSTRACT

A gene cluster is disclosed having open reading frames which encode polypeptides sufficient to direct the synthesis of a safracin molecule. In addition, the present disclosure is directed to a nucleic acid sequence, suitably an isolated nucleic acid sequence, which includes or comprises at least SEQ ID NO:1, variants or portions thereof, or at least one of the sacA, sacB, sacC, sacC, sacD, sacE, sacF, sacG, sacH, sacH, saI, sacJ, orf1, orf2, orf3 or orf4 genes, including variants or portions.

14 Claims, 9 Drawing Sheets

| Core Sequence | 1 LKAGGA | 2 SGTTG | 3 GELCIGG | 4 TGD | 5 RIELGEIE | 6 LGGHS |
|---|---|---|---|---|---|---|
| SafB1 97 | -LYAGVVAVPVYP-78- | YTSGSTADPKG-220- | GEIWVRGPSVAQGY-23- | LRTGDL-23- | NYYPQDLEL-163- | LPDLGLDSLALVELKHRIE- |
| SafB2 1247 | -LEAGGVAVPLDP-64- | YTSGSTGQPKG-172- | GELFIGGAGVARGY-24- | YRTGDL-23- | FRIEFEEIE-121- | FFDLGGNSLLATRLATRLA- |
| SafA1 559 | -LKAGGAYVPLDP-64- | YTSGSSGRPKG-173- | GELFIGGSSGVARGY-24- | YRTGDL-23- | YRIELAEIE-121- | FFELGGNSLLAGRLVEELD- |
| SafA2 1668 | -LKAGGAYVPLDP-67- | YTSGSTGTPKA-179- | GELFVGGVGLARGY-24- | YRTGDL-23- | YRVELGEIE-122- | FFEVGGTSLLLARLASRLL- |
| SacA 483 | -MACGGGSYVPLSD-63- | FTSGSTGEPKG-172- | GELIIHGHGVAQGY-20- | YRTGDR-23- | FRVELGPVQ-121- | FLDIGGHSLSLTHLTGLLR- |
| SacB 524 | -WQVGGIYVPLSK-63- | YTSGSTGKPKG-173- | GELLICGPGVSQGY-22- | YLTGDR-23- | HRIELGEIE-123- | FFQLGGHSILVARMVERIE- |
| SacC 515 | -RAGHAFLPIDPR-62- | YTSGSTGVPKG-178- | GEIMLAGONLARGY-21- | YATGDL-23- | HRIELNEVA-122- | FFEQGGNSILLTRLAGTLS- |
| FUNCTION | unknown | ATP binding | ATP binding | ATPase motif | ATP binding | 4' phosphopantetheine binding |

Figure 2

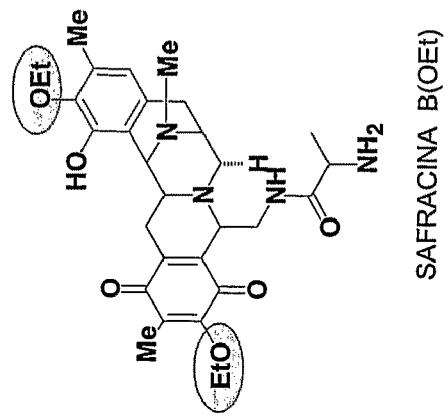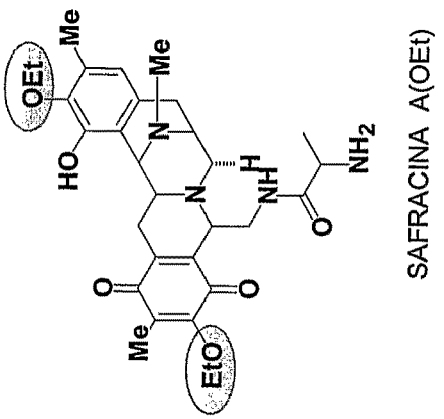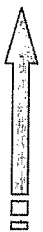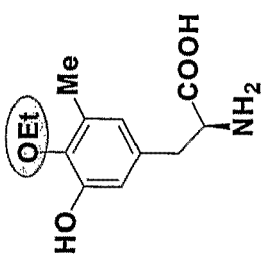
Figure 8

SEQUENCE LISTING

```
<160> NUMBER OF SEQ ID NOS: 35

<210> SEQ ID NO 1
<211> LENGTH: 26705
<212> TYPE: DNA
<213> ORGANISM: Pseudomonas fluorescens A2-2
<220> FEATURE:
<221> NAME/KEY: misc_feature
<222> LOCATION: (6080)..(9268)
<223> OTHER INFORMATION: SacB: non ribosomal peptide synthetase gene
<220> FEATURE:
<221> NAME/KEY: misc_feature
<222> LOCATION: (9275)..(13570)
<223> OTHER INFORMATION: SacC: non ribosomal peptide synthetase gene
<220> FEATURE:
<221> NAME/KEY: misc_feature
<222> LOCATION: (13602)..(14651)
<223> OTHER INFORMATION: SacD: hypothetical protein gene
<220> FEATURE:
<221> NAME/KEY: misc_feature
<222> LOCATION: (14719)..(14901)
<223> OTHER INFORMATION: SacE: hypothetical protein gene
<220> FEATURE:
<221> NAME/KEY: misc_feature
<222> LOCATION: (14962)..(16026)
<223> OTHER INFORMATION: SacF: methyl-transferase protein gene
<220> FEATURE:
<221> NAME/KEY: misc_feature
<222> LOCATION: (16115)..(17155)
<223> OTHER INFORMATION: SacG: methyl-transferase protein gene
<220> FEATURE:
<221> NAME/KEY: misc_feature
<222> LOCATION: (17244)..(17783)
<223> OTHER INFORMATION: SacH: hypothetical protein gene
<220> FEATURE:
<221> NAME/KEY: misc_feature
<222> LOCATION: (1854)..(2513)
<223> OTHER INFORMATION: SacI: complementary, methyl-transferase
      protein gene
<220> FEATURE:
<221> NAME/KEY: misc_feature
```

```
<222> LOCATION: (335)..(1861)
<223> OTHER INFORMATION: SacJ: complementary, mono-oxygenase
      protein gene
<220> FEATURE:
<221> NAME/KEY: misc_feature
<222> LOCATION: (18322)..(19365)
<223> OTHER INFORMATION: Orf1: aminoacid peptidase-like protein
<220> FEATURE:
<221> NAME/KEY: misc_feature
<222> LOCATION: (21169)..(22885)
<223> OTHER INFORMATION: Orf2: complementary; hox-like regulator protein
<220> FEATURE:
<221> NAME/KEY: misc_feature
<222> LOCATION: (23041)..(23730)
<223> OTHER INFORMATION: Orf3: complementary; glycosil transferase-like
      protein
<220> FEATURE:
<221> NAME/KEY: misc_feature
<222> LOCATION: (25037)..(26095)
<223> OTHER INFORMATION: Orf4: isochorismatase-like protein

<400> SEQUENCE: 1
ctgcaggtgg tttgcgcgcg aagacccgc  cactgccggt gcgctcgttt gaattgcaca      60
tggcgtggcg tgggtcgcag gataatgatc cggggagcg  gtggttgcgg tcgcggattc     120
agatgttttt tggcgacccc gatagccttt aattaaactc cactaaaatc ggcgattgca     180
gagcctgagt acaacacggc tactggactg aagtgggcgc atcgtgccgc atagccatag     240
tgatctcggt gtgtctcgcc atgtcccggc ccaggtcgta ggtcatgctc ttgcgcattg     300
ccagcatctt cgtgctccct tgccagctgt ttcaggtcag gctctgacgc gcggatttag     360
aatcgtccag cagccactca cccaagcgct ccttggccaa ggtcgatttt ttaccgaccc     420
agatcaccac gccatccggc ctgacgatga ctccctcgcc agcggacaag ctgttattgt     480
gcgaatcctc gcagatagat gccgtttgca accccgaaa  atcacgtcga agatcggcgg     540
ccagtgcttt ggcacgatga tgtaccagga caaaccgccc tgctcgcagc aactgggtca     600
agctctgtcg tggtaatcgc tcaccctcgg gaagcaggct caacagggggt aaacgtcggc     660 ccaccaagcg atgatcgcct cggcgccgca cactgtcata gcgcacgccc tctcccgcca     720
gtgcactgac caccttctgc gccacatacg ggcccgtgt  cgcctgcaag ccgatccagt     780
gaatcagacg gcctataggg ccggaagccg tattgaatcg gaaagcaga  tccgtgttgc     840 gcaaggctgc cgccgcaata ggcctacgct cggcctcgta actctccaga agatccatcg     900
gcaatgtggc ctgtatcaca cccgccagct tccaggcgag gttcgccgcg tcaccgatcc     960
ccatctgcaa accttgcccc cggcgggga  cgtgggtgtg agcagcatct cccagcagaa    1020
ataccctccc ctggcgataa tgagtcgcca ggcgctgctg gctgcggtaa cgagcgctcc    1080
acagcacctg cgccaatccg aaatcggttc cagaatatc  tttcatccct ccggcaattt    1140
cctcgtgggt gaccggctgt tgaccggag  tatccatacg ttcgttgtct tcgatactga    1200
cgcgataact gccatcgggt aatggaaaca gggcaaccag accctggag  accgaccttg    1260 catggactgc aggtgaaggc ggatttctca agacaacgtc cgccaccacc aacgaatgct    1320
tgtagtcctg cccgacaaac gaaatattga ggagttggcg gacagaactg ttgaccccat    1380
cagcccccag cacccagtcg tagcggcttt gctgcacgct gccggtctcg ctgtgttcca    1440
gggttacctc aacgtgtaaa tcgccggcat ccagagcctt tagcgcatac ccacgcttca    1500
gattcacccc cttgcgattg acccaatcag tcaacaccga ctcggtctga gactgtggga    1560
tgatcaccat gtgggatac  tcacaaggga gtttggaaaa tgagagcgtt cggcccgcct    1620
tgtcacccaa cggcgcgctt gcccagacga tccccgacg  tatcatctca tctgccacgc    1680
```

-continued

```
cccaggcatt gagcaactcc agggtcacgg gctccaagcc aaaggcccgg gaatggggag      1740
aggcagccgg tcttttatcg atgagatcaa ccgctatacc caactcggcc agagctgcag      1800
ccacagccaa cccgacgggc cccgccccca cgaccaggac ctgtttattt ttaacgacca      1860
tgatcaccca cctctccaca gcaggggcgg aacgtggcga caatgacgtg ctggtcggtg      1920
acgctcgttt ccatgctctg cagcccggcc gtttgcgcga gctggattac ctcatgctct      1980
gatcgataat ctgccagtga gcccagcagc cagttgatca atgtggtcaa tccccagccc      2040
gcaggcaggt tctccaccag gcagaaaagg ccctgaggct tgagcacgcg acggacctca      2100
ttcaggctga cagacttgtc agcccaatgg ccgaacgaca tcgagcacac caccagatcc      2160
atgctttgcg aggggaatgg caaggcttcg gcaactcctt tgacgaacga ggcgaaggga      2220
cgtcgtttgg cggcctcgtc gaccatgccc tgagccgggt cgacgccttc gaagcgcgcc      2280
tcaggccaca gagcgaacat gcgttcgatc aatgcgccgg taccacaacc gatgtccaga      2340
acacgctccg gtctcgaggt gcacatccat cggctcaaca ttcgcagaca gtcgtcatgg      2400
gcctggctca gtttggtacc gtacttctct tcatacgtcg gcgcgatacg gctgaacgtc      2460
cgcacaaaac ctggatttcc attgcctttc ccgccagaaa atacgttaga cattattgaa      2520
catccatata tcaacagtta tccgccaagg accatagtag agaaaatcca tcccatccaa      2580
ataaaaatta aataagtggg gctaaccgca atccagggaa actctgaaaa ggcccgctac      2640
ttgtcgacgc ggctgtctgg aggccgcata gttactgaac ttactattaa aagactgggc      2700
tttttcagag ccccaccgga tgttggctcc ttgtccatca tttcgggggc actgtaacat      2760
tctgttacct ggctatcgct tgacttttaa tctgaacggg caattatagg tctaaccgca      2820
acagccccac ggcgcttaag ttcgaaaaaa gtagctgcac cttgctcaac tgcatcttgt      2880
aataaggggc actttacaag ccgcataaga cataaatttt atgctgactc cccaaacaag      2940
cacgacaagt aaaaaacact tgtccaatac caaggagggt atacggtgca agcttcttta      3000
cgtcaaaaag ttctctgctt acagcagtct atcgatccca gccagccagg catgttactt      3060
gaagtcgctt tcatgtgat cacccatctt tctacttcgc agttggtatc gcgtatcgag       3120
agagtggtcg agcgacatgc gtctttacgg cagcgctttg tcatgcgcaa tggcacttac      3180
tggattgaac aagccccacc gcaacaacga cgctactgcg tggtacgcac ctatgatgaa      3240
gcatcgaccg atgcactgct ggcgccgagc cgcgagcaca tcggggttga gtctgagcgt      3300
ttgttccgcg ccgaagtcgt tgagcgcagc gacggacaac gctacttggt cttccgaatt      3360
catcacatca tcgccgacct gtggtctgtc ggcctcctga ttcgagactt tgccgaagac      3420
tgtatggacc gctccagcat caccctggcg tcaagaccga ttgccccgtt gatcgaccct      3480
gagttctggc ggcaccaaat gtcacaggac actccgtttt ccttgcccat ggcctccctg      3540
gaacagcaca cggaccgccg catggtgctg tcttcgttcg ttattgatca ggagagcagc      3600
gctgacctgg cccgcctggc cacagcctgc gcggtaaccc cgtacaccgt aatgctcgcc      3660
gcacaagtat tggcgctgtc cagaatcggc cagagtggcc gtctgtcact tgcggtgacg      3720
ttccatggcc gcaacagggg caacaaggat gcggtaggtt acttcgccaa tacgcttgcc      3780
gtgcctttcg atgtcagcga atgcagcgtg ggcgagtttg tcaaacgcac cgccaagcgc      3840
ctggatgagg cctcaaaagc cagcgtcggt gccggttatc ccgaattggc agagttcatg      3900
acgccgctgg gatgggctgc gaccgccccg accaatgcgg tgatttacca gcaggatatg      3960
ccaggcatgc caagaggatt ggcggcggct ctgctgggat tgggcacggt gcagttgggc      4020
gagatggcgc tgaccgcgga acaggcaccg cccagcatcg gcccgtttgc cactgcgctg      4080
```

```
ctgctgacgc gccacgacgg caagctgcat ggccgggtcg aggtcgatcc tgcgcagcat    4140
cccggttggc tggcagaggc gttagccaga cagttcgctg tgatcctgcg ggaaatggtg    4200
cgtgatccac aggccagact gtcagccttg ccagcgtgcc tgttacacca accaaaatac    4260
ccgagccaag cgcggccggc gcctgcgtca gaaacattgg tagccacctt tctccggcaa    4320
gtcgccatca cgccggacaa gcccgcgctg cgtacgccgc aggccagcat cagctatagc    4380
gaattggcca gtcgagtcgc caggctctcg gcagccttgc gcgtacgcgg cttcaaacct    4440
gaacagaccc tggcaatact cctgcctcgc gatatcaatc tggtacccgc tctgctggcg    4500
atcatggcct gcggtggcag ttatgtgcca ctcagtgacg cgaaccccgc cgaactcaac    4560
cgttcgattc tgaccagggc ccgttgccgc gcgattctca cggatcagga gggtttgacc    4620
cgtttcgctc acttggcgcc ctgctggtcc ttgagcgacc tgctgtcgat gcccgacgcc    4680
ccgctgcagg accagtccaa gcttcaagcc aaggcctata tcctatttac cagcggctcc    4740
accggtgaac caaaaggcgt ggcgatcacc catgctaatg ccgccaacct gctgcgttgg    4800
gcggctctcg attgtggccc cgagtacctg gcgcaaacac tggcggcaac ccccactacg    4860
ttcgatcttt cgattttcga gatgtttgct ccccttatgg tcggtggctg cgtacagccc    4920
gtttcctcgg tcatggcgct gatcgacaat ccggccctgc taaagggcac aacactgatc    4980
aatacggtgc cgtcggtggc cgacgctttg ttgcagcatg atgtactggt gccttccttg    5040
cgcatgctca acctcgcggg agaacccctg aaccgggatc tttacctgcg gcttcaggca    5100
aaactgaccg ccacacgcat cgtcaacctc tacgcccga cggaaacaac aacctattcc    5160
accgccctgg tgatcgagcc cgcacaacaa gagatcacca tcggttttcc actgtatggc    5220
acctgggtgg atgtcgttga tcaaaacatg caaagcgtcg gtatcggtgt acctggcgag    5280
ttgatcattc atggacacgg cgtggcgcaa ggctatgtca gcgacccgt gcgtagcgcc    5340
gcttcttttcc tgccggcatc cgatggcttg cgttgctacc gcacgggaga ccgtgtccgc    5400
tggttgcccg atggccgcct ggactttatc ggtcgagagg atgatcaggt caaagttcgc    5460
ggtttccggg tcgagttggg gcctgttcag gcggcactgc atgccattga gacgattcat    5520
gaatccgcag tagtcgttgt gccgaaaggg cagcagcgca gcatcgtggc gttcatcgtc    5580
ctcaaagcgc cgagcgaaga tgaagcggtg cagcgcaata acatcaaaca acacttactc    5640
ggcgtactcc cctattacgc actaccggac aagtttattt ttgttaaagc actgccaaga    5700
aacacacatg gaaaaatcga cagaacgctg ctcttgcaac atgagcccca gactgagcaa    5760
gaaagcgcca tgcgagatgc gaccgacgtc gaacatcgca tcgccaactg ctggcaaacc    5820
atcatcggac accccgtcca actccacgaa aacttcctgg acattggcgg ccactcgctt    5880
tcgcttacgc atttaacggg cctactgaga aaagaattta atattcatat ttctctacac    5940
gacctctgga tcaggccaac catagaacaa caggccgact tcattcataa gttgcaaaat    6000
tcggtattga caaaacctgc cgccgcgcca atcccgcgac ttgaccgaaa gatctctcat    6060
cattaatcag gagtaccgca tgagcgtcga tacatgcagg actgcaactt ccctgcgtc    6120
atacggccag gaacagatct ggtttctgaa cgaactaaac ccgcactctc aactggctta    6180
taccctggcg atgaaagtat ctatcgccgg gaaattgaac acactgcggt tgcagcgtgc    6240
ggtcaaccaa gtggtggcct cccaggaaat tttgagaaca tcattcgcct ataaaaacca    6300
gaagttgagc caggtcattt cacctccgg gacactgccc attcgcagcg cgcactgcat    6360
tgacgatgta cctgggctgc aacgcctgat caacatggaa gcccagcgtg gctggtcgct    6420
```

```
gagcagcgcg ccactgtacc gcttgctgct gataaaaacc ggcgaccagc aacatgagct    6480
ggtcatctgc acccaccata tcgtctgcga tggcatctcg ctgcaactgc tgctgcaaaa    6540
aatagtcagc gcctatcaag gccaaagcga tgggcgggtg ctcacaagtc cggatgaaga    6600
gaccctgcaa ttcgtcgatt atgcggcctg gtcaaggcag cacgaatatg ccggtctcga    6660
gtactggcgc cagcaactgg ccgacgcccc gacaatcctg gatatttcga caaaaaccgg    6720
ccgaagtgag caacagacat ttctcggcgc gcgaattccc gtcgagttca gccaccacca    6780
atggcaagca ttgcgccaga tattcagacc ccagggtatc tcctgcgcgg cggtgttcct    6840
ggcggcctac tgcgtcgtcc tgcaccgcct ggccgagcag gacgacattc tgatcgggct    6900
gccaacttca aatcgcctgc gtccggagtt ggcacaggtg atcggctacc tgtccaatct    6960
gtgcgtgttt cgcagccagt atgctcacga ccagagcgtc acagactttc ttcaacaggt    7020
tcaattgacc ttacccaact tgatcgagca cggggagacg cctttccagc aagtactgga    7080
aagtgttgag cataccccgg caagccggtgt gacgccgttg tgccaagtac tgtttggtta    7140
tgagcaggac gttcgacgca cgctggatat cggcgacctg caattgacgg tctcggatgt    7200
ggacacgggg gccgcacgcc tggatctatc gctgttcttg ttcgaggacc acgaactcaa    7260
cgtttgcggt tttctggaat atgccacgga ccgtatcgac gccgcatctg cgcaaaacat    7320
ggtgcgcatg ctcagcagcg tgctacgcga gttcgttgcg gcgccgcagg cgccgctcag    7380
cgaagtacag ctgggggcgg cggattccca agcccagaca cctgcgatcg caccagcatt    7440
cccaagcgtg ccggctcgtc tgttcgcctt ggcagacagt caccccaatg cgaccgcgct    7500
gcgtgacgag caaggtgaac tgacctatgc gcaagtttgc caacagattc tgcaggcagc    7560
ggccactctg cgagcccagg gggcgaaacc tggaaccctg atcgcggtca tcggcgagcg    7620
cggtaacccc tggttgatcg ccatgttggc gatctggcaa gtcggcggta tctatgtgcc    7680
attgtccaag gacctgcccg aacagcgcct gcaaggcatc ctggcggaac tcgaagggc    7740 catactgatt accgacgaca ccacgccgga acgcttccgg caacgtgtga cgctgcccat    7800
gcacgcctta tgggccgatg gcgcaacgca tcacgagcgg cagacgacgg acgccagccg    7860
gctgtctggc tacatgatgt acacctcggg atcgaccggt aaaccgaaag gcgtgcatgt    7920
cagccaggcc aacctggtcg cgaccctgag cgcattcggc cagctgctgc aggtgaaacc    7980
cagcgatcgg atgctcgcac tgacgacctt ctccttcgac atttcgctgc tcgagctgct    8040
gcttcccctg gtccagggcg ccagcgtgca atcgctgtc gcacaggctc aacgcgatgc    8100
ggaaaagctc gcgggctatc tcgcagaccc tcggatcacg cttgttcagg ccacaccggt    8160
gacctggaga ctattactgt cgacaggctg gcagccacgg gaaagcctga ccctgctgtg    8220
cggtggcgaa gcgctgccac aggatctggc ggacaggttg tgcttgccgg gcatgacctt    8280
gtggaacctc tacggcccca ccgaaacaac aatctggtcc acggcctgcc gcctgcaacc    8340
gggtgcgccg gtgcaactgg gccatcccat tgcaggtacg caaatagccc tggtggatcg    8400
gaacctgcgc agcgtgccca gaggggttat cggtgaactg ctgatttgcg gccccggcgt    8460
cagccagggc tactatcgca acccggttga acagccaag cggttcgtac cggacccgca    8520
tggttcaggt aagcgcgcct atctgaccgg cgaccggatg cgcatgcagc aggatggttc    8580
gctggcctat atcggccgac gtgacgacca gatcaagctg gcggccacc gtatcgagct    8640 gggagagatc gagacagcgt tgcgaaaact gccggcgta cgggatgctg ccgcccaact    8700
ccatgaccag gacccaagtc gaggcataca ggcctttgtc cagctttgcg caacggtcga    8760
tgagagcctc atcgatatag gccagtggct ggaaacactg cgccaaacgc tgcctgaggc    8820
```

```
gtggctgcct actgagtatt acaggatcga tggcatccct cttacctaca acggcaaacg   8880
cgacaggaag cgcctcctgc accaggccgt caggctgcaa acactcagtc tgagggtggc   8940
tcccagcagt gacaccgaga cccgggtgca gcagatctgg tgcgagctgc tcggtctcga   9000
ggatatcggc gttacggatg atttttcca gttaggcggc cactccattc tggtggcgcg    9060
catggtcgag cgcatcgaaa ccgcgtttgg acggcgcgta cctatcgcag atatctattt   9120
ttctccgacg atcgcccgtg tggcggcgac gctggactcc atgacatttg aacaaggact   9180
ggccgcacac agcgtgaaag gcgattggga gttcaccgcc atcagccttc aacacaacgc   9240
cgacagcaca gccgccgctc aggagagatg aatcatgcac agccccacta tcgatacttt   9300
cgaggccgca ctgcgctcat tgcccgctgc ccgcgacgca cttggtgcct atcccttgtc   9360
cagcgaacaa aagcgcctct ggttactggc ccaactggcg ggcacggcaa cgttgccggt   9420
aacggtgcgt tatgcattca ccggcacggt ggaccttgct gtcgtgcagc agaacctgag   9480
cgcgtggatc gcacacagcg agtccttacg cagccttttc gtcgaagtac tggaacgccc   9540
cgtcaggctt ctgatgccta cgggcctggt gaaactggag tacttcgatc gcccgccatc   9600
cgatgccgat atggccgagc tcataggcgc gcctttgaa ctcgacaaag gccgttgct     9660 gcgtgcgttc atcactcgaa ccgctgcaca acagcatgaa ttgcatctgg tcggccatcc   9720
tattgtcgtg gacgaacctt ccctgcagcg cattgcccaa accctcttcc agaccgaacc   9780
cgatcatcag taccccgccg tcggtgcgat cgccgaggta ttccagcgcg aacagacact   9840
ggcacaggat gcgcaaatca ccgaacaatg gcagcaatgg ggaataggcc ttcaggcgcc   9900
tgcggcaacc gaattccga ccgaaaaccc ccgccccgct atcaagggct cagatcgtca    9960
agtacatgaa gccttactg catggggcga ccaacccgta gcagaggccg aaattgtcag   10020
cagttggctg accgtgctga tgcgctggca gggatcgcaa tcggcgcttt gcgcaatcaa   10080
ggtgcgcgac aaggcgcatg ccaacttgat cggcccactg caaacctacc tgccggtccg   10140
cgttgatatg ccggatggca gcaccctggc acaactgcga ctccaggtgg aggaacagct   10200
caatggcaac gaccatccgt ccttttccac gctgctggaa gtttgcccac caaagcggga   10260
cctgagtcgc acccctact tccaaaccgg cctgcagttc attgcgcacg atgttgaaca    10320
gcgcgacttc catgccggca acttgacacg cctgccaacg aagcagccaa gcagcgacct   10380
tgacctgttc atttcctgct gggtaagcga cggcacgctt ggcctgacgc tggattatga   10440
ttgcgccgtg ctgaattcga gccaggtcga ggttctggcc caggcgctca tcagcgtatt   10500
gtcagcgccc ggtgaacagc caatcgcaac cgttgcgctg atgggccagc aaatgcagca   10560 accgtcctg gctcaggccc acggcccccg cacgacgccg ccgcaactga cactgaccga    10620
atgggtcgcc gccagcacgg aaaaatcccc gctggcggtt gcggtgatcg accacggcca   10680
gcagctcagc tatgcagagt tatgggcaag agctgcactg gtagcggcga acatcagcca   10740
gcatgtggca aagcctcgga gcatcatcgc tgtagcactg cccagatcgg ctgaatttat   10800
tgcagcgctg ctgggggtag tgcgagcagg tcatgcgttc ttgcccatcg atccccgcct   10860
gcccaccgac cgcatccagt tcctgattga aaacagtggc tgtgagttgg tcattacctc   10920
tgatcagcaa tccgtggagg gttggccgca ggtcgccagg atacgaatgg aggcgcttga   10980
tccagacatt cgctgggtgg cgccgacggg gctcagccac agcgatgccg cctacctgat   11040 ctataccctcc ggcagcaccg gcgttccgaa gggagtcgtt gtcgagcacc ggcaagtagt   11100
gaataacatc ttgtggcggc aacgaacctg gccgctgacg gcacaggaca acgtgctgca   11160
```

```
taaccattcg ttcagcttcg atcccagcgt ctgggcgttg ttctggccgc tgctgaccgg    11220
tggcaccata gtgctggcgg atgtcagaac catggaggac agcaccgccc tcctcgacct    11280
gatgatccgc catgatgtca gcgttctggg tggcgtaccg agccttctcg gtacgctgat    11340
cgatcatcca ttcgccaatg attgccgggc ggtcaagctg gtgctcagtg gcggcgaagt    11400
cctcaacccc gaactggcac acaaaattca aaaggtctgg caggccgacg tcgccaacct    11460
ctatggccct accgaagcga ccatcgatgc gctgtatttt tcgatcgaca aaaatgctgc    11520
cggcgccatc ccgattggct atccaatcga caataccgac gcttatatcg tcgacctcaa    11580
tctcaaccca gtcccgccag gcgttccggg agaaatcatg cttgctggcc agaaccttgc    11640
gcgcggctat ttgggcaaac ctgcgcaaac cgcgcagcgc ttcctgccca acccatttgg    11700
caacggacgc gtgtatgcaa cgggcgatct gggacgacgc tggtcatcgg gggccatcag    11760
ctacctgggc cgacgcgacc aacaggtgaa gattcgcggg catcgcattg agcttaacga    11820
agtcgctcat ctgttgtgcc aggcgcttga gctgaaggaa gccatcgtct tcgcccagca    11880
cgctggaacc gaacaggcac gcctggtggc ggccatcgag caacagccag gcctgcacag    11940
tgaaggtatc aaacaggaat tgctgcgcca cttgccagcc tatctgatcc ctagccagct    12000
cctgctattg gatgaactgc aagaaccgc caccggcaag gtcgacatgc tcaagcttga    12060
tcagttggca gcccctcagc tcaatgacgc cgggggcacg gaatgccgtg cgccacgtac    12120
cgaccttgaa caatcggtca tgacggattt cgcccaagta ctcggcctca ctgcggtaac    12180
gccggacacg gatttcttcg agcaaggcgg caactcgatt ctactcacgc gcctggcagg    12240
caccttgtct gccaaatacc aggtgcagat tccactgcat gagttttcc tgactccgac    12300 cccggcagcg gtggcgcagg caattgaaat ctaccgtcgc gaaggcctca cggcactcct    12360
gtcacgccag catgcacaaa cgctggagca ggacatctac ctggaagaac acattcggcc    12420
ggatggctta ccacatgcca actggtacca gccttctgtc gtgtttctga ccggagccac    12480
cggctacctg ggactgtacc tgatcgaaca gttgctcaag cgcaccacca gccgcgtcat    12540
ctgcctgtgc cgtgcaaagg atgccgagca tgccaaggcc aggattctgg aaggcctgaa    12600
aacctaccgc atcgacgtag gcagcgaact gyaccgggtg gagtacctca cgggcgacct    12660
ggcgttgccg cacctgggcc tgagcgagca tcaatggcaa acgctggccg aagaggtcga    12720
tgtgatttat cacaacggcg ccttggtcaa ctttgtctac ccctacagcg cactcaaggc    12780
gaccaacgtg ggaggcacgc aggccattct ggaattggcc tgcaccgctc gactcaagag    12840
tgttcagtat gtctccaccg tggatacgct cctggcgacg catgtccccc gccctttat    12900 cgaggacgat gccccctgc gttccgccgt cggcgtacca gtgggctaca caggcagcaa    12960
gtgggtggca gaagggtgg ccaatcttgg cctgcgtcgc ggcattccgg tcagcatctt    13020
ccgcccgggc ttgatcctgg ccataccga acgggtgcc tcgcagagca tcgactacct    13080
gctggtggcg ctacggggtt tcttgcccat gggcatcgtg ccggattacc cacgcatctt    13140
cgacatcgtg cccgtggact aygtcgccgc ggcgatcgtg cacatatcga tgcaaccgca    13200
gggcagggac aaattcttcc acctgttcaa cccggcgccg gtcaccatcc gccagttctg    13260
cgactggatt cgcgaattcg gttacgagtt caagttggtc gacttcgaac acggtcggca    13320
gcaggcattg agcgtaccgc ccgggcacct gctgtaccg ttggtcccc tgatcaggga    13380 tgccgatccg ctgccccacc gcgcgctgga ccctgactac atccatgaag tgaaccccgc    13440
actggaatgc aagcaaacct tagagctgct ggcctcctcg gacatcaccc tgtcgaaaac    13500
cacaaaggct tacgcgcaca caatttttgcg ctacctgata gacaccggct tcatggccaa    13560
```

```
gcctggcgtg tagcggattg agcacaaaca ggacgaatat catgaatcg atagcctttc   13620
ccattgcaca taagcccttc atcctgggct gtccggaaaa cctgccggcc accgagcggg   13680
cgcttgcccc ttctgcggcg atggcgcggc aggttttgga gtacctcgaa gcgtgccccc   13740
aggcgaaaaa cctcgagcag tacctcggga cgctgcgtga agtcctggcg cacctgcctt   13800
gtgcttccac cggactgatg accgatgatc cacgggaaaa ccaggaaaac cgcgacaacg   13860
atttcgcctt cggtattgaa cgacaccagg gcgacactgt gaccctgatg gtcaaggcca   13920
cccttgatgc agcgattcaa acgggcgagt tggtccaacg cagcggcact agcctggatc   13980
actcggagtg gagcgacatg atgtcagtcg cacaggtgat tctgcagacg attgccgacc   14040
ctcgggttat gcccgaatcc cgtttgacgt tccaggcacc gaaaagcaag gtcgaagaag   14100
atgaccagga cccgctgcga cgctgggtgc gtggccacct gctgttcatg gtcctgtgcc   14160
aaggcatgag cctgtgtacc aacctcctga tcagcgcggc ccacgacaag gacctcgaac   14220
tggcgtgtgc acaggccaat cgcctgattc aactgatgaa catctcgcgc atcacgcttg   14280
agtttgcaac cgacctgaac tcacaacagt acgtcagcca gattcgcccg acgtcatgc    14340
cgscgatcgc gccgcccaag atgagtggca tcaactggcg tgaccatgtg gtgatgattc   14400
gttggatgcg ccagtccacc gatgcctgga acttcattga gcaggcctac cctcaactgg   14460
ctgaacgtat gcgaaccaca ttggcgcagg tctacgcgc tcatcggggg gtctgcgaaa    14520
agttcgtagg cgaagaaaac accagtttgt tggccaagga aaacgccact aatacggccg   14580
gccaggtgtt ggaaaacctg aagaaatcga gattgaaata cctcaagaca aaaggttgcg   14640
ccggtgcggg ataagccctg actgcgcctc gcccccatca aaaccggact gatattcggg   14700
aaaacaaagg agagaagcat gccgacattt ctgggagacg acgacgcagt gccatgcgtg   14760
gtcgtcgtta acgccgacaa acactattcg atttggccaa gcgcgagaga cattccatca   14820
ggttggtccg aagaaggatt caaggggtca cgttcagact gcttggaaca tatcgcgcaa   14880
atctggccag agccgacggc atagatacaa cgtgatgcaa aaaatgcggg aaacatcaac   14940
taaccaaagc aaggaagaaa aatgacttca actcatcgca ccactgatca agtcaagcct   15000
gctgttctgg atatgccagg cctgtcgggc attcttttcg gccacgccgc attccaatac   15060
ctgcgggcca gctgcgaatt ggatctgttc gagcatgtcc gcgacctgcg cgaagccacc   15120
aaggagagca tcagcagccg actgaagttg caggaacgcg ccgccgatat tctgctgctg   15180
ggcgcgacct ccctgggcat gctggtcaag gaaaacggca tctaccgcaa tgccgatgtg   15240
gttgaggatt tgatggccac ggacgactgg caacgtttca aggataccgt ggcctttgaa   15300
aactatatcg tctatgaagg gcagctggac tttaccgagt ccctgcagaa aaacactaac   15360
gtcggccttc agcgtttccc gggcgaaggg cgggacctct atcaccgcct gcaccagaat   15420
cctaagctgg aaaacgtgtt ctaccgctac atgcgctcgt ggtctgaact ggccaaccag   15480
gacctggtca agcacctcga cctgtcgcgc gtgaaaaaat tgctcgacgc gggtggcggt   15540
gatgcggtca acgccatcgc cctggccaaa cacaatgagc aactgaacgt aacggtactg   15600
gatatcgaca actccattcc ggtcactcag ggcaaaatca atgattccgg gctcagccac   15660
cgggtgaaag cccaggcatt ggatatcctg caccaatcct tccctgaagg ttacgactgc   15720
attctcttcg cccaccaatt ggtgatatgg accctcgaag aaaacaccca catgctgcgc   15780
aaggcctacg atgcgctacc agaaggcgga cgcgtggtca tcttcaactc catgtccaac   15840
gatgaaggcg acggcccggt catggccgca ctggacagcg tctactttgc ctgtctaccc   15900
```

```
gccgagggcg gcatgatcta ttcctggaaa cagtatgagg tctgcctggc ggaagccggc    15960
ttcaaaaacc ccgtacgcac cgcgattcca ggctggaccc cacacggcat catcgtggcc    16020
tacaagtaat tttgcctcct ccgcccctac tggggccgga ggagtcattt caacatttgc    16080
gtcattgacg ccacctggcg atagggacac ccacatggca cgttcacccg agacaaatag    16140
tgcgatgccg caacagataa gacagctttt atacagccaa ctgatttcgc aatcgattca    16200
aaccttctgt gaactgcgcc tgcctgatgt tctgcaagca gctggccagc ctacctccat    16260
cgaacggctt gctgagcaga cacacactca tatcagcgcc ctgtcacgct tgttgaaagc    16320
gttgaaacca ttcgggctag tgaaagaaac cgacgaaggt ttttccttga ccgatctcgg    16380
cgccagtctg acccacgacg cctttgcttc cgctcaaccc agtgctttgt tgatcaatgg    16440
tgaaatgggc caagcctggc gtggcatggc gcagacaatc cgaaccggtg aatccagctt    16500
caagatgtac tatggcatca gcctgttcga gtattttgaa cagcacccgg aacgccgggc    16560 cattttgac cgttcccaag acatgggact ggacctggag atcccggaaa tcctggagaa    16620
catcaacctg aatgacggtg agaacattgt cgatgtaggg ggtggttcag ggcatttgct    16680
gatgcacatg ctggacaagt ggccagaaag cacaggcata cttttcgact acccgtcgc    16740 ggcaaaaatc gcgcagcaac atctgcacaa atctggaaaa gcaggctgct ttgaaatcgt    16800 cgcagggat tttttcaaga gcctgccgga cagtggcagc gtttacttgc tgtcccatgt    16860
cttgcacgac tggggcgacg aagactgcaa ggccattttg gccacctgcc ggcggagcat    16920
gccggacaat gcgctgttgg ttgtagtgga cttggtgatt gaccagagtg aaagtgccca    16980
gcccaacccc acgggcgcaa tgatggatct ttacatgctg tccttgttcg gtatcgccgg    17040
aggcaaagag cgcaacgagg atgaattcag aaccctcatt gaaaacagcg gcttcaacgt    17100
caaacaggtg aagcgcctgc caagtggaaa cggcatcatc ttcgcctacc caaaataaat    17160
gatcctcatt gcccctcgcc actttccagg ggggctattt tattctcggg tgattccccc    17220
cctaatgatt acaaggaaga cacatgtcga cgctggttta ctacgtagca gcaaccctgg    17280
atggttatat cgccactcaa caacacaaac tggattggct ggagaacttt gccctggggg    17340
atgacgcaac ggcctatgay gattttatc agacgatcgg agcagtggtc atgggatcgc    17400
agacctatga atggatcatg tcgaacgctc ccgatgactg gccctaccag gacgtacccg    17460
cctttgtcat gagcaaccgg gatctgtcag cccccgccaa tttggatatc accttcttac    17520
gcggcgatgc cagtgccatc gcggtcaggg ccaggcaagc ggcgaagggc aagaatgtct    17580
ggctggtcgg tggcggcaaa acggcggcct gttttgccaa cgcagggaaa ttacagcagc    17640
tgttcatcac cactattcca accttatcg gcaccggcgt tccggtactg cccgtagacc    17700
gcgcgcttga agtggttctc agagaacaac gcacgctgca gagcggtgcc atggaatgca    17760
tcctggacgt gaaaaagcg gattaacgtc tacaagacaa tcgtgtatcg aaactcgcaa    17820
cgtccaaacc caagggaaaa accagtgaag cgattggtat tgagtttatg tttgttggct    17880
gttatcgctc tcgccagtgt tcaaggaata aggatggtga aacccgccgc cctgacagcc    17940
gccgatgctc gcgatatcgg ctatctgaat gtacgcgata gcctttccgt cattgccgcc    18000 gcccccacc ccaccgcctc acctcgccag gccgttgtca ggcattattt gcgggaaacg    18060
attgcgggca tgggttacca ggtggttgag caaccctttc tatttaccat cgagagcatg    18120
gtgaaccggc agaaaaccct ctatgccgag ttgaacgagc agcagcgcca agcgttcgat    18180
gctgagctgg cccgggtggg gcggacagt tttgaaaaag aagtgcggat tcgctccggc    18240
ctactggaag gcgacagcgg ccagggaacc aacttgatag cctcacaccg cgtaccggga    18300
```

```
gcgaccgcga cggtcctgtt catggcgcat tacgacagcg tcggcaccgc tcccggtgcc    18360
agtgacgatg gcatggccgt cgcctcgata ctccaactga tgcgggaaac cataacccgc    18420
agcgatgcca aaaataacgt tgtctttcta ctcrccgatg gcgaagaact gggcttgctc    18480
ggagcggagc actacgtctc gcagctcagt acgcctgaac gtgaagccat ccgcctggtg    18540
ttgaactttg aagcccgggg taaccagggc atcccttttac tgttsgagac atcccagaag    18600
gactacgccc tgatcaggac tgttaacgca ggggttcggg acatcatatc cttctcattc    18660
acgcccttga tttacaatat gctacaaaac gacaccgact ttacggtgtt caggaaaaag    18720
aacatsgcgg ggttgaattt tgcagtcgtg gagggttttc agcactacca ccacatgags    18780
gacaccgtgg agaaccttgs gccagagacc ttgtttcgct accaaaagac agtgcgtgaa    18840
gtgggcaacc actttatcca gggtatcgac ctctcctccc tgagtgctga tgaggacgca    18900
acctatttcc cactgccagg cggcacgctg ttggtactca acttacccac cctgtatgcg    18960
ctgggcatgg gctcgttcgt gctctgcggt cttttgggcgc aacgctgccg cactcgccga    19020
cagcatcagg gcaagaattg cgtactgcgc cccatggcta ttgccctgct cggcattgcc    19080
tgcgcagcac ttgtattcta cgtcccgagc attgcctatc tattcgtcat ccccagtctg    19140
cttctggctt gcgccatgtt gtcgcgaagc ctctttatct cctattcgat catgctgctg    19200
ggcgcttatg cctgcgggat actctacgcg cctatcgtct acctgatttc atcaggcctt    19260
aaaatgccgt tcattgccgg ggtcattgca ctactcccgc tctgcctgct ggccgtggga    19320
ctggccggcg tcatcgcacg atcgagagac tgtcgaacct gcgactagca agacccgata    19380
aaacgtcgct tcaaacgcca gatgacgtgc ctcgtcagcc aggcgtggaa ccatctggtg    19440
gcggcaaatg tgcataaggt gggaacgcag agcgcccgct gcaacacgcc cacccccaagc    19500 accgcgcctc aacggataat caggctcaag ggaattccac cttgcaacct gaaagagcaa    19560
tcgagcgccc gtcggacaca acaaactgat caccgtcaat tcgggcaagg agcaatccac    19620
gggcttttgc tccaacctca actcccttttg aaaaatcagc cggccacaat ttgcccctac    19680
cctttcagga tatcctcgat aagcgtttta tcagaacagc gaaaaaccac ttcaagttcg    19740
tgtacttttt actgcgatct gcgatcgctc ccatggtaca araatgacag atgggaagat    19800
cgctttaata cctactctct cacctgagaa aaagtaacca ccgggccgta ttcctgatca    19860
gacactatcg cctgcacaca aaatttcttc tctggaaact tactcagcaa caccatcctc    19920
catgactgag caataaggtt gcacagttgt tcataaacag cttcatcgac tctatcgctg    19980
cagcctgcaa aaacatcata caggtgcaca tgattcaaaa ccttctcaac cgccaccaca    20040
tcacgattac aagactgcat ccaactggag aatgcttcaa cagtaaatcc gctttccaga    20100
aacacgcccg actcgtaaac aacaaagtct ggaaacaaca cggtggaaaa caccaggaca    20160
tcttcaggat gtacaacatc actaataaaa caagactcaa ccaactcgga ttgatccttc    20220
cattgggact tccagcgctc gtatttggga gacctgacag ggtctgtcgt cctgattatt    20280
ttcatagcac tgttcctgca ctgatgcctt ttggcgattt tttgtttgag cgagaatcga    20340
tcgatggctc attgttcatc aagaaaaaaa ttctctcgaa acagactctt aagctcggcc    20400
cggcgcgttg agaacagtga aaagtcactc gccacatcct gaatattctc tgtgaccctc    20460
acaagatacc cagtattcag cttttcaatg ggaaagcctg acgcagcaat ccgctcaaca    20520
tcgacctctt cagcaaactc atcgccgtag aacatagccc aaccgatatt gggcacgtcc    20580
ggtttcaaag ccgaattgaa tgagccgatc tgaaaacttt tatatttctc atgcgggcta    20640
```

```
agttcgggtt cactgaacag gtgcagcatt ccgagttgag gaggaaaaat ttcacaccat   20700
gccttgaaga gcgaatacca atcgacgctc ttgctactga ccgagcggta tgtgattgcg   20760
ccaggaacca cctgcccccg gacattgcgc gccgtgtgga tgacgctccc acagccttta   20820
accgccttt  ttctgcgcca ggcaaagtcc aggtagaagt ccgataatgc gccgttaaac   20880
cgtatggccg cctttgatgc ccagcacgct tcactcgcgg ccacgcccat gaaaggctct   20940
ccgaatttat ccgcattgtg cgacacctgc tctggaacca gtaactcccc ttcccgactt   21000
aatgacgaaa tgaacgcctc tccaacaccc caaccgatag tttcagactt cgtcctgatt   21060
gtaatttgca catagggctt cataaatcgt caaagtctcg tcaattcacg ggtgacacaa   21120
gtatatccaa agagctctcc acgttactca tcgcatcgag tctatcaacc aaccaacgcc   21180
gcctcacgcg ccaccgccca cggcgccatc aaccgctgcg gggtctggca ggttttgcgc   21240
ttgagcacga aattgcggca tttctcggcg aattggtggc ggttgtgcac catgtccaac   21300
tgcatctgcg ccagctcggc ttcacggcag cgtgtaatct ggtcgatgtc caacgccgct   21360
ttacgggcgc gagccacggc gtacttttca tcggttaacg cgctgcttgc ctgctgcatc   21420
agccaacggc tgaaggcgtg cgggcagcgc gggccgatgc cctgaaccag cccgtattgc   21480
tcggcttgca aggcactgat cggcaggcag gcgtcggtga gttgatgggc gacttcactg   21540
ccaacggcgc gtggcaggct gtaggtccag tattcggagc cgtacaggcc catggttttg   21600
taatgcgggt tgagtaccac gctctcgcgg gccaatacga tgtctgcggc cagcgccagc   21660
attacaccac cggcgccggc gctgccggtc aggccgctga tcaccagttg ccgggccgtg   21720
agcagttcgt ggcacacatc gtacgatggc ctgaatgttg gcccaggctt ccagccccgg   21780
cactggggcg gcctggatga cgttgaggtg cacaccattg gaaaagctgc cgcgcccgcc   21840
cttgatcacc agcacttggg tgtcccgcgt cttggcccag cgcaacgccg ccaccagtcg   21900
ctggcactgc tcggtgctca tggcgccgtt gtagaactca aggtgagtt  caccgacatg   21960
gccggcttcg cgatagcgaa tcggttgata ggcttgctca tcgaacattt gattggcgat   22020
cgagctgtcc agcacgggaa tatccgccag tgcttccgcc agcacgtggc gggccggcag   22080
cttgaaggtc tcctccccg  gccgggcttt gcgtttgagc gagccgatcc acaggctctg   22140
atcaccggcc gccaccagca ccgcgtcgtc ctgcaccgcg aggatctcac ccggtgtgcc   22200
gtggcgcgca tccaggtgcg cgtcgtacag gtaatactgc ccgccctgga tactggccag   22260
cacaccgggc tggccatcgg ctgcgtcgat gcagcgtttg atgaagcgtg cgcaatcgta   22320
ccaactgaag gtgcgatcag cctgtgtcat gttcggctgc aaacgcccga ttacgtgggc   22380
ttgggtgtaa tcgagcggca ccgggacgaa aacccgggcg aacttttcca ccacgtcgcg   22440
gatgcaatag agggcggcgt cactcaccgc gccgttgtac agctcggatt tgcgcacatc   22500
ggcaggcatg tcgaattcac aggtcgacca gatcggcccg gctccatttc ctccaccgcc   22560
tgcaaagccg tgacgcccca gcggccgacc tgctggctga tgcccagtc  cagcgcgctg   22620
gcaccacggt cgccgacgat gcccggatgg ataatcacca cagggcgctc aaggttgctc   22680
caaagttgct gtggcacacg gtctttcaga aaggggcaga tcaccaggtc ggcgtctgaa   22740
tcctcgatct gctggcacac caaggctgga tcggtgaaca gaacaacgct gggcgcgtgc   22800
cccgactggc gtaaatccag ccaggcccgc tgggtcaaac cgttgaacgc cgacgctaac   22860
acgatgatct tcaatgaccg catggctgac tcatccttga gaatgcgcgg ccagaggtgc   22920
tccttgagcc ctccctggcc tttgatggaa gtacaaggat agttggcgtg ccaggcaggc   22980
tacctgatca ggatcaatct tgtgtcagcg agtgcttgaa cgtaggcgcc tgcgttcaac   23040
```

```
caataggcgc atggsctggc gagtgctccc gcgtgccctc tgccacaagg gacgccaggt   23100
attcgccaaa cccgccgcga cacttgtagt cccgacgcgc actggtgacc acgggattgg   23160
tcgccgtcca cacgatccgc gcgccaatcc tctcgaggtc ggccaccaac tgcacatctt   23220
catgggcaac caaatgctgg aacccacccg cgtttcgata ggcatccgca ctcaagccca   23280
ggttggcacc gtgtatatgg cggtggttct cggtgaactg atacaactca aggtagcgcg   23340
aacgaaccga ttcaccgtac tcgctccagc tgtccacctc gacggttccg cacaccgcat   23400
cggcgccaaa gccgatctga cgcaccagcc agtcgrcggg cacaactgtg tcagcgtcgg   23460
tgaatgccag ccactgggcg ccgacttcaa gcaatcgctc cgcgcccaag gccctggcct   23520
tgcccacatt tcgaacgctc acctcaagcg tkgcgacacc catggccgac acgcgcgtgg   23580
cggtctcgtc cgaacacgca tccagcacca ccagcaattg gacctgttgg tgtgccagag   23640
ccggatgagc aatggcgcgc tggatggagg cgaggcaggc actgatgtgc cgttcttcgt   23700
tatgggcagg tatcactatc cctatcattg acgttccctc taccaggcaa agtgtctaca   23760
gctatcgacc gggccgtgag gcagaaggtt taaacaatct gaaggcgccg ccaaacaatg   23820
acgtgagaca ggtcgcagtg attaaacgga acgtcacagg cgccacaggc tcagatggtt   23880
tacgtgtttg atgcacggat gaacccgcca ttcctacaaa caggtcagcc atcatgtcta   23940
acgattatca aggtatcgcc agtgtcatca cggcttctcg tcacatgggt acagactcgg   24000
atgaacgcct taatgagacg gtaaatattc aattgacctg cagcggtaaa ccaacgattg   24060
cgcggttgag tttcgacacc ccgcttcaat ggcccggcca ccccaacttt gtgctgatca   24120
acctgccgga cggttcatcg gtgggtggtg tgattgccga aattgaaaag tcgaccgatg   24180
gcccgggttg ggtgacgttt acggtggatg actgaggtct tcccaacagg cttcaaatca   24240
cctccaggcg gctgcctcga atgagacaca caggccagta atcgagacgc acagacaagc   24300
ctattttcgc agatacattt tgtaacgtcc tatgattgac gcttgctcga atcaccgcga   24360
gggattgggt ggcgtgtgtt tatcacgccc ttgaatccgc agcgaaaaat gattcgagtt   24420
cagcgaacaa ttcgattggg acaaacaaaa ggatgcgggc tatgtcattg cgtaatttat   24480
ctttattggt caccacactg gcgctgttta agtggggtgt aatgcgctcg cggggcaaaa   24540
cccaacatgc tcagtgatga tgacgtgaaa tcccaaagcg ccggcgcact gggctatgcc   24600
ccgacagacc tgagcatcgt caaccgtcga accgaaggca ccaacaccta cgtgctgctt   24660
aaaaccaacg acaacaagca gttcaactgc attatcaacg gaggcaatat cctgaccttc   24720
ggtatgtcca acccgccttc gtgtgcgaag aaaggtgaac agatcaagag tggcccgttc   24780
gggagctgat ctgtcgctgg aaaaaagggc caggccacct ctaagaacgg aggcctggcc   24840
cttttttatt cgctcagatg agtttaaaag acaagatatc gggcagctgg gctccggccc   24900
gttcagtctg gcacccccac acaaaatgct cagcgactac ttggccgtcg ccgcacaccg   24960
gtttaacggg tgcgacctac agcgtcrccc tggttgaagg cagcaacgaa taaaccctat   25020
tgatcggaga gcgaccatgc acccgcataa aaccgcgatt gtcttgattg aataccagaa   25080
cgacttcacc accccggcg gcgtgttcca tgacgctgtg aaagacgtca tgcaaacgtc   25140
caacatgctg gcgaataccg ccaccacgat tgagcaggcc gcaagctgg gcgtgaagat   25200
catccactta cccatccgct ttgccgacgg ctacccagag ctgaccctgc gctcatacgg   25260
cattctcaaa ggcgtcgccg acggcagcgc gtttcgtgcc ggcagctggg gcgccgagat   25320
caccgacgcg ctgaaacgcg accccaccga tattgtgatc gaaggcaaac gcggcctgga   25380
```

```
tgctttcgcc accaccgggc tggacctggt gctgcgcaac aatggcatcc agaacctggt    25440
tgtcgcaggt ttcctgacta actgctgcgt tgaaggcacg ttcgatccg gttacgagaa    25500
aggttatgac gtggtgacct tgaccgactg caccgcgaca ttcagtgatg aacaacagcg    25560
cgcagccgag cagtttacgt tgccgatgtt tttcgcaaac cctgcaacac accgcgtttc    25620
tgcaagcact gaacgccgga taaaaaaagc ggcggactcc tgccgagtcg ccgcttttt    25680
agtgcttggg tcattcggtt ggcgcgtact gcatttcgcc gttcccaaac gaccagtctt    25740
cgcgcttcac gtccaccagg ctgatccaca cgtcttcctt gcgcagcccg gtcttggcat    25800
ggatgccgtc ggcgatgaac ttatagaaag ccttttttcac gtcaatgctg cgcccggcgt    25860
tccacgtgac ttggataaac acgatcttgg gtgtgtaagt gacgccaaga tacccggccg    25920
ccgggtaaac cagctcatcc ttggcatggc ggttgatgat ctggaatttg tcgtgctcag    25980
gcacgttggc ccacactggt catcgcggcg tacacgacat caccgatggc cgtcgcggtt    26040
tcagtggaag tgtcggcggc gaggtcgatt cgaactaaag gcatggacaa atccttagtg    26100
atttcagct gaaaatgggc gtgtggctca cacactcgcg ccaaccgggc aacttgcgcc    26160
aggccaacga gttgctggcc cagggagttg ccgacggttt cgctagtgc gccgcgaaac    26220
tcggcatt gacgcatcgg tgaatggctg accggatgtc agtgcttatt gacctgaata    26280
tagactgccg tgcacagacc aatcaaacaa ataccggcga tgtagtaagc ggcgcccatc    26340
tgactgtatt gaagcaatag agtaacgacc atcggcgtca ggccaccgaa tacggcgtac    26400
gacaagttgt aggaaaatga caagccggaa aaccgcacta ccggtggaaa ggcacgcacc    26460
atcacagcag gggctgcgcc tatcgcgccg acaaaaaaac cggtaagtga atagagtgga    26520
accagccatt gcgggtgcgt ttcaagcgtc ttgaacaaga gcagtgcgct gaacagaagc    26580
atgacgctgc cgatcatcaa tacccarccc gcactgaaat gatcggccag tttcccggcg    26640
atcacgcaac caacactcaa rrcacrcaat agcgagactg ttggcctgca aggcttgcgc    26700
tgcag                                                               26705
```

<210> SEQ ID NO 2
<211> LENGTH: 1004
<212> TYPE: PRT
<213> ORGANISM: Pseudomonas fluorescens A2-2

<400> SEQUENCE: 2

Met Leu Leu Glu Val Ala Phe His Val Ile Thr His Leu Ser Thr Ser
1               5                   10                  15

Gln Leu Val Ser Arg Ile Glu Arg Val Val Glu Arg His Ala Ser Leu
            20                  25                  30

Arg Gln Arg Phe Val Met Arg Asn Gly Thr Tyr Trp Ile Glu Gln Ala
        35                  40                  45

Pro Pro Gln Gln Arg Arg Tyr Cys Val Val Arg Thr Tyr Asp Glu Ala
    50                  55                  60

Ser Thr Asp Ala Leu Leu Ala Pro Ser Arg Glu His Ile Gly Val Glu
65                  70                  75                  80

Ser Glu Arg Leu Phe Arg Ala Glu Val Val Glu Arg Ser Asp Gly Gln
                85                  90                  95

Arg Tyr Leu Val Phe Arg Ile His His Ile Ile Ala Asp Leu Trp Ser
            100                 105                 110

Val Gly Leu Leu Ile Arg Asp Phe Ala Glu Asp Cys Met Asp Arg Ser
        115                 120                 125

Ser Ile Thr Leu Ala Ser Arg Pro Ile Ala Pro Leu Ile Asp Pro Glu

-continued

```
            130                 135                 140
Phe Trp Arg His Gln Met Ser Gln Asp Thr Pro Phe Ser Leu Pro Met
145                 150                 155                 160

Ala Ser Leu Glu Gln His Thr Asp Arg Arg Met Val Leu Ser Ser Phe
                165                 170                 175

Val Ile Asp Gln Glu Ser Ser Ala Asp Leu Ala Arg Leu Ala Thr Ala
                180                 185                 190

Cys Ala Val Thr Pro Tyr Thr Val Met Leu Ala Ala Gln Val Leu Ala
                195                 200                 205

Leu Ser Arg Ile Gly Gln Ser Gly Arg Leu Ser Leu Ala Val Thr Phe
210                 215                 220

His Gly Arg Asn Arg Gly Asn Lys Asp Ala Val Gly Tyr Phe Ala Asn
225                 230                 235                 240

Thr Leu Ala Val Pro Phe Asp Val Ser Glu Cys Ser Val Gly Glu Phe
                245                 250                 255

Val Lys Arg Thr Ala Lys Arg Leu Asp Glu Ala Ser Lys Ala Ser Val
                260                 265                 270

Gly Ala Gly Tyr Pro Glu Leu Ala Glu Phe Met Thr Pro Leu Gly Trp
                275                 280                 285

Ala Ala Thr Ala Pro Thr Asn Ala Val Ile Tyr Gln Gln Asp Met Pro
290                 295                 300

Gly Met Pro Arg Gly Leu Ala Ala Ala Leu Leu Gly Leu Gly Thr Val
305                 310                 315                 320

Gln Leu Gly Glu Met Ala Leu Thr Ala Glu Gln Ala Pro Pro Ser Ile
                325                 330                 335

Gly Pro Phe Ala Thr Ala Leu Leu Leu Thr Arg His Asp Gly Lys Leu
                340                 345                 350

His Gly Arg Val Glu Val Asp Pro Ala Gln His Pro Gly Trp Leu Ala
                355                 360                 365

Glu Ala Leu Ala Arg Gln Phe Ala Val Ile Leu Arg Glu Met Val Arg
                370                 375                 380

Asp Pro Gln Ala Arg Leu Ser Ala Leu Pro Ala Cys Leu Leu His Gln
385                 390                 395                 400

Pro Lys Tyr Pro Ser Gln Ala Arg Pro Ala Pro Ala Ser Glu Thr Leu
                405                 410                 415

Val Ala Thr Phe Leu Arg Gln Val Ala Ile Thr Pro Asp Lys Pro Ala
                420                 425                 430

Leu Arg Thr Pro Gln Ala Ser Ile Ser Tyr Ser Glu Leu Ala Ser Arg
                435                 440                 445

Val Ala Arg Leu Ser Ala Ala Leu Arg Val Arg Gly Phe Lys Pro Glu
450                 455                 460

Gln Thr Leu Ala Ile Leu Leu Pro Arg Asp Ile Asn Leu Val Pro Ala
465                 470                 475                 480

Leu Leu Ala Ile Met Ala Cys Gly Gly Ser Tyr Val Pro Leu Ser Asp
                485                 490                 495

Ala Asn Pro Ala Glu Leu Asn Arg Ser Ile Leu Thr Arg Ala Arg Cys
                500                 505                 510

Arg Ala Ile Leu Thr Asp Gln Glu Gly Leu Thr Arg Phe Ala His Leu
                515                 520                 525

Ala Pro Cys Trp Ser Leu Ser Asp Leu Leu Ser Met Pro Asp Ala Pro
                530                 535                 540

Leu Gln Asp Gln Ser Lys Leu Gln Ala Lys Ala Tyr Ile Leu Phe Thr
545                 550                 555                 560
```

```
Ser Gly Ser Thr Gly Glu Pro Lys Gly Val Ala Ile Thr His Ala Asn
            565                 570                 575

Ala Ala Asn Leu Leu Arg Trp Ala Ala Leu Asp Cys Gly Pro Glu Tyr
        580                 585                 590

Leu Ala Gln Thr Leu Ala Ala Thr Pro Thr Thr Phe Asp Leu Ser Ile
    595                 600                 605

Phe Glu Met Phe Ala Pro Leu Met Val Gly Gly Cys Val Gln Pro Val
610                 615                 620

Ser Ser Val Met Ala Leu Ile Asp Asn Pro Ala Leu Leu Lys Gly Thr
625                 630                 635                 640

Thr Leu Ile Asn Thr Val Pro Ser Val Ala Asp Ala Leu Leu Gln His
                645                 650                 655

Asp Val Leu Val Pro Ser Leu Arg Met Leu Asn Leu Ala Gly Glu Pro
                660                 665                 670

Leu Asn Arg Asp Leu Tyr Leu Arg Leu Gln Ala Lys Leu Thr Ala Thr
            675                 680                 685

Arg Ile Val Asn Leu Tyr Gly Pro Thr Glu Thr Thr Thr Tyr Ser Thr
        690                 695                 700

Ala Leu Val Ile Glu Pro Ala Gln Gln Glu Ile Thr Ile Gly Phe Pro
705                 710                 715                 720

Leu Tyr Gly Thr Trp Val Asp Val Asp Gln Asn Met Gln Ser Val
                725                 730                 735

Gly Ile Gly Val Pro Gly Glu Leu Ile Ile His Gly His Gly Val Ala
                740                 745                 750

Gln Gly Tyr Val Ser Asp Pro Val Arg Ser Ala Ala Ser Phe Leu Pro
            755                 760                 765

Ala Ser Asp Gly Leu Arg Cys Tyr Arg Thr Gly Asp Arg Val Arg Trp
        770                 775                 780

Leu Pro Asp Gly Arg Leu Asp Phe Ile Gly Arg Glu Asp Asp Gln Val
785                 790                 795                 800

Lys Val Arg Gly Phe Arg Val Glu Leu Gly Pro Val Gln Ala Ala Leu
                805                 810                 815

His Ala Ile Glu Thr Ile His Glu Ser Ala Val Val Val Pro Lys
                820                 825                 830

Gly Gln Gln Arg Ser Ile Val Ala Phe Ile Val Leu Lys Ala Pro Ser
            835                 840                 845

Glu Asp Glu Ala Val Gln Arg Asn Asn Ile Lys Gln His Leu Leu Gly
        850                 855                 860

Val Leu Pro Tyr Tyr Ala Leu Pro Asp Lys Phe Ile Phe Val Lys Ala
865                 870                 875                 880

Leu Pro Arg Asn Thr His Gly Lys Ile Asp Arg Thr Leu Leu Gln
                885                 890                 895

His Glu Pro Gln Thr Glu Gln Glu Ser Ala Met Arg Asp Ala Thr Asp
                900                 905                 910

Val Glu His Arg Ile Ala Asn Cys Trp Gln Thr Ile Ile Gly His Pro
            915                 920                 925

Val Gln Leu His Glu Asn Phe Leu Asp Ile Gly Gly His Ser Leu Ser
        930                 935                 940

Leu Thr His Leu Thr Gly Leu Leu Arg Lys Glu Phe Asn Ile His Ile
945                 950                 955                 960

Ser Leu His Asp Leu Trp Ile Arg Pro Thr Ile Glu Gln Gln Ala Asp
                965                 970                 975
```

-continued

```
Phe Ile His Lys Leu Gln Asn Ser Val Leu Thr Lys Pro Ala Ala Ala
            980                 985                 990
Pro Ile Pro Arg Leu Asp Arg Lys Ile Ser His His
        995                 1000

<210> SEQ ID NO 3
<211> LENGTH: 1062
<212> TYPE: PRT
<213> ORGANISM: Pseudomonas fluorescens A2-2

<400> SEQUENCE: 3

Met Ser Val Asp Thr Cys Arg Thr Ala Thr Phe Pro Ala Ser Tyr Gly
1               5                   10                  15

Gln Glu Gln Ile Trp Phe Leu Asn Glu Leu Asn Pro His Ser Gln Leu
                20                  25                  30

Ala Tyr Thr Leu Ala Met Lys Val Ser Ile Ala Gly Lys Leu Asn Thr
            35                  40                  45

Leu Arg Leu Gln Arg Ala Val Asn Gln Val Val Ala Ser Gln Glu Ile
    50                  55                  60

Leu Arg Thr Ser Phe Ala Tyr Lys Asn Gln Lys Leu Ser Gln Val Ile
65                  70                  75                  80

Ser Pro Ser Ala Thr Leu Pro Ile Arg Ser Ala His Cys Ile Asp Asp
                85                  90                  95

Val Pro Gly Leu Gln Arg Leu Ile Asn Met Glu Ala Gln Arg Gly Trp
            100                 105                 110

Ser Leu Ser Ser Ala Pro Leu Tyr Arg Leu Leu Leu Ile Lys Thr Gly
        115                 120                 125

Asp Gln Gln His Glu Leu Val Ile Cys Thr His His Ile Val Cys Asp
    130                 135                 140

Gly Ile Ser Leu Gln Leu Leu Leu Gln Lys Ile Val Ser Ala Tyr Gln
145                 150                 155                 160

Gly Gln Ser Asp Gly Arg Val Leu Thr Ser Pro Asp Glu Glu Thr Leu
                165                 170                 175

Gln Phe Val Asp Tyr Ala Ala Trp Ser Arg Gln His Glu Tyr Ala Gly
            180                 185                 190

Leu Glu Tyr Trp Arg Gln Gln Leu Ala Asp Ala Pro Thr Ile Leu Asp
        195                 200                 205

Ile Ser Thr Lys Thr Gly Arg Ser Glu Gln Gln Thr Phe Leu Gly Ala
    210                 215                 220

Arg Ile Pro Val Glu Phe Ser His His Gln Trp Gln Ala Leu Arg Gln
225                 230                 235                 240

Ile Phe Arg Pro Gln Gly Ile Ser Cys Ala Ala Val Phe Leu Ala Ala
                245                 250                 255

Tyr Cys Val Val Leu His Arg Leu Ala Glu Gln Asp Asp Ile Leu Ile
            260                 265                 270

Gly Leu Pro Thr Ser Asn Arg Leu Arg Pro Glu Leu Ala Gln Val Ile
        275                 280                 285

Gly Tyr Leu Ser Asn Leu Cys Val Phe Arg Ser Gln Tyr Ala His Asp
    290                 295                 300

Gln Ser Val Thr Asp Phe Leu Gln Gln Val Gln Leu Thr Leu Pro Asn
305                 310                 315                 320

Leu Ile Glu His Gly Glu Thr Pro Phe Gln Gln Val Leu Glu Ser Val
                325                 330                 335

Glu His Thr Arg Gln Ala Gly Val Thr Pro Leu Cys Gln Val Leu Phe
            340                 345                 350
```

```
Gly Tyr Glu Gln Asp Val Arg Arg Thr Leu Asp Ile Gly Asp Leu Gln
            355                 360                 365

Leu Thr Val Ser Asp Val Asp Thr Gly Ala Ala Arg Leu Asp Leu Ser
        370                 375                 380

Leu Phe Leu Phe Glu Asp Glu Leu Asn Val Cys Gly Phe Leu Glu Tyr
385                 390                 395                 400

Ala Thr Asp Arg Ile Asp Ala Ser Ala Gln Asn Met Val Arg Met
                405                 410                 415

Leu Ser Ser Val Leu Arg Glu Phe Val Ala Ala Pro Gln Ala Pro Leu
            420                 425                 430

Ser Glu Val Gln Leu Gly Ala Ala Asp Ser Gln Ala Gln Thr Pro Ala
            435                 440                 445

Ile Ala Pro Ala Phe Pro Ser Val Pro Ala Arg Leu Phe Ala Leu Ala
        450                 455                 460

Asp Ser His Pro Asn Ala Thr Ala Leu Arg Asp Glu Gln Gly Glu Leu
465                 470                 475                 480

Thr Tyr Ala Gln Val Cys Gln Gln Ile Leu Gln Ala Ala Ala Thr Leu
                485                 490                 495

Arg Ala Gln Gly Ala Lys Pro Gly Thr Leu Ile Ala Val Ile Gly Glu
            500                 505                 510

Arg Gly Asn Pro Trp Leu Ile Ala Met Leu Ala Ile Trp Gln Val Gly
            515                 520                 525

Gly Ile Tyr Val Pro Leu Ser Lys Asp Leu Pro Glu Gln Arg Leu Gln
        530                 535                 540

Gly Ile Leu Ala Glu Leu Glu Gly Ala Ile Leu Ile Thr Asp Asp Thr
545                 550                 555                 560

Thr Pro Glu Arg Phe Arg Gln Arg Val Thr Leu Pro Met His Ala Leu
                565                 570                 575

Trp Ala Asp Gly Ala Thr His His Glu Arg Gln Thr Thr Asp Ala Ser
            580                 585                 590

Arg Leu Ser Gly Tyr Met Met Tyr Thr Ser Gly Ser Thr Gly Lys Pro
            595                 600                 605

Lys Gly Val His Val Ser Gln Ala Asn Leu Val Ala Thr Leu Ser Ala
        610                 615                 620

Phe Gly Gln Leu Leu Gln Val Lys Pro Ser Asp Arg Met Leu Ala Leu
625                 630                 635                 640

Thr Thr Phe Ser Phe Asp Ile Ser Leu Leu Glu Leu Leu Leu Pro Leu
                645                 650                 655

Val Gln Gly Ala Ser Val Gln Ile Ala Val Ala Gln Ala Gln Arg Asp
            660                 665                 670

Ala Glu Lys Leu Ala Gly Tyr Leu Ala Asp Pro Arg Ile Thr Leu Val
        675                 680                 685

Gln Ala Thr Pro Val Thr Trp Arg Leu Leu Ser Thr Gly Trp Gln
        690                 695                 700

Pro Arg Glu Ser Leu Thr Leu Leu Cys Gly Gly Glu Ala Leu Pro Gln
705                 710                 715                 720

Asp Leu Ala Asp Arg Leu Cys Leu Pro Gly Met Thr Leu Trp Asn Leu
                725                 730                 735

Tyr Gly Pro Thr Glu Thr Thr Ile Trp Ser Thr Ala Cys Arg Leu Gln
            740                 745                 750

Pro Gly Ala Pro Val Gln Leu Gly His Pro Ile Ala Gly Thr Gln Ile
        755                 760                 765
```

Ala Leu Val Asp Arg Asn Leu Arg Ser Val Pro Arg Gly Val Ile Gly
770                 775                 780

Glu Leu Leu Ile Cys Gly Pro Gly Val Ser Gln Gly Tyr Tyr Arg Asn
785                 790                 795                 800

Pro Val Glu Thr Ala Lys Arg Phe Val Pro Asp Pro His Gly Ser Gly
            805                 810                 815

Lys Arg Ala Tyr Leu Thr Gly Asp Arg Met Arg Met Gln Gln Asp Gly
            820                 825                 830

Ser Leu Ala Tyr Ile Gly Arg Arg Asp Asp Gln Ile Lys Leu Arg Gly
            835                 840                 845

His Arg Ile Glu Leu Gly Glu Ile Glu Thr Ala Leu Arg Lys Leu Pro
850                 855                 860

Gly Val Arg Asp Ala Ala Ala Gln Leu His Asp Gln Asp Pro Ser Arg
865                 870                 875                 880

Gly Ile Gln Ala Phe Val Gln Leu Cys Ala Thr Val Asp Glu Ser Leu
            885                 890                 895

Ile Asp Ile Gly Gln Trp Leu Glu Thr Leu Arg Gln Thr Leu Pro Glu
            900                 905                 910

Ala Trp Leu Pro Thr Glu Tyr Tyr Arg Ile Asp Gly Ile Pro Leu Thr
            915                 920                 925

Tyr Asn Gly Lys Arg Asp Arg Lys Arg Leu Leu His Gln Ala Val Arg
930                 935                 940

Leu Gln Thr Leu Ser Leu Arg Val Ala Pro Ser Ser Asp Thr Glu Thr
945                 950                 955                 960

Arg Val Gln Gln Ile Trp Cys Glu Leu Leu Gly Leu Glu Asp Ile Gly
            965                 970                 975

Val Thr Asp Asp Phe Phe Gln Leu Gly Gly His Ser Ile Leu Val Ala
            980                 985                 990

Arg Met Val Glu Arg Ile Glu Thr Ala Phe Gly Arg Arg Val Pro Ile
            995                 1000                1005

Ala Asp Ile Tyr Phe Ser Pro Thr Ile Ala Arg Val Ala Ala Thr Leu
    1010                1015                1020

Asp Ser Met Thr Phe Glu Gln Gly Leu Ala Ala His Ser Val Lys Gly
1025                1030                1035                1040

Asp Trp Glu Phe Thr Ala Ile Ser Leu Gln His Asn Ala Asp Ser Thr
            1045                1050                1055

Ala Ala Ala Gln Glu Arg
            1060

<210> SEQ ID NO 4
<211> LENGTH: 1432
<212> TYPE: PRT
<213> ORGANISM: Pseudomonas fluorescens A2-2

<400> SEQUENCE: 4

Met His Ser Pro Thr Ile Asp Thr Phe Glu Ala Ala Leu Arg Ser Leu
1               5                   10                  15

Pro Ala Ala Arg Asp Ala Leu Gly Ala Tyr Pro Leu Ser Ser Glu Gln
                20                  25                  30

Lys Arg Leu Trp Leu Leu Ala Gln Leu Ala Gly Thr Ala Thr Leu Pro
            35                  40                  45

Val Thr Val Arg Tyr Ala Phe Thr Gly Thr Val Asp Leu Ala Val Val
    50                  55                  60

Gln Gln Asn Leu Ser Ala Trp Ile Ala His Ser Glu Ser Leu Arg Ser
65                  70                  75                  80

-continued

```
Leu Phe Val Glu Val Leu Glu Arg Pro Val Arg Leu Met Pro Thr
                85                  90                  95

Gly Leu Val Lys Leu Glu Tyr Phe Asp Arg Pro Ser Asp Ala Asp
            100                 105                 110

Met Ala Glu Leu Ile Gly Ala Ala Phe Glu Leu Asp Lys Gly Pro Leu
        115                 120                 125

Leu Arg Ala Phe Ile Thr Arg Thr Ala Ala Gln Gln His Glu Leu His
130                 135                 140

Leu Val Gly His Pro Ile Val Asp Glu Pro Ser Leu Gln Arg Ile
145                 150                 155                 160

Ala Gln Thr Leu Phe Gln Thr Glu Pro Asp His Gln Tyr Pro Ala Val
                165                 170                 175

Gly Ala Ile Ala Glu Val Phe Gln Arg Glu Gln Thr Leu Ala Gln Asp
            180                 185                 190

Ala Gln Ile Thr Glu Gln Trp Gln Gln Trp Gly Ile Gly Leu Gln Ala
        195                 200                 205

Pro Ala Ala Thr Glu Ile Pro Thr Glu Asn Pro Arg Pro Ala Ile Lys
    210                 215                 220

Gly Ser Asp Arg Gln Val His Glu Ala Leu Thr Ala Trp Gly Asp Gln
225                 230                 235                 240

Pro Val Ala Glu Ala Glu Ile Val Ser Ser Trp Leu Thr Val Leu Met
                245                 250                 255

Arg Trp Gln Gly Ser Gln Ser Ala Leu Cys Ala Ile Lys Val Arg Asp
            260                 265                 270

Lys Ala His Ala Asn Leu Ile Gly Pro Leu Gln Thr Tyr Leu Pro Val
        275                 280                 285

Arg Val Asp Met Pro Asp Gly Ser Thr Leu Ala Gln Leu Arg Leu Gln
    290                 295                 300

Val Glu Glu Gln Leu Asn Gly Asn Asp His Pro Ser Phe Ser Thr Leu
305                 310                 315                 320

Leu Glu Val Cys Pro Pro Lys Arg Asp Leu Ser Arg Thr Pro Tyr Phe
                325                 330                 335

Gln Thr Gly Leu Gln Phe Ile Ala His Asp Val Glu Gln Arg Asp Phe
            340                 345                 350

His Ala Gly Asn Leu Thr Arg Leu Pro Thr Lys Gln Pro Ser Ser Asp
        355                 360                 365

Leu Asp Leu Phe Ile Ser Cys Trp Val Ser Asp Gly Thr Leu Gly Leu
    370                 375                 380

Thr Leu Asp Tyr Asp Cys Ala Val Leu Asn Ser Ser Gln Val Glu Val
385                 390                 395                 400

Leu Ala Gln Ala Leu Ile Ser Val Leu Ser Ala Pro Gly Glu Gln Pro
                405                 410                 415

Ile Ala Thr Val Ala Leu Met Gly Gln Gln Met Gln Gln Thr Val Leu
            420                 425                 430

Ala Gln Ala His Gly Pro Arg Thr Thr Pro Pro Gln Leu Thr Leu Thr
        435                 440                 445

Glu Trp Val Ala Ala Ser Thr Glu Lys Ser Pro Leu Ala Val Ala Val
    450                 455                 460

Ile Asp His Gly Gln Gln Leu Ser Tyr Ala Glu Leu Trp Ala Arg Ala
465                 470                 475                 480

Ala Leu Val Ala Ala Asn Ile Ser Gln His Val Ala Lys Pro Arg Ser
                485                 490                 495
```

-continued

```
Ile Ile Ala Val Ala Leu Pro Arg Ser Ala Glu Phe Ile Ala Ala Leu
            500                 505                 510

Leu Gly Val Val Arg Ala Gly His Ala Phe Leu Pro Ile Asp Pro Arg
        515                 520                 525

Leu Pro Thr Asp Arg Ile Gln Phe Leu Ile Glu Asn Ser Gly Cys Glu
    530                 535                 540

Leu Val Ile Thr Ser Asp Gln Gln Ser Val Glu Gly Trp Pro Gln Val
545                 550                 555                 560

Ala Arg Ile Arg Met Glu Ala Leu Asp Pro Asp Ile Arg Trp Val Ala
                565                 570                 575

Pro Thr Gly Leu Ser His Ser Asp Ala Ala Tyr Leu Ile Tyr Thr Ser
            580                 585                 590

Gly Ser Thr Gly Val Pro Lys Gly Val Val Glu His Arg Gln Val
        595                 600                 605

Val Asn Asn Ile Leu Trp Arg Gln Arg Thr Trp Pro Leu Thr Ala Gln
    610                 615                 620

Asp Asn Val Leu His Asn His Ser Phe Ser Phe Asp Pro Ser Val Trp
625                 630                 635                 640

Ala Leu Phe Trp Pro Leu Leu Thr Gly Gly Thr Ile Val Leu Ala Asp
                645                 650                 655

Val Arg Thr Met Glu Asp Ser Thr Ala Leu Leu Asp Leu Met Ile Arg
            660                 665                 670

His Asp Val Ser Val Leu Gly Gly Val Pro Ser Leu Leu Gly Thr Leu
        675                 680                 685

Ile Asp His Pro Phe Ala Asn Asp Cys Arg Ala Val Lys Leu Val Leu
    690                 695                 700

Ser Gly Gly Glu Val Leu Asn Pro Glu Leu Ala His Lys Ile Gln Lys
705                 710                 715                 720

Val Trp Gln Ala Asp Val Ala Asn Leu Tyr Gly Pro Thr Glu Ala Thr
                725                 730                 735

Ile Asp Ala Leu Tyr Phe Ser Ile Asp Lys Asn Ala Ala Gly Ala Ile
            740                 745                 750

Pro Ile Gly Tyr Pro Ile Asp Asn Thr Asp Ala Tyr Ile Val Asp Leu
        755                 760                 765

Asn Leu Asn Pro Val Pro Pro Gly Val Pro Gly Glu Ile Met Leu Ala
    770                 775                 780

Gly Gln Asn Leu Ala Arg Gly Tyr Leu Gly Lys Pro Ala Gln Thr Ala
785                 790                 795                 800

Gln Arg Phe Leu Pro Asn Pro Phe Gly Asn Gly Arg Val Tyr Ala Thr
                805                 810                 815

Gly Asp Leu Gly Arg Arg Trp Ser Ser Gly Ala Ile Ser Tyr Leu Gly
            820                 825                 830

Arg Arg Asp Gln Gln Val Lys Ile Arg Gly His Arg Ile Glu Leu Asn
        835                 840                 845

Glu Val Ala His Leu Leu Cys Gln Ala Leu Glu Leu Lys Glu Ala Ile
    850                 855                 860

Val Phe Ala Gln His Ala Gly Thr Glu Gln Ala Arg Leu Val Ala Ala
865                 870                 875                 880

Ile Glu Gln Gln Pro Gly Leu His Ser Glu Gly Ile Lys Gln Glu Leu
                885                 890                 895

Leu Arg His Leu Pro Ala Tyr Leu Ile Pro Ser Gln Leu Leu Leu Leu
            900                 905                 910

Asp Glu Leu Pro Arg Thr Ala Thr Gly Lys Val Asp Met Leu Lys Leu
```

-continued

```
            915                 920                 925
Asp Gln Leu Ala Ala Pro Gln Leu Asn Asp Ala Gly Gly Thr Glu Cys
    930                 935                 940

Arg Ala Pro Arg Thr Asp Leu Glu Gln Ser Val Met Thr Asp Phe Ala
945                 950                 955                 960

Gln Val Leu Gly Leu Thr Ala Val Thr Pro Asp Thr Asp Phe Phe Glu
                965                 970                 975

Gln Gly Gly Asn Ser Ile Leu Leu Thr Arg Leu Ala Gly Thr Leu Ser
            980                 985                 990

Ala Lys Tyr Gln Val Gln Ile Pro Leu His Glu Phe Phe Leu Thr Pro
        995                 1000                1005

Thr Pro Ala Ala Val Ala Gln Ala Ile Glu Ile Tyr Arg Arg Glu Gly
    1010                1015                1020

Leu Thr Ala Leu Leu Ser Arg Gln His Ala Gln Thr Leu Glu Gln Asp
1025                1030                1035                1040

Ile Tyr Leu Glu Glu His Ile Arg Pro Asp Gly Leu Pro His Ala Asn
                1045                1050                1055

Trp Tyr Gln Pro Ser Val Val Phe Leu Thr Gly Ala Thr Gly Tyr Leu
            1060                1065                1070

Gly Leu Tyr Leu Ile Glu Gln Leu Leu Lys Arg Thr Thr Ser Arg Val
        1075                1080                1085

Ile Cys Leu Cys Arg Ala Lys Asp Ala Glu His Ala Lys Ala Arg Ile
    1090                1095                1100

Leu Glu Gly Leu Lys Thr Tyr Arg Ile Asp Val Gly Ser Glu Leu His
1105                1110                1115                1120

Arg Val Glu Tyr Leu Thr Gly Asp Leu Ala Leu Pro His Leu Gly Leu
                1125                1130                1135

Ser Glu His Gln Trp Gln Thr Leu Ala Glu Glu Val Asp Val Ile Tyr
            1140                1145                1150

His Asn Gly Ala Leu Val Asn Phe Val Tyr Pro Tyr Ser Ala Leu Lys
        1155                1160                1165

Ala Thr Asn Val Gly Gly Thr Gln Ala Ile Leu Glu Leu Ala Cys Thr
    1170                1175                1180

Ala Arg Leu Lys Ser Val Gln Tyr Val Ser Thr Val Asp Thr Leu Leu
1185                1190                1195                1200

Ala Thr His Val Pro Arg Pro Phe Ile Glu Asp Asp Ala Pro Leu Arg
                1205                1210                1215

Ser Ala Val Gly Val Pro Val Gly Tyr Thr Gly Ser Lys Trp Val Ala
            1220                1225                1230

Glu Gly Val Ala Asn Leu Gly Leu Arg Arg Gly Ile Pro Val Ser Ile
        1235                1240                1245

Phe Arg Pro Gly Leu Ile Leu Gly His Thr Glu Thr Gly Ala Ser Gln
    1250                1255                1260

Ser Ile Asp Tyr Leu Leu Val Ala Leu Arg Gly Phe Leu Pro Met Gly
1265                1270                1275                1280

Ile Val Pro Asp Tyr Pro Arg Ile Phe Asp Ile Val Pro Val Asp Tyr
                1285                1290                1295

Val Ala Ala Ala Ile Val His Ile Ser Met Gln Pro Gln Gly Arg Asp
            1300                1305                1310

Lys Phe Phe His Leu Phe Asn Pro Ala Pro Val Thr Ile Arg Gln Phe
        1315                1320                1325

Cys Asp Trp Ile Arg Glu Phe Gly Tyr Glu Phe Lys Leu Val Asp Phe
    1330                1335                1340
```

Glu His Gly Arg Gln Gln Ala Leu Ser Val Pro Pro Gly His Leu Leu
1345                1350                1355                1360

Tyr Pro Leu Val Pro Leu Ile Arg Asp Ala Asp Pro Leu Pro His Arg
            1365                1370                1375

Ala Leu Asp Pro Asp Tyr Ile His Glu Val Asn Pro Ala Leu Glu Cys
        1380                1385                1390

Lys Gln Thr Leu Glu Leu Leu Ala Ser Ser Asp Ile Thr Leu Ser Lys
    1395                1400                1405

Thr Thr Lys Ala Tyr Ala His Thr Ile Leu Arg Tyr Leu Ile Asp Thr
  1410                1415                1420

Gly Phe Met Ala Lys Pro Gly Val
1425                1430

<210> SEQ ID NO 5
<211> LENGTH: 350
<212> TYPE: PRT
<213> ORGANISM: Pseudomonas fluorescens A2-2

<400> SEQUENCE: 5

Met Glu Ser Ile Ala Phe Pro Ile Ala His Lys Pro Phe Ile Leu Gly
 1               5                  10                  15

Cys Pro Glu Asn Leu Pro Ala Thr Glu Arg Ala Leu Ala Pro Ser Ala
            20                  25                  30

Ala Met Ala Arg Gln Val Leu Glu Tyr Leu Glu Ala Cys Pro Gln Ala
        35                  40                  45

Lys Asn Leu Glu Gln Tyr Leu Gly Thr Leu Arg Glu Val Leu Ala His
    50                  55                  60

Leu Pro Cys Ala Ser Thr Gly Leu Met Thr Asp Asp Pro Arg Glu Asn
65                  70                  75                  80

Gln Glu Asn Arg Asp Asn Asp Phe Ala Phe Gly Ile Glu Arg His Gln
                85                  90                  95

Gly Asp Thr Val Thr Leu Met Val Lys Ala Thr Leu Asp Ala Ala Ile
            100                 105                 110

Gln Thr Gly Glu Leu Val Gln Arg Ser Gly Thr Ser Leu Asp His Ser
        115                 120                 125

Glu Trp Ser Asp Met Met Ser Val Ala Gln Val Ile Leu Gln Thr Ile
    130                 135                 140

Ala Asp Pro Arg Val Met Pro Glu Ser Arg Leu Thr Phe Gln Ala Pro
145                 150                 155                 160

Lys Ser Lys Val Glu Glu Asp Asp Gln Asp Pro Leu Arg Arg Trp Val
                165                 170                 175

Arg Gly His Leu Leu Phe Met Val Leu Cys Gln Gly Met Ser Leu Cys
            180                 185                 190

Thr Asn Leu Leu Ile Ser Ala Ala His Asp Lys Asp Leu Glu Leu Ala
        195                 200                 205

Cys Ala Gln Ala Asn Arg Leu Ile Gln Leu Met Asn Ile Ser Arg Ile
    210                 215                 220

Thr Leu Glu Phe Ala Thr Asp Leu Asn Ser Gln Gln Tyr Val Ser Gln
225                 230                 235                 240

Ile Arg Pro Thr Leu Met Pro Ala Ile Ala Pro Pro Lys Met Ser Gly
                245                 250                 255

Ile Asn Trp Arg Asp His Val Val Met Ile Arg Trp Met Arg Gln Ser
            260                 265                 270

Thr Asp Ala Trp Asn Phe Ile Glu Gln Ala Tyr Pro Gln Leu Ala Glu

```
                275                 280                 285
Arg Met Arg Thr Thr Leu Ala Gln Val Tyr Ser Ala His Arg Gly Val
    290                 295                 300

Cys Glu Lys Phe Val Gly Glu Asn Thr Ser Leu Leu Ala Lys Glu
305                 310                 315                 320

Asn Ala Thr Asn Thr Ala Gly Gln Val Leu Glu Asn Leu Lys Lys Ser
                325                 330                 335

Arg Leu Lys Tyr Leu Lys Thr Lys Gly Cys Ala Gly Ala Gly
            340                 345                 350

<210> SEQ ID NO 6
<211> LENGTH: 61
<212> TYPE: PRT
<213> ORGANISM: Pseudomonas fluorescens A2-2

<400> SEQUENCE: 6

Met Pro Thr Phe Leu Gly Asp Asp Ala Pro Cys Val Val Val
1               5                   10                  15

Val Asn Ala Asp Lys His Tyr Ser Ile Trp Pro Ser Ala Arg Asp Ile
                20                  25                  30

Pro Ser Gly Trp Ser Glu Glu Gly Phe Lys Gly Ser Arg Ser Asp Cys
            35                  40                  45

Leu Glu His Ile Ala Gln Ile Trp Pro Glu Pro Thr Ala
        50                  55                  60

<210> SEQ ID NO 7
<211> LENGTH: 355
<212> TYPE: PRT
<213> ORGANISM: Pseudomonas fluorescens A2-2

<400> SEQUENCE: 7

Met Thr Ser Thr His Arg Thr Thr Asp Gln Val Lys Pro Ala Val Leu
1               5                   10                  15

Asp Met Pro Gly Leu Ser Gly Ile Leu Phe Gly His Ala Ala Phe Gln
                20                  25                  30

Tyr Leu Arg Ala Ser Cys Glu Leu Asp Leu Phe Glu His Val Arg Asp
            35                  40                  45

Leu Arg Glu Ala Thr Lys Glu Ser Ile Ser Ser Arg Leu Lys Leu Gln
        50                  55                  60

Glu Arg Ala Ala Asp Ile Leu Leu Gly Ala Thr Ser Leu Gly Met
65                  70                  75                  80

Leu Val Lys Glu Asn Gly Ile Tyr Arg Asn Ala Asp Val Val Glu Asp
                85                  90                  95

Leu Met Ala Thr Asp Asp Trp Gln Arg Phe Lys Asp Thr Val Ala Phe
            100                 105                 110

Glu Asn Tyr Ile Val Tyr Glu Gly Gln Leu Asp Phe Thr Glu Ser Leu
        115                 120                 125

Gln Lys Asn Thr Asn Val Gly Leu Gln Arg Phe Pro Gly Glu Gly Arg
    130                 135                 140

Asp Leu Tyr His Arg Leu His Gln Asn Pro Lys Leu Glu Asn Val Phe
145                 150                 155                 160

Tyr Arg Tyr Met Arg Ser Trp Ser Glu Leu Ala Asn Gln Asp Leu Val
                165                 170                 175

Lys His Leu Asp Leu Ser Arg Val Lys Lys Leu Leu Asp Ala Gly Gly
            180                 185                 190

Gly Asp Ala Val Asn Ala Ile Ala Leu Ala Lys His Asn Glu Gln Leu
```

-continued

```
                195                 200                 205
Asn Val Thr Val Leu Asp Ile Asp Asn Ser Ile Pro Val Thr Gln Gly
            210                 215                 220
Lys Ile Asn Asp Ser Gly Leu Ser His Arg Val Lys Ala Gln Ala Leu
225                 230                 235                 240
Asp Ile Leu His Gln Ser Phe Pro Glu Gly Tyr Asp Cys Ile Leu Phe
                245                 250                 255
Ala His Gln Leu Val Ile Trp Thr Leu Glu Glu Asn Thr His Met Leu
            260                 265                 270
Arg Lys Ala Tyr Asp Ala Leu Pro Glu Gly Gly Arg Val Val Ile Phe
        275                 280                 285
Asn Ser Met Ser Asn Asp Glu Gly Asp Gly Pro Val Met Ala Ala Leu
290                 295                 300
Asp Ser Val Tyr Phe Ala Cys Leu Pro Ala Glu Gly Met Ile Tyr
305                 310                 315                 320
Ser Trp Lys Gln Tyr Glu Val Cys Leu Ala Glu Ala Gly Phe Lys Asn
                325                 330                 335
Pro Val Arg Thr Ala Ile Pro Gly Trp Thr Pro His Gly Ile Ile Val
            340                 345                 350
Ala Tyr Lys
        355

<210> SEQ ID NO 8
<211> LENGTH: 347
<212> TYPE: PRT
<213> ORGANISM: Pseudomonas fluorescens A2-2

<400> SEQUENCE: 8

Met Ala Arg Ser Pro Glu Thr Asn Ser Ala Met Pro Gln Gln Ile Arg
1               5                   10                  15
Gln Leu Leu Tyr Ser Gln Leu Ile Ser Gln Ser Ile Gln Thr Phe Cys
            20                  25                  30
Glu Leu Arg Leu Pro Asp Val Leu Gln Ala Ala Gly Gln Pro Thr Ser
        35                  40                  45
Ile Glu Arg Leu Ala Glu Gln Thr His Thr His Ile Ser Ala Leu Ser
    50                  55                  60
Arg Leu Leu Lys Ala Leu Lys Pro Phe Gly Leu Val Lys Glu Thr Asp
65                  70                  75                  80
Glu Gly Phe Ser Leu Thr Asp Leu Gly Ala Ser Leu Thr His Asp Ala
                85                  90                  95
Phe Ala Ser Ala Gln Pro Ser Ala Leu Leu Ile Asn Gly Glu Met Gly
            100                 105                 110
Gln Ala Trp Arg Gly Met Ala Gln Thr Ile Arg Thr Gly Glu Ser Ser
        115                 120                 125
Phe Lys Met Tyr Tyr Gly Ile Ser Leu Phe Glu Tyr Phe Glu Gln His
    130                 135                 140
Pro Glu Arg Arg Ala Ile Phe Asp Arg Ser Gln Asp Met Gly Leu Asp
145                 150                 155                 160
Leu Glu Ile Pro Glu Ile Leu Glu Asn Ile Asn Leu Asn Asp Gly Glu
                165                 170                 175
Asn Ile Val Asp Val Gly Gly Gly Ser Gly His Leu Leu Met His Met
            180                 185                 190
Leu Asp Lys Trp Pro Glu Ser Thr Gly Ile Leu Phe Asp Leu Pro Val
        195                 200                 205
```

```
Ala Ala Lys Ile Ala Gln Gln His Leu His Lys Ser Gly Lys Ala Gly
    210                 215                 220

Cys Phe Glu Ile Val Ala Gly Asp Phe Phe Lys Ser Leu Pro Asp Ser
225                 230                 235                 240

Gly Ser Val Tyr Leu Leu Ser His Val Leu His Asp Trp Gly Asp Glu
                245                 250                 255

Asp Cys Lys Ala Ile Leu Ala Thr Cys Arg Arg Ser Met Pro Asp Asn
            260                 265                 270

Ala Leu Leu Val Val Val Asp Leu Val Ile Asp Gln Ser Glu Ser Ala
        275                 280                 285

Gln Pro Asn Pro Thr Gly Ala Met Met Asp Leu Tyr Met Leu Ser Leu
    290                 295                 300

Phe Gly Ile Ala Gly Gly Lys Glu Arg Asn Glu Asp Glu Phe Arg Thr
305                 310                 315                 320

Leu Ile Glu Asn Ser Gly Phe Asn Val Lys Gln Val Lys Arg Leu Pro
                325                 330                 335

Ser Gly Asn Gly Ile Ile Phe Ala Tyr Pro Lys
            340                 345

<210> SEQ ID NO 9
<211> LENGTH: 180
<212> TYPE: PRT
<213> ORGANISM: Pseudomonas fluorescens A2-2

<400> SEQUENCE: 9

Met Ser Thr Leu Val Tyr Tyr Val Ala Ala Thr Leu Asp Gly Tyr Ile
1               5                   10                  15

Ala Thr Gln Gln His Lys Leu Asp Trp Leu Glu Asn Phe Ala Leu Gly
            20                  25                  30

Asp Asp Ala Thr Ala Tyr Asp Asp Phe Tyr Gln Thr Ile Gly Ala Val
        35                  40                  45

Val Met Gly Ser Gln Thr Tyr Glu Trp Ile Met Ser Asn Ala Pro Asp
    50                  55                  60

Asp Trp Pro Tyr Gln Asp Val Pro Ala Phe Val Met Ser Asn Arg Asp
65                  70                  75                  80

Leu Ser Ala Pro Ala Asn Leu Asp Ile Thr Phe Leu Arg Gly Asp Ala
                85                  90                  95

Ser Ala Ile Ala Val Arg Ala Arg Gln Ala Ala Lys Gly Lys Asn Val
            100                 105                 110

Trp Leu Val Gly Gly Lys Thr Ala Ala Cys Phe Ala Asn Ala Gly
        115                 120                 125

Glu Leu Gln Gln Leu Phe Ile Thr Thr Ile Pro Thr Phe Ile Gly Thr
    130                 135                 140

Gly Val Pro Val Leu Pro Val Asp Arg Ala Leu Glu Val Val Leu Arg
145                 150                 155                 160

Glu Gln Arg Thr Leu Gln Ser Gly Ala Met Glu Cys Ile Leu Asp Val
                165                 170                 175

Lys Lys Ala Asp
            180

<210> SEQ ID NO 10
<211> LENGTH: 220
<212> TYPE: PRT
<213> ORGANISM: Pseudomonas fluorescens A2-2

<400> SEQUENCE: 10
```

```
Met Ser Asn Val Phe Ser Gly Gly Lys Gly Asn Gly Asn Pro Gly Phe
1               5                   10                  15

Val Arg Thr Phe Ser Arg Ile Ala Pro Thr Tyr Glu Glu Lys Tyr Gly
            20                  25                  30

Thr Lys Leu Ser Gln Ala His Asp Asp Cys Leu Arg Met Leu Ser Arg
        35                  40                  45

Trp Met Cys Thr Ser Arg Pro Glu Arg Val Leu Asp Ile Gly Cys Gly
    50                  55                  60

Thr Gly Ala Leu Ile Glu Arg Met Phe Ala Leu Trp Pro Glu Ala Arg
65                  70                  75                  80

Phe Glu Gly Val Asp Pro Ala Gln Gly Met Val Asp Glu Ala Ala Lys
                85                  90                  95

Arg Arg Pro Phe Ala Ser Phe Val Lys Gly Val Ala Glu Ala Leu Pro
                100                 105                 110

Phe Pro Ser Gln Ser Met Asp Leu Val Val Cys Ser Met Ser Phe Gly
            115                 120                 125

His Trp Ala Asp Lys Ser Val Ser Leu Asn Glu Val Arg Arg Val Leu
        130                 135                 140

Lys Pro Gln Gly Leu Phe Cys Leu Val Glu Asn Leu Pro Ala Gly Trp
145                 150                 155                 160

Gly Leu Thr Thr Leu Ile Asn Trp Leu Leu Gly Ser Leu Ala Asp Tyr
                165                 170                 175

Arg Ser Glu His Glu Val Ile Gln Leu Ala Gln Thr Ala Gly Leu Gln
                180                 185                 190

Ser Met Glu Thr Ser Val Thr Asp Gln His Val Ile Ala Thr Phe
            195                 200                 205

Arg Pro Cys Cys Gly Glu Val Gly Asp His Gly Arg
210                 215                 220

<210> SEQ ID NO 11
<211> LENGTH: 509
<212> TYPE: PRT
<213> ORGANISM: Pseudomonas fluorescens A2-2

<400> SEQUENCE: 11

Met Val Val Lys Asn Lys Gln Val Leu Val Val Gly Ala Gly Pro Val
1               5                   10                  15

Gly Leu Ala Val Ala Ala Ala Leu Ala Glu Leu Gly Ile Ala Val Asp
            20                  25                  30

Leu Ile Asp Lys Arg Pro Ala Ala Ser Pro His Ser Arg Ala Phe Gly
        35                  40                  45

Leu Glu Pro Val Thr Leu Glu Leu Leu Asn Ala Trp Gly Val Ala Asp
    50                  55                  60

Glu Met Ile Arg Arg Gly Ile Val Trp Ala Ser Ala Pro Leu Gly Asp
65                  70                  75                  80

Lys Ala Gly Arg Thr Leu Ser Phe Ser Lys Leu Pro Cys Glu Tyr Pro
                85                  90                  95

His Met Val Ile Ile Pro Gln Ser Gln Thr Glu Ser Val Leu Thr Asp
                100                 105                 110

Trp Val Asn Arg Lys Gly Val Asn Leu Lys Arg Gly Tyr Ala Leu Lys
            115                 120                 125

Ala Leu Asp Ala Gly Asp Leu His Val Glu Val Thr Leu Glu His Ser
        130                 135                 140

Glu Thr Gly Ser Val Gln Gln Ser Arg Tyr Asp Trp Val Leu Gly Ala
145                 150                 155                 160
```

Asp Gly Val Asn Ser Val Arg Gln Leu Leu Asn Ile Ser Phe Val
            165                 170                 175

Gly Gln Asp Tyr Lys His Ser Leu Val Val Ala Asp Val Val Leu Arg
            180                 185                 190

Asn Pro Pro Ser Pro Ala Val His Ala Arg Ser Val Ser Arg Gly Leu
            195                 200                 205

Val Ala Leu Phe Pro Leu Pro Asp Gly Ser Tyr Arg Val Ser Ile Glu
            210                 215                 220

Asp Asn Glu Arg Met Asp Thr Pro Val Lys Gln Pro Val Thr His Glu
225                 230                 235                 240

Glu Ile Ala Gly Gly Met Lys Asp Ile Leu Gly Thr Asp Phe Gly Leu
                    245                 250                 255

Ala Gln Val Leu Trp Ser Ala Arg Tyr Arg Ser Gln Gln Arg Leu Ala
                260                 265                 270

Thr His Tyr Arg Gln Gly Arg Val Phe Leu Leu Gly Asp Ala Ala His
            275                 280                 285

Thr His Val Pro Ala Gly Gly Gln Gly Leu Gln Met Gly Ile Gly Asp
            290                 295                 300

Ala Ala Asn Leu Ala Trp Lys Leu Ala Gly Val Ile Gln Ala Thr Leu
305                 310                 315                 320

Pro Met Asp Leu Leu Glu Ser Tyr Glu Ala Glu Arg Arg Pro Ile Ala
                325                 330                 335

Ala Ala Ala Leu Arg Asn Thr Asp Leu Leu Phe Arg Phe Asn Thr Ala
            340                 345                 350

Ser Gly Pro Ile Gly Arg Leu Ile His Trp Ile Gly Leu Gln Ala Thr
            355                 360                 365

Arg Ala Pro Tyr Val Ala Gln Lys Val Val Ser Ala Leu Ala Gly Glu
            370                 375                 380

Gly Val Arg Tyr Asp Ser Val Arg Arg Gly Asp His Arg Leu Val
385                 390                 395                 400

Gly Arg Arg Leu Pro Leu Leu Ser Leu Leu Pro Glu Gly Glu Arg Leu
                405                 410                 415

Pro Arg Gln Ser Leu Thr Gln Leu Leu Arg Ala Gly Arg Phe Val Leu
            420                 425                 430

Val His His Arg Ala Lys Ala Leu Ala Ala Asp Leu Arg Arg Asp Phe
            435                 440                 445

Pro Gly Leu Gln Thr Ala Ser Ile Cys Glu Asp Ser His Asn Asn Ser
450                 455                 460

Leu Ser Ala Gly Glu Gly Val Ile Val Arg Pro Asp Gly Val Val Ile
465                 470                 475                 480

Trp Val Gly Lys Lys Ser Thr Leu Ala Lys Glu Arg Leu Gly Glu Trp
                485                 490                 495

Leu Leu Asp Asp Ser Lys Ser Ala Arg Gln Ser Leu Thr
                500                 505

<210> SEQ ID NO 12
<211> LENGTH: 348
<212> TYPE: PRT
<213> ORGANISM: Pseudomonas fluorescens A2-2

<400> SEQUENCE: 12

Met Ala His Tyr Asp Ser Val Gly Thr Ala Pro Gly Ala Ser Asp Asp
 1               5                  10                  15

Gly Met Ala Val Ala Ser Ile Leu Gln Leu Met Arg Glu Thr Ile Thr

-continued

```
                20                  25                  30
Arg Ser Asp Ala Lys Asn Asn Val Val Phe Leu Leu Ala Asp Gly Glu
            35                  40                  45

Glu Leu Gly Leu Leu Gly Ala Glu His Tyr Val Ser Gln Leu Ser Thr
        50                  55                  60

Pro Glu Arg Glu Ala Ile Arg Leu Val Leu Asn Phe Glu Ala Arg Gly
 65                  70                  75                  80

Asn Gln Gly Ile Pro Leu Leu Phe Glu Thr Ser Gln Lys Asp Tyr Ala
                    85                  90                  95

Leu Ile Arg Thr Val Asn Ala Gly Val Arg Asp Ile Ile Ser Phe Ser
                100                 105                 110

Phe Thr Pro Leu Ile Tyr Asn Met Leu Gln Asn Asp Thr Asp Phe Thr
            115                 120                 125

Val Phe Arg Lys Lys Asn Ile Ala Gly Leu Asn Phe Ala Val Val Glu
        130                 135                 140

Gly Phe Gln His Tyr His His Met Ser Asp Thr Val Glu Asn Leu Gly
145                 150                 155                 160

Pro Glu Thr Leu Phe Arg Tyr Gln Lys Thr Val Arg Glu Val Gly Asn
                    165                 170                 175

His Phe Ile Gln Gly Ile Asp Leu Ser Ser Leu Ser Ala Asp Glu Asp
                180                 185                 190

Ala Thr Tyr Phe Pro Leu Pro Gly Thr Leu Leu Val Leu Asn Leu
            195                 200                 205

Pro Thr Leu Tyr Ala Leu Gly Met Gly Ser Phe Val Leu Cys Gly Leu
        210                 215                 220

Trp Ala Gln Arg Cys Arg Thr Arg Arg Gln His Gln Gly Lys Asn Cys
225                 230                 235                 240

Val Leu Arg Pro Met Ala Ile Ala Leu Leu Gly Ile Ala Cys Ala Ala
                    245                 250                 255

Leu Val Phe Tyr Val Pro Ser Ile Ala Tyr Leu Phe Val Ile Pro Ser
                260                 265                 270

Leu Leu Leu Ala Cys Ala Met Leu Ser Arg Ser Leu Phe Ile Ser Tyr
            275                 280                 285

Ser Ile Met Leu Leu Gly Ala Tyr Ala Cys Gly Ile Leu Tyr Ala Pro
        290                 295                 300

Ile Val Tyr Leu Ile Ser Ser Gly Leu Lys Met Pro Phe Ile Ala Gly
305                 310                 315                 320

Val Ile Ala Leu Leu Pro Leu Cys Leu Leu Ala Val Gly Leu Ala Gly
                    325                 330                 335

Val Ile Ala Arg Ser Arg Asp Cys Arg Thr Cys Asp
                340                 345
```

<210> SEQ ID NO 13
<211> LENGTH: 572
<212> TYPE: PRT
<213> ORGANISM: Pseudomonas fluorescens A2-2

<400> SEQUENCE: 13

```
Met Arg Ser Leu Lys Ile Ile Val Leu Ala Ser Ala Phe Asn Gly Leu
  1               5                  10                  15

Thr Gln Arg Ala Trp Leu Asp Leu Arg Gln Ser Gly His Ala Pro Ser
            20                  25                  30

Val Val Leu Phe Thr Asp Pro Ala Leu Val Cys Gln Gln Ile Glu Asp
        35                  40                  45
```

-continued

```
Ser Asp Ala Asp Leu Val Ile Cys Pro Phe Leu Lys Asp Arg Val Pro
 50                  55                  60
Gln Gln Leu Trp Ser Asn Leu Glu Arg Pro Val Ile Ile His Pro
 65                  70                  75                  80
Gly Ile Val Gly Asp Arg Gly Ala Ser Ala Leu Asp Trp Ala Ile Ser
                 85                  90                  95
Gln Gln Val Gly Arg Trp Gly Val Thr Ala Leu Gln Ala Val Glu Glu
                100                 105                 110
Met Asp Ala Gly Pro Ile Trp Ser Thr Cys Glu Phe Asp Met Pro Ala
                115                 120                 125
Asp Val Arg Lys Ser Glu Leu Tyr Asn Gly Ala Val Ser Asp Ala Ala
130                 135                 140
Leu Tyr Cys Ile Arg Asp Val Val Glu Lys Phe Ala Arg Val Phe Val
145                 150                 155                 160
Pro Val Pro Leu Asp Tyr Thr Gln Ala His Val Ile Gly Arg Leu Gln
                165                 170                 175
Pro Asn Met Thr Gln Ala Asp Arg Thr Phe Ser Trp Tyr Asp Cys Ala
                180                 185                 190
Arg Phe Ile Lys Arg Cys Ile Asp Ala Ala Asp Gly Gln Pro Gly Val
                195                 200                 205
Leu Ala Ser Ile Gln Gly Gly Gln Tyr Leu Tyr Asp Ala His Leu
210                 215                 220
Asp Ala Arg His Gly Thr Pro Gly Glu Ile Leu Ala Val Gln Asp Asp
225                 230                 235                 240
Ala Val Leu Val Ala Ala Gly Asp Gln Ser Leu Trp Ile Gly Ser Leu
                245                 250                 255
Lys Arg Lys Ala Arg Pro Gly Glu Glu Thr Phe Lys Leu Pro Ala Arg
                260                 265                 270
His Val Leu Ala Glu Ala Leu Ala Asp Ile Pro Val Leu Asp Ser Ser
                275                 280                 285
Ile Ala Asn Gln Met Phe Asp Glu Gln Ala Tyr Gln Pro Ile Arg Tyr
290                 295                 300
Arg Glu Ala Gly His Val Gly Glu Leu Thr Phe Glu Phe Tyr Asn Gly
305                 310                 315                 320
Ala Met Ser Thr Glu Gln Cys Gln Arg Leu Val Ala Ala Leu Arg Trp
                325                 330                 335
Ala Lys Thr Arg Asp Thr Gln Val Leu Val Ile Lys Gly Gly Arg Gly
                340                 345                 350
Ser Phe Ser Asn Gly Val His Leu Asn Val Ile Gln Ala Ala Pro Val
                355                 360                 365
Pro Gly Leu Glu Ala Trp Ala Asn Ile Gln Ala Ile Tyr Asp Val Cys
370                 375                 380
His Glu Leu Leu Thr Ala Arg Gln Leu Val Ile Ser Gly Leu Thr Gly
385                 390                 395                 400
Ser Ala Gly Ala Gly Gly Val Met Leu Ala Leu Ala Ala Asp Ile Val
                405                 410                 415
Leu Ala Arg Glu Ser Val Val Leu Asn Pro His Tyr Lys Thr Met Gly
                420                 425                 430
Leu Tyr Gly Ser Glu Tyr Trp Thr Tyr Ser Leu Pro Arg Ala Val Gly
                435                 440                 445
Ser Glu Val Ala His Gln Leu Thr Asp Ala Cys Leu Pro Ile Ser Ala
450                 455                 460
Leu Gln Ala Glu Gln Tyr Gly Leu Val Gln Gly Ile Gly Pro Arg Cys
```

```
                465                 470                 475                 480
    Pro His Ala Phe Ser Arg Trp Leu Met Gln Gln Ala Ser Ser Ala Leu
                    485                 490                 495

Thr Asp Glu Lys Tyr Ala Val Ala Arg Ala Arg Lys Ala Ala Leu Asp
                500                 505                 510

Ile Asp Gln Ile Thr Arg Cys Arg Glu Ala Glu Leu Ala Gln Met Gln
                    515                 520                 525

Leu Asp Met Val His Asn Arg His Gln Phe Ala Glu Lys Cys Arg Asn
                530                 535                 540

Phe Val Leu Lys Arg Lys Thr Cys Gln Thr Pro Gln Arg Leu Met Ala
    545                 550                 555                 560

Pro Trp Ala Val Ala Arg Glu Ala Ala Leu Val Gly
                    565                 570

<210> SEQ ID NO 14
<211> LENGTH: 230
<212> TYPE: PRT
<213> ORGANISM: Pseudomonas fluorescens A2-2

<400> SEQUENCE: 14

Met Ile Gly Ile Val Ile Pro Ala His Asn Glu Glu Arg His Ile Ser
1               5                   10                  15

Ala Cys Leu Ala Ser Ile Gln Arg Ala Ile Ala His Pro Ala Leu Ala
                20                  25                  30

His Gln Gln Val Gln Leu Leu Val Leu Asp Ala Cys Ser Asp Glu
            35                  40                  45

Thr Ala Thr Arg Val Ser Ala Met Gly Val Ala Thr Leu Glu Val Ser
    50                  55                  60

Val Arg Asn Val Gly Lys Ala Arg Ala Leu Gly Ala Glu Arg Leu Leu
65                  70                  75                  80

Glu Val Gly Ala Gln Trp Leu Ala Phe Thr Asp Ala Asp Thr Val Val
                85                  90                  95

Pro Ala Asp Trp Leu Val Arg Gln Ile Gly Phe Gly Ala Asp Ala Val
            100                 105                 110

Cys Gly Thr Val Glu Val Asp Ser Trp Ser Glu Tyr Gly Glu Ser Val
        115                 120                 125

Arg Ser Arg Tyr Leu Glu Leu Tyr Gln Phe Thr Glu Asn His Arg His
    130                 135                 140

Ile His Gly Ala Asn Leu Gly Leu Ser Ala Asp Ala Tyr Arg Asn Ala
145                 150                 155                 160

Gly Gly Phe Gln His Leu Val Ala His Glu Asp Val Gln Leu Val Ala
                165                 170                 175

Asp Leu Glu Arg Ile Gly Ala Arg Ile Val Trp Thr Ala Thr Asn Pro
            180                 185                 190

Val Val Thr Ser Ala Arg Arg Asp Tyr Lys Cys Arg Gly Gly Phe Gly
        195                 200                 205

Glu Tyr Leu Ala Ser Leu Val Ala Glu Gly Thr Arg Glu His Ser Pro
    210                 215                 220

Ala His Ala Pro Ile Gly
225                 230

<210> SEQ ID NO 15
<211> LENGTH: 348
<212> TYPE: PRT
<213> ORGANISM: Pseudomonas fluorescens A2-2
```

<400> SEQUENCE: 15

```
Met His Pro His Lys Thr Ala Ile Val Leu Ile Glu Tyr Gln Asn Asp
 1               5                  10                  15

Phe Thr Thr Pro Gly Gly Val Phe His Asp Ala Val Lys Asp Val Met
            20                  25                  30

Gln Thr Ser Asn Met Leu Ala Asn Thr Ala Thr Thr Ile Glu Gln Ala
        35                  40                  45

Arg Lys Leu Gly Val Lys Ile Ile His Leu Pro Ile Arg Phe Ala Asp
    50                  55                  60

Gly Tyr Pro Glu Leu Thr Leu Arg Ser Tyr Gly Ile Leu Lys Gly Val
 65                 70                  75                  80

Ala Asp Gly Ser Ala Phe Arg Ala Gly Ser Trp Gly Ala Glu Ile Thr
                85                  90                  95

Asp Ala Leu Lys Arg Asp Pro Thr Asp Ile Val Ile Glu Gly Lys Arg
            100                 105                 110

Gly Leu Asp Ala Phe Ala Thr Thr Gly Leu Asp Leu Val Leu Arg Asn
        115                 120                 125

Asn Gly Ile Gln Asn Leu Val Val Ala Gly Phe Leu Thr Asn Cys Cys
130                 135                 140

Val Glu Gly Thr Val Arg Ser Gly Tyr Glu Lys Gly Tyr Asp Val Val
145                 150                 155                 160

Thr Leu Thr Asp Cys Thr Ala Thr Phe Ser Asp Glu Gln Gln Arg Ala
                165                 170                 175

Ala Glu Gln Phe Thr Leu Pro Met Phe Phe Ala Asn Pro Ala Thr His
            180                 185                 190

Arg Val Ser Ala Ser Thr Glu Arg Arg Ile Lys Lys Ala Ala Thr Pro
        195                 200                 205

Ala Glu Ser Pro Leu Phe Cys Leu Gly His Ser Val Gly Ala Tyr Cys
    210                 215                 220

Ile Ser Pro Phe Pro Asn Asp Gln Ser Ser Arg Phe Thr Ser Thr Arg
225                 230                 235                 240

Leu Ile His Thr Ser Ser Leu Arg Ser Pro Val Leu Ala Trp Met Pro
                245                 250                 255

Ser Ala Met Asn Leu Lys Ala Phe Phe Thr Ser Met Leu Arg Pro Ala
            260                 265                 270

Phe His Val Thr Trp Ile Asn Thr Ile Leu Gly Val Thr Pro Arg
        275                 280                 285

Tyr Pro Ala Ala Gly Thr Ser Ser Leu Ala Trp Arg Leu Met Ile
    290                 295                 300

Trp Asn Leu Ser Cys Ser Gly Thr Leu Ala Thr Leu Val Ile Ala Ala
305                 310                 315                 320

Tyr Thr Thr Ser Pro Met Ala Val Ala Val Ser Val Glu Val Ser Ala
                325                 330                 335

Ala Arg Ser Ile Arg Thr Lys Gly Met Asp Lys Ser
            340                 345
```

<210> SEQ ID NO 16
<211> LENGTH: 5
<212> TYPE: PRT
<213> ORGANISM: Unknown Organism
<220> FEATURE:
<223> OTHER INFORMATION: Description of Unknown Organism: Illustrative core peptide

<400> SEQUENCE: 16

Leu Lys Ala Gly Ala
 1               5

<210> SEQ ID NO 17
<211> LENGTH: 10
<212> TYPE: PRT
<213> ORGANISM: Unknown Organism
<220> FEATURE:
<223> OTHER INFORMATION: Description of Unknown Organism: Illustrative
      core peptide
<220> FEATURE:
<221> NAME/KEY: MOD_RES
<222> LOCATION: (4)
<223> OTHER INFORMATION: Ser or Thr
<220> FEATURE:
<221> NAME/KEY: MOD_RES
<222> LOCATION: (7)
<223> OTHER INFORMATION: Variable amino acid

<400> SEQUENCE: 17

Ser Gly Thr Xaa Thr Gly Xaa Pro Lys Gly
 1               5                   10

<210> SEQ ID NO 18
<211> LENGTH: 9
<212> TYPE: PRT
<213> ORGANISM: Unknown Organism
<220> FEATURE:
<223> OTHER INFORMATION: Description of Unknown Organism: Illustrative
      core peptide
<220> FEATURE:
<221> NAME/KEY: MOD_RES
<222> LOCATION: (5)
<223> OTHER INFORMATION: Variable amino acid

<400> SEQUENCE: 18

Lys Ile Arg Gly Xaa Arg Ile Glu Leu
 1               5

<210> SEQ ID NO 19
<211> LENGTH: 5
<212> TYPE: PRT
<213> ORGANISM: Unknown Organism
<220> FEATURE:
<223> OTHER INFORMATION: Description of Unknown Organism: Illustrative
      core peptide
<220> FEATURE:
<221> NAME/KEY: MOD_RES
<222> LOCATION: (4)
<223> OTHER INFORMATION: Variable amino acid

<400> SEQUENCE: 19

Leu Gly Gly Xaa Ser
 1               5

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)
<223> OTHER INFORMATION: a, c, t, g, unknown or other
<220> FEATURE:
<221> NAME/KEY: modified_base
<222> LOCATION: (9)
<223> OTHER INFORMATION: a, c, t, g, unknown or other
<220> FEATURE:
<221> NAME/KEY: modified_base -continued

```
<222> LOCATION: (12)
<223> OTHER INFORMATION: a, c, t, g, unknown or other

<400> SEQUENCE: 20
tayggnccna cnga                                                        14

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)
<223> OTHER INFORMATION: a, c, t, g, unknown or other
<220> FEATURE:
<221> NAME/KEY: modified_base
<222> LOCATION: (6)
<223> OTHER INFORMATION: a, c, t, g, unknown or other
<220> FEATURE:
<221> NAME/KEY: modified_base
<222> LOCATION: (9)
<223> OTHER INFORMATION: a, c, t, g, unknown or other
<220> FEATURE:
<221> NAME/KEY: modified_base
<222> LOCATION: (12)
<223> OTHER INFORMATION: a, c, t, g, unknown or other

<400> SEQUENCE: 21
tsnccnccna dntcraaraa                                                  20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgtctagaca ccggcttcat gg                                               22

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggtctagata acagccaaca aacata                                           26

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
catctagacc ggactgatat tcg                                              23

<210> SEQ ID NO 25
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25
ggtctagata acagccaaca aacata                                            26

<210> SEQ ID NO 26
<211> LENGTH: 6
<212> TYPE: PRT
<213> ORGANISM: Unknown Organism
<220> FEATURE:
<223> OTHER INFORMATION: Description of Unknown Organism: Illustrative
      core peptide

<400> SEQUENCE: 26

Leu Lys Ala Gly Gly Ala
  1               5

<210> SEQ ID NO 27
<211> LENGTH: 5
<212> TYPE: PRT
<213> ORGANISM: Unknown Organism
<220> FEATURE:
<223> OTHER INFORMATION: Description of Unknown Organism: Illustrative
      core peptide

<400> SEQUENCE: 27

Ser Gly Thr Thr Gly
  1               5

<210> SEQ ID NO 28
<211> LENGTH: 7
<212> TYPE: PRT
<213> ORGANISM: Unknown Organism
<220> FEATURE:
<223> OTHER INFORMATION: Description of Unknown Organism: Illustrative
      core peptide

<400> SEQUENCE: 28

Gly Glu Leu Cys Ile Gly Gly
  1               5

<210> SEQ ID NO 29
<211> LENGTH: 8
<212> TYPE: PRT
<213> ORGANISM: Unknown Organism
<220> FEATURE:
<223> OTHER INFORMATION: Description of Unknown Organism: Illustrative
      core peptide

<400> SEQUENCE: 29

Arg Ile Glu Leu Gly Glu Ile Glu
  1               5

<210> SEQ ID NO 30
<211> LENGTH: 5
<212> TYPE: PRT
<213> ORGANISM: Unknown Organism
<220> FEATURE:
<223> OTHER INFORMATION: Description of Unknown Organism: Illustrative
      core peptide

<400> SEQUENCE: 30

Leu Gly Gly His Ser
  1               5
```

```
<210> SEQ ID NO 31
<211> LENGTH: 578
<212> TYPE: PRT
<213> ORGANISM: Myxococcus xanthus
<220> FEATURE:
<221> NAME/KEY: MOD_RES
<222> LOCATION: (13)..(90)
<223> OTHER INFORMATION: Variable amino acid
<220> FEATURE:
<221> NAME/KEY: MOD_RES
<222> LOCATION: (102)..(321)
<223> OTHER INFORMATION: Variable amino acid
<220> FEATURE:
<221> NAME/KEY: MOD_RES
<222> LOCATION: (336)..(358)
<223> OTHER INFORMATION: Variable amino acid
<220> FEATURE:
<221> NAME/KEY: MOD_RES
<222> LOCATION: (365)..(387)
<223> OTHER INFORMATION: Variable amino acid
<220> FEATURE:
<221> NAME/KEY: MOD_RES
<222> LOCATION: (397)..(559)
<223> OTHER INFORMATION: Variable amino acid

<400> SEQUENCE: 31

Leu Tyr Ala Gly Val Val Ala Val Pro Val Tyr Pro Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Tyr Thr Ser Gly Ser Thr
                85                  90                  95

Ala Asp Pro Lys Gly Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270
```

```
Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa
305                 310                 315                 320

Xaa Gly Glu Ile Trp Val Arg Gly Pro Ser Val Ala Gln Gly Tyr Xaa
            325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Leu Arg Thr Gly Asp Leu Xaa Xaa Xaa
        355                 360                 365

Xaa Xaa Xaa Xaa Xaa Xaa Xaa Xaa Xaa Xaa Xaa Xaa Xaa Xaa Xaa
370                 375                 380

Xaa Xaa Xaa Asn Tyr Tyr Pro Gln Asp Leu Glu Leu Xaa Xaa Xaa Xaa
385                 390                 395                 400

Xaa Xaa Xaa Xaa Xaa Xaa Xaa Xaa Xaa Xaa Xaa Xaa Xaa Xaa Xaa
        405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
        485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa
        530                 535                 540

Xaa Xaa Xaa Xaa Xaa Xaa Xaa Xaa Xaa Xaa Xaa Xaa Xaa Leu
545                 550                 555                 560

Pro Asp Leu Gly Leu Asp Ser Leu Ala Leu Val Glu Leu Lys His Arg
            565                 570                 575

Ile Glu

<210> SEQ ID NO 32
<211> LENGTH: 475
<212> TYPE: PRT
<213> ORGANISM: Myxococcus xanthus
<220> FEATURE:
<221> NAME/KEY: MOD_RES
<222> LOCATION: (13)..(76)
<223> OTHER INFORMATION: Variable amino acid
<220> FEATURE:
<221> NAME/KEY: MOD_RES
<222> LOCATION: (88)..(259)
<223> OTHER INFORMATION: Variable amino acid
<220> FEATURE:
<221> NAME/KEY: MOD_RES
<222> LOCATION: (274)..(297)
<223> OTHER INFORMATION: Variable amino acid
<220> FEATURE:
<221> NAME/KEY: MOD_RES
<222> LOCATION: (304)..(326)
```

<223> OTHER INFORMATION: Variable amino acid
<220> FEATURE:
<221> NAME/KEY: MOD_RES
<222> LOCATION: (336)..(456)
<223> OTHER INFORMATION: Variable amino acid

<400> SEQUENCE: 32

```
Leu Glu Ala Gly Gly Val Ala Val Pro Leu Asp Pro Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Tyr Thr Ser Gly
65                  70                  75                  80

Ser Thr Gly Gln Pro Lys Gly Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Gly Glu Leu Phe Ile Gly Gly Ala Gly Val Ala Arg Gly
            260                 265                 270

Tyr Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Tyr Arg Thr Gly Asp Leu Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Phe Arg Ile Glu Phe Glu Glu Ile Glu Xaa
                325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380
```

```
Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Phe Phe Asp Leu Gly Gly Asn Ser
    450                 455                 460

Leu Leu Ala Thr Arg Leu Ala Thr Arg Leu Ala
465                 470                 475

<210> SEQ ID NO 33
<211> LENGTH: 476
<212> TYPE: PRT
<213> ORGANISM: Myxococcus xanthus
<220> FEATURE:
<221> NAME/KEY: MOD_RES
<222> LOCATION: (13)..(76)
<223> OTHER INFORMATION: Variable amino acid
<220> FEATURE:
<221> NAME/KEY: MOD_RES
<222> LOCATION: (88)..(260)
<223> OTHER INFORMATION: Variable amino acid
<220> FEATURE:
<221> NAME/KEY: MOD_RES
<222> LOCATION: (275)..(298)
<223> OTHER INFORMATION: Variable amino acid
<220> FEATURE:
<221> NAME/KEY: MOD_RES
<222> LOCATION: (305)..(327)
<223> OTHER INFORMATION: Variable amino acid
<220> FEATURE:
<221> NAME/KEY: MOD_RES
<222> LOCATION: (337)..(457)
<223> OTHER INFORMATION: Variable amino acid

<400> SEQUENCE: 33

Leu Lys Ala Gly Gly Ala Tyr Val Pro Leu Asp Pro Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Tyr Thr Ser Gly
65                  70                  75                  80

Ser Ser Gly Arg Pro Lys Gly Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175
```

```
Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa
            245                 250                 255

Xaa Xaa Xaa Xaa Gly Glu Leu Phe Ile Gly Gly Ser Gly Val Ala Arg
            260                 265                 270

Gly Tyr Xaa Xaa Xaa Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Tyr Arg Thr Gly Asp Leu
        290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Tyr Arg Ile Glu Leu Ala Glu Ile Glu
            325                 330                 335

Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Phe Phe Glu Leu Gly Gly Asn
        450                 455                 460

Ser Leu Leu Ala Gly Arg Leu Val Glu Glu Leu Asp
465                 470                 475

<210> SEQ ID NO 34
<211> LENGTH: 486
<212> TYPE: PRT
<213> ORGANISM: Myxococcus xanthus
<220> FEATURE:
<221> NAME/KEY: MOD_RES
<222> LOCATION: (13)..(79)
<223> OTHER INFORMATION: Variable amino acid
<220> FEATURE:
<221> NAME/KEY: MOD_RES
<222> LOCATION: (91)..(269)
<223> OTHER INFORMATION: Variable amino acid
<220> FEATURE:
<221> NAME/KEY: MOD_RES
<222> LOCATION: (284)..(307)
<223> OTHER INFORMATION: Variable amino acid
<220> FEATURE:
<221> NAME/KEY: MOD_RES
<222> LOCATION: (314)..(336)
<223> OTHER INFORMATION: Variable amino acid
```

<220> FEATURE:
<221> NAME/KEY: MOD_RES
<222> LOCATION: (346)..(467)
<223> OTHER INFORMATION: Variable amino acid

<400> SEQUENCE: 34

```
Leu Lys Ala Gly Gly Ala Tyr Val Pro Leu Asp Pro Xaa Xaa Xaa
  1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Tyr
 65                  70                  75                  80

Thr Ser Gly Ser Thr Gly Thr Pro Lys Ala Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Gly Glu Leu
            260                 265                 270

Phe Val Gly Gly Val Gly Leu Ala Arg Gly Tyr Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Tyr Arg Thr Gly Asp Leu Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Tyr Arg Val Glu Leu Gly Glu Ile Glu Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380
```

```
Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
    450                 455                 460

Xaa Xaa Xaa Phe Phe Glu Val Gly Gly Thr Ser Leu Leu Leu Ala Arg
465             470                 475                 480

Leu Ala Ser Arg Leu Leu
                485

<210> SEQ ID NO 35
<211> LENGTH: 5
<212> TYPE: PRT
<213> ORGANISM: Unknown Organism
<220> FEATURE:
<223> OTHER INFORMATION: Description of Unknown Organism: A5 core
      peptide

<400> SEQUENCE: 35

Tyr Gly Pro Thr Glu
1               5
```

GENE CLUSTER INVOLVED IN SAFRACIN BIOSYNTHESIS AND ITS USES FOR GENETIC ENGINEERING

FIELD OF THE INVENTION

The present invention relates to the gene cluster responsible for the biosynthesis of safracin, its uses for genetic engineering and new safracins obtained by manipulation of the biosynthesis mechanism.

BACKGROUND OF THE INVENTION

Safracins, a family of new compounds with a potent broad-spectrum antibacterial activity, were discovered in a culture broth of *Pseudomonas* sp. Safracin occurs in two *Pseudomonas* sp. strains, *Pseudomonas fluorescens* A2-2 isolated from a soil sample collected in Tagawagun, Fukuoka, Japan (Ikeda et al. *J. Antibiotics* 1983, 36, 1279-1283; WO 82 00146 and JP 58113192) and *Pseudomonas fluorescens* SC 12695 isolated from water samples taken from the Raritan-Delaware Canal, near New Jersey (Meyers et al. *J. Antibiot.* 1983, 36(2), 190-193). Safracins A and B, produced by *Pseudomonas fluorescens* A2-2, have been examined against different tumor cell lines and has been found to possess antitumor activity in addition to antibacterial activity.

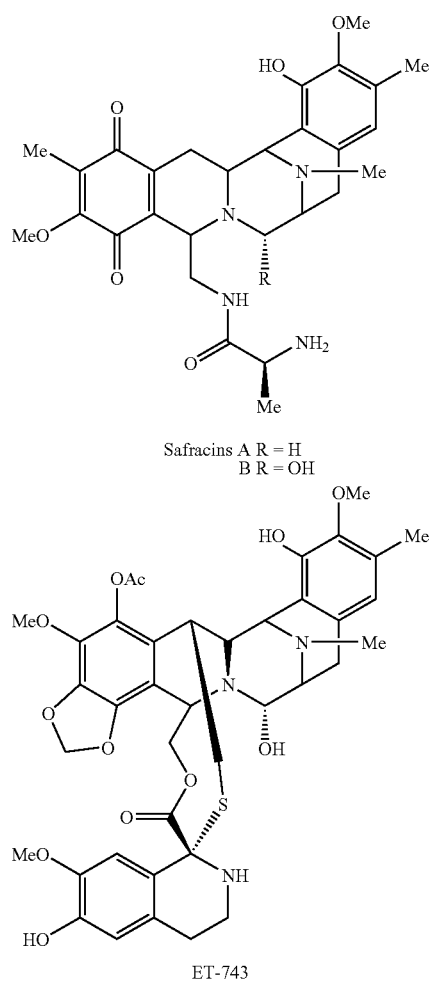

Safracins A R = H
B R = OH

ET-743

Due to the structural similarities between safracin B and ET-743 safracin offers the possibility of hemi-synthesis of the highly promising potent new antitumor agent ET-743, isolated from the marine tunicate *Ecteinascidia turbinata* and which is currently in Phase II clinical trials in Europe and the United States. A hemisynthesis of ET-743 has been achieved starting from safracin B (Cuevas et al. *Organic Lett.* 2000, 10, 2545-2548; WO 00 69862 and WO 01 87895).

As an alternative of making safracins or its structural analogs by chemical synthesis, manipulating genes of governing secondary metabolism offer a promising alternative and allows for preparation of these compounds biosynthetically. Additionally, safracin structure offers exciting possibilities for combinatorial biosynthesis.

In view of the complex structure of the safracins and the limitations in their obtention from *Pseudomonas fluorescens* A2-2, it would be highly desirable to understand the genetic basis of their synthesis in order to create the means to influence them in a targeted manner. This could increase the amounts of safracins being produced, because natural production strains generally yield only low concentrations of the secondary metabolites that are of interest. It could also allow the production of safracins in hosts that otherwise do not produce these compounds. Additionally, the genetic manipulation could be used for combinatorial creation of novel safracin analogs that could exhibit improved properties and that could be used in the hemi-synthesis of new ecteinascidins compounds.

However, the success of a biosynthetic approach depends critically on the availability of novel genetic systems and on genes encoding novel enzyme activities. Elucidation of the safracin gene cluster contributes to the general field of combinatorial biosynthesis by expanding the repertoire of genes uniquely associated with safracin biosynthesis, leading to the possibility of making novel precursors and safracins via combinatorial biosynthesis.

SUMMARY OF THE INVENTION

We have now been able to identify and clone the genes of safracin biosynthesis, providing the genetic basis for improving and manipulating in a targeted manner the productivity of *Pseudomonas* sp., and using genetic methods, for synthesising safracin analogues. Additionally, these genes encode enzymes that are involved in biosynthetic processes to produce structures, such as safracin precursors, that can form the basis of combinatorial chemistry to produce a wide variety of compounds. These compounds can be screened for a variety of bioactivities including anticancer activity.

Therefore in a first aspect the present invention provides a nucleic acid, suitably an isolated nucleic acid, which includes a DNA sequence (including mutations or variants thereof, that encodes non-ribosomal peptide synthetases which are responsible for the biosynthesis of safracins. This invention provides a gene cluster, suitably an isolated gene cluster, with open reading frames encoding polypeptides to direct the assembly of a safracin molecule.

One aspect of the present invention is a composition including at least one nucleic acid sequence, suitably an isolated nucleic acid molecule, that encodes at least one polypeptide that catalyses at least one step of the biosynthesis of safracins. Two or more such nucleic acid sequences can be present in the composition. DNA or corresponding RNA is also provided.

In particular the present invention is directed to a nucleic acid sequence, suitably an isolated nucleic acid sequence, from a safracin gene cluster comprising said nucleic acid sequence, a portion or portions of said nucleic acid sequence wherein said portion or portions encode a polypeptide or polypeptides or a biologically active fragment of a polypeptide or polypeptides, a single-stranded nucleic acid sequence derived from said nucleic acid sequence, or a single stranded nucleic acid sequence derived from a portion or portions of said nucleic acid sequence, or a double-stranded nucleic acid sequence derived from the single-stranded nucleic acid sequence (such as cDNA from mRNA). The nucleic acid sequence can be DNA or RNA.

More particularly, the present invention is directed to a nucleic acid sequence, suitably an isolated nucleic acid sequence, which includes or comprises at least SEQ ID 1, variants or portions thereof, or at least one of the sacA, sacB, sacC, sacC, sacD, sacE, sacF, sacG, sacH, sacH, sacI, sacJ, orf1, orf2, orf3 or orf4 genes, including variants or portions. Portions can be at least 10, 15, 20, 25, 50, 100, 1000, 2500, 5000, 10000, 20000, 25000 or more nucleotides in length. Typically the portions are in the range 100 to 5000, or 100 to 2500 nucleotides in length, and are biologically functional.

Mutants or variants include polynucleotide molecules in which at least one nucleotide residue is altered, substituted, deleted or inserted. Multiple changes are possible, with a different nucleotide at 1, 2, 3, 4, 5, 10, 15, 25, 50, 100, 200, 500 or more positions. Degenerate variants are envisaged which encode the same polypeptide, as well as non-degenerate variants which encode a different polypeptide. The portion, mutant or variant nucleic acid sequence suitably encodes a polypeptide which retains a biological activity of the respective polypeptide encoded by any of the open reading frames of the safracin gene cluster. Allelic forms and polymorphisms are embraced.

The invention is also directed to an isolated nucleic acid sequence capable of hybridizing under stringent conditions with a nucleic acid sequence of this invention. Particularly preferred is hybridisation with a translatable length of a nucleic acid sequence of this invention.

The invention is also directed to a nucleic acid encoding a polypeptide which is at least 30%, preferably 50%, preferably 60%, more preferably 70%, in particular 80%, 90%, 95% or more identical in amino acid sequence to a polypeptide encoded by any of the safracin gene cluster open reading frames sacA to sacJ and orf1 to orf4 (SEQ ID 1 and genes encoded in SEQ ID 1) or encoded by a variant or portion thereof. The polypeptide suitably retains a biological activity of the respective polypeptide encoded by any of the safracin gene cluster open reading frames.

In particular, the invention is directed to an isolated nucleic acid sequence encoding for any of SacA, SacB, SacC, SacD, SacE, SacF, SacG, SacH, SacI, SacJ, Orf1, Orf2, Orf3 or Orf4 proteins (SEQ ID 2-15), and variants, mutants or portions thereof.

In one aspect, an isolated nucleic acid sequence of this invention encodes a peptide synthetase, a L-Tyr derivative hidroxylase, a L-Tyr derivative methylase, a L-Tyr O-methylase, a methyl-transferase or a monooxygenase or a safracin resistance protein.

The invention also provides a hybridization probe which is a nucleic acid sequence as defined above or a portion thereof. Probes suitably comprise a sequence of at least 5, 10, 15, 20, 25, 30, 40, 50, 60, or more nucleotide residues. Sequences with a length on the range 25 to 60 are preferred. The invention is also directed to the use of a probe as defined for the detection of a safracin or ecteinascidin gene. In particular, the probe is used for the detection of genes in *Ecteinascidia turbinata*.

In a related aspect the invention is directed to a polypeptide encoded by a nucleic acid sequence as defined above. Full sequence, variant, mutant or fragment polypeptides are envisaged.

In a further aspect the invention is directed to a vector, preferably an expression vector, preferably a cosmid, comprising a nucleic acid sequence encoding a protein or biologically active fragment of a protein, wherein said nucleic acid is as defined above.

In another aspect the invention is directed to a host cell transformed with one or more of the nucleic acid sequences as defined above, or a vector, an expression vector or cosmid as defined above. A preferred host cell is transformed with an exogenous nucleic acid comprising a gene cluster encoding polypeptides sufficient to direct the assembly of a safracin or safracin analog. Preferably the host cell is a microorganism, more preferably a bacteria.

The invention is also directed to a recombinant bacterial host cell in which at least a portion of a nucleic acid sequence as defined above is disrupted to result in a recombinant host cell that produces altered levels of safracin compound or safracin analogue, relative to a corresponding nonrecombinant bacterial host cell.

The invention is also directed to a method of producing a safracin compound or safracin analogue comprising fermenting, under conditions and in a medium suitable for producing such a compound or analogue, an organism such as *Pseudomonas* sp, in which the copy number of the safracin genes/cluster encoding polypeptides sufficient to direct the assembly of a safracin or safracin analog has been increased.

The invention is also directed to a method of producing a safracin compound or analogue comprising fermenting, under conditions and in a medium suitable for producing such compound or analogue, an organism such as *Pseudomonas* sp in which expression of the genes encoding polypeptides sufficient to direct the assembly of a safracin or safracin analogue has been modulated by manipulation or replacement of one or more genes or sequence responsible for regulating such expression. Preferably expression of the genes is enhanced.

The invention is also directed to the use of a composition including at least one isolated nucleic acid sequence as defined above or a modification thereof for the combinatorial biosynthesis of non-ribosomal peptides, diketopiperazine rings and safracins.

In particular the method involves contacting a compound that is a substrate for a polypeptide encoded by one or more of the safracin biosynthesis gene cluster open reading frames as defined above with the polypeptide encoded by one or more safracin biosynthesis gene cluster open reading frames, whereby the polypeptide chemically modifies the compound.

In still another embodiment, this invention provides a method of producing a safracin or safracin analog. The method involves providing a microorganism transformed with an exogenous nucleic acid comprising a safracin gene cluster encoding polypeptides sufficient to direct the assembly of said safracin or safracin analog; culturing the bacteria under conditions permitting the biosynthesis of safracin or safracin analog; and isolating said safracin or safracin analog from said cell.

The invention is also directed to any of the precursor compounds P2, P14, analogs and derivatives thereof and their use in the combinatorial biosynthesis non-ribosomal peptides, diketopiperazine rings and safracins.

Additionally, the invention is also directed to the new safracins obtained by knock out safracin P19B, safracin P22A, safracin P22B, safracin D and safracin E, and their use as antimicrobial or antitumor agents, as well as their use in the synthesis of ecteinascidin compounds.

The invention is also directed to new safracins obtained by directed biosynthesis as defined above, and their use as antimicrobial or antitumor agents, as well as their use in the synthesis of ecteinascidin compounds. In particular the invention is directed to safracin B-ethoxy and safracin A-ethoxy and their use.

In one aspect, the present invention enables the preparation of structures related to safracins and ecteinascidins which cannot or are difficult to prepare by chemical synthesis. Another aspect is to use the knowledge to gain access to the biosynthesis of ecteinascidins in Ecteinascidia turbinata, for example using these sequences or parts as probes in this organism or a putative symbiont.

More fundamentally, the invention opens a broad field and gives access to ecteinascidins by genetic engineering.

BRIEF DESCRIPTION OF THE FIGURES

FIG. 2: Conserved core motifs between NRPSs. Conserved amino acid sequences in SacA (Residues 484-953 of SEQ ID NO: 2), SacB (Residues 525-999 of SEQ ID NO: 3) and SacC (Residues 516-992 of SEQ ID NO: 4) proteins and their comparison with its homologous sequences from Myxococcus xanthus DM50415 (Core sequences disclosed as SEQ ID NOS: 26-30; SafB1, SafB2, SafA1 and SafA2 disclosed as SEQ ID NOS: 31-34, respectively, in order of appearance).

FIG. 8: Addition of specific designed "unnatural" precursors (P3). Chemical structure of the two molecules obtained by addition of P3 compound to the sacF mutant.

DETAILED DESCRIPTION OF THE INVENTION

Figure 1:
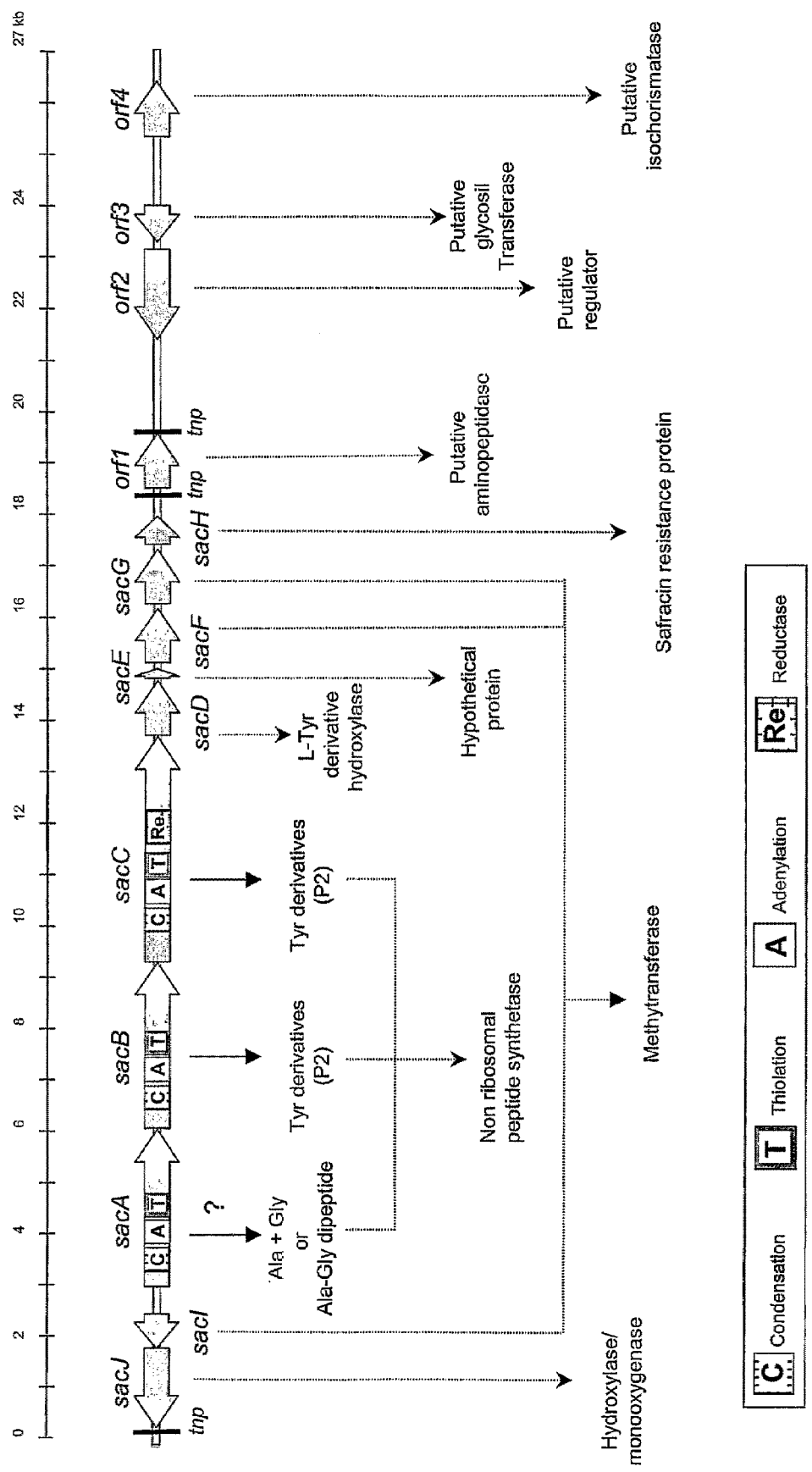
FIG. 1: Structural organization of the chromosomal DNA region cloned in pL30p cosmid. The region of P. fluorescens A2-2 DNA, containing the safracin gene cluster, is shown. Both, sacABCDEFGH and sacIJ, gene operons and the modular organization of the peptide synthetases deduced from sacA, sacB and sacC are illustrated. The following domains are indicated: C: condensation; T: thiolation; A: adenylation and Re: reductase. Location of other genes present in pL30p cosmid (orf1 to orf4) as well as their proposed function is shown.
Figure 3:
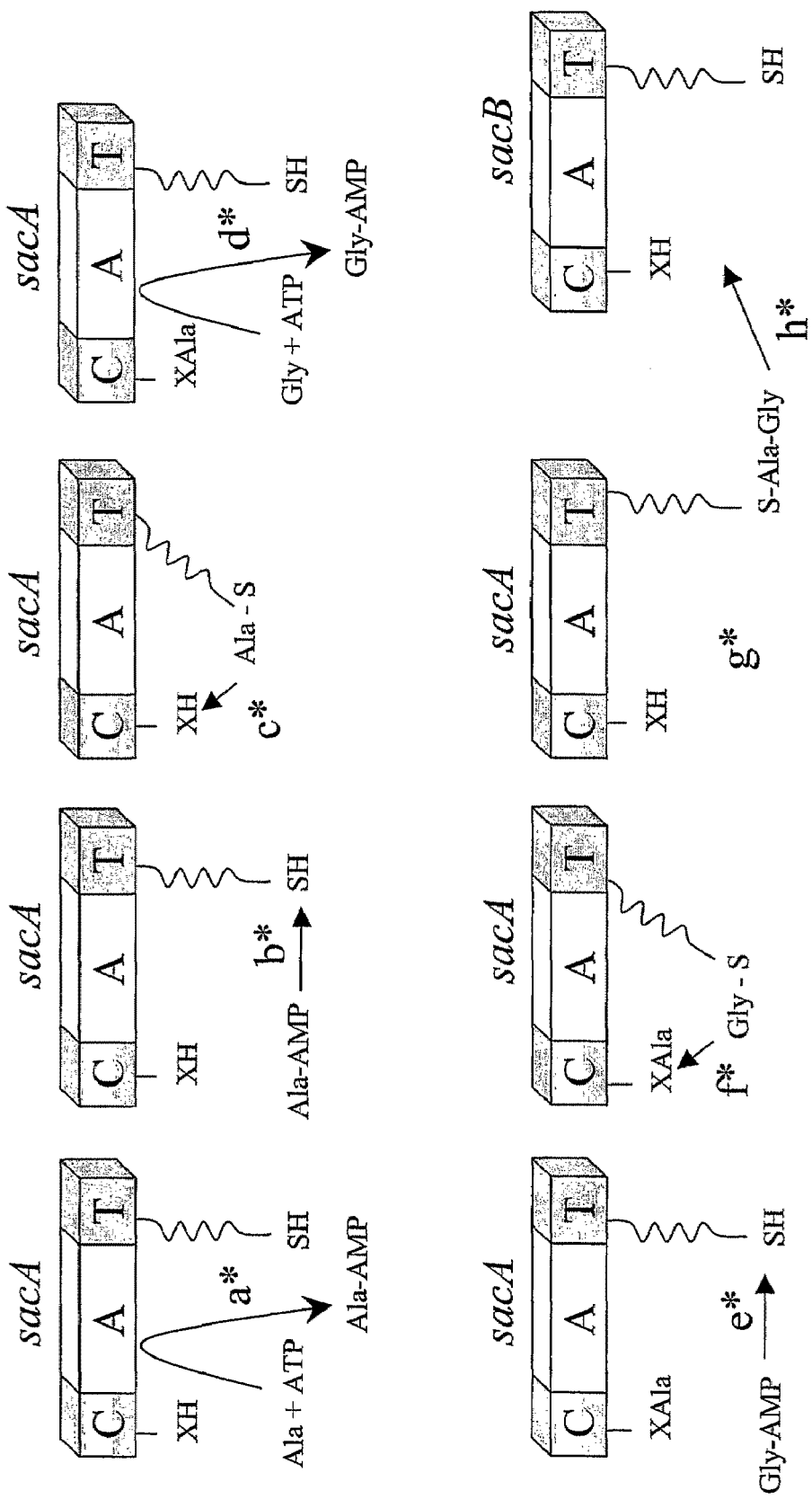
FIG. 3. NRPS biosynthesis mechanism proposed for the formation of the Ala-Gly dipeptide. Step a*, adenylation of Ala; b*, transfer to the 4'-phosphopantetheinyl arm; c*, transfer to the waiting/elongation site; d*, adenylation of the Gly; e*, transfer to the 4'-phosphopantetheinyl arm; f*, condensation of the elongation chain on the 4'-phosphopantetheinyl arm with the starter chain at the waiting/elongation site; g*, Ala-Gly dipeptide attached to the phosphopantetheinyl arm of SacA and h*, transfer of the elongated chain to the following waiting/elongation site.

Non ribosomal peptide synthetases (NRPS) are enzymes responsible for the biosynthesis of a family of compounds that include a large number of structurally and functionally diverse natural products. For example, peptides with biological activities provide the structural backbone for compounds that exhibit a variety of biological activities such as, antibiotics, antiviral, antitumor, and immunosuppressive agents (Zuber et al. *Biotechnology of Antibiotics* 1997 (W. Strohl, ed.), 187-216 Marcel dekker, Inc., N.Y; Marahiel et al. *Chem. Rev.* 1997, 97, 2651-2673).

Although structurally diverse, most of these biologically active peptides share a common mechanistic scheme of biosynthesis. According to this model, peptide bond formation takes place on multienzymes designated peptides synthetases, on which amino acid substrates are activated by ATP hydrolysis to the corresponding adenylate. This unstable intermediate is subsequently transferred to another site of the multienzymes where it is bound as a thioester to the cysteamine group of an enzyme-bound 4'-phosphopantetheinyl (4'-PP) cofactor. At this stage, the thiol-activated substrates can undergo modifications such as epimerisation or N-methylation. Thioesterified substrate amino acids are then integrated into the peptide product through a step-by-step elongation by a series of transpeptidation reactions. With this template arrangement in peptide synthetases, the modules seem to operate independently of one another, but they act in concert to catalyse the formation of successive peptide bonds (Stachelhaus et al. *Science* 1995, 269, 69-72; Stachelhaus et al. *Chem. Biol.* 1996, 3, 913-921). The general scheme for non-ribosomal peptide biosynthesis has been widely reviewed (Marahiel et al. *Chem. Rev.* 1997, 97, 2651-2673; Konz and Marahiel, *Chem. and Biol.* 1999, 6, R39-R48; Moffit and Neilan, *FEMS Microbiol. Letters* 2000, 191, 159-167).

A large number of bacterial operons and fungal genes encoding peptide synthetases have recently been cloned, sequenced and partially characterized, providing valuables insights into their molecule architecture (Marahiel, *Chem and Biol.* 1997, 4, 561-567). Different cloning strategies were used, including probing of expression libraries by antibodies raised against peptide synthetases, complementation of deficient mutants, and the use of designed oligonucleotides derived from amino acid sequences of peptide synthetase fragments.

Analysis of the primary structure of these genes revealed the presence of distinct homologous domains of about 600 amino acids. This specific functional domains consist of at least six highly conserved core sequences of about three to eight amino acids in length, whose order and location within all known domains are very similar (Küsard and Marahiel, *Peptide Research* 1994, 7, 238-241). The used of degenerated oligonucleotides derived from the conserved cores opens the possibility of identifying and cloning peptide synthetases from genomic DNA, by using the polymerase chain reaction (PCR) technology (Küsard and Marahiel, *Peptide Research* 1994, 7, 238-241; Borchert et al. *FEMS Microbiol Letters* 1992, 92,175-180).

The structure of safracin suggests that this compound is synthesized by a NRPS mechanism. The cloning and expression of the non-ribosomal peptide synthetases and the associated tailoring enzymes from *Pseudomonas fluorescens* A2-2 safracin cluster would allow production of unlimited amounts of safracin. In addition, the cloned genes could be used for combinatorial creation of novel safracin analogs that could exhibit improved properties and that could be used in the hemi-synthesis of new ecteinascidins. Moreover, cloning and expressing the safracin gene cluster in heterologous systems or the combination of safracin gene cluster with other NRPS genes could result in the creation of novel drugs with improved activities.

The present invention provides, in particular, the DNA sequence encoding NRPS responsible for biosynthesis of safracin, i.e., safracin synthetases. We have characterized a 26,705 bp region (SEQ ID NO:1) from *Pseudomonas fluorescens* A2-2 genome, cloned in pL30P cosmid and demonstrated, by knockout experiments and heterologous expression, that this region is responsible for the safracin biosynthesis. We expressed the pL30P cosmid in two strains of *Pseudomonas* sp., which do not produce safracin, and the result was a production of safracin A and B at levels of a 22%, for *P. fluorescens* (CECT 378), and 2%, for *P. aeruginosa* (CECT 110), in comparison with *P. fluorescens* A2-2 production. The predicted amino acids sequences of the various peptides encoded by this DNA sequence is shown in SEQ ID NO:2 through SEQ ID NO:15 respectively.

The gene cluster for safracin biosynthesis derived from *P. fluorescens* A2-2, is characterized by the presence of several open reading frames (ORF) that are organized in two divergent operons (FIG. 1), an eight genes operon (sacABCDEFGH) and a two genes operon (sacIJ), preceded by well-conserved putative promoters regions that overlap. The safracin biosynthesis gene cluster is present in only one copy in *P. fluorescens* A2-2 genome.

Our results indicate that the eight genes operon would be responsible for the safracin skeleton biosynthesis and the two genes operon would be responsible for the final tailoring of safracins.

In the sacABCDEFGH operon, the deduced amino acid sequences encoded by sacA, sacB and sacC strongly resemble gene products of NRPSs. Within the deduced amino acid sequences of SacA, SacB and SacC, one peptide synthetase module was identified on each of the ORFs.

The first surprising feature of the safracin NRPS proteins is that from the known active sites and core regions of peptide synthetases (Konz and Marahiel, *Chem. and Biol.* 1999, 6, R39-R48), the first core is poorly conserved in all three peptide synthetases, SacA, SacB and SacC (FIG. 2). The other five core regions are well conserved in the three safracin NRPSs genes. The biological significance of the first core (LKAGA; SEQ ID NO: 16) is unknown, but the SGT(ST) TGxPKG (SEQ ID NO: 17) (Gocht and Marahiel, *J. Bacte-Hol.* 1994, 176, 2654-266; Konz and Marahiel, *Chem. and Biol.* 1999, 6, R39-R48), the TGD(Gocht and Marahiel, *J. Bactetiol.* 1994, 176, 2654-2662; Konz and Marahiel, 1999) and the KIRGxRIEL (SEQ ID NO: 18) (Pavela-Vrancic et al. *J. Biol. Chem* 19942 269, 14962-14966; Konz; and Marahiel, *Chem. and Biol.* 1999, 6, R39-R48) core sequences could be assigned to ATP binding and hydrolysis. The serine residue of the core sequence LGGxS (SEQ ID NO: 19) could be shown to be the site of thioester formation (D'Souza et al., *J. Bacteriol.* 1993, 175, 3502 3510; Vollenbroich etal., FEBS Lett. 1993, 325(3), 220-4; Konz and Marahiel, *Chem. and Biol.* 1999, 6, R39-R48) and 4'-phosphopantetheine binding (Stein et al. FEBS Lett. 1994, 340, 39-44; Konz and Marahiel, *Chem. and Biol.* 1999, 6, R39-R48). These findings, together with the fact that safracin seems to be synthesized from amino acids, supports the hypothesis that non-ribosomal peptide bond formation via the thiotemplate mechanism is involved in the biosynthetic pathway of safracin and that sacA, sacB and sacC encode the corresponding peptide synthetases. According to this mechanism, amino acids are activated as aminoacyl adenylates by ATP hydrolysis and subsequently covalently bound to the enzyme via carboxyl-thioester linkages. Then, in further steps, transpeptidation and peptide bond formation occurs.

Secondly, it is striking that our sequence data clearly shows that the colinearity rule, according to which the order of the amino acid binding modules along the chromosome parallels the order of the amino acids in the peptide, does not hold for the safracin synthetase system. According to the sequence database homologies and safracin and saframycin structures homologies, SacA would be responsible for the recognition and activation of the Gly residue and SacB and SacC would be responsible for the recognition and activation of the two L-Tyr derivatives that are incorporated into the safracin skeleton, while the putative Ala-NRPS gene would be missing in the safracin gene cluster. In a few nonribosomal peptide synthetases gene clusters, such as in the pristamycin (Crecy-Lagard et al, *J. of Bacteriol.* 1997, 179(3), 705-713) and in the phosphinothricin tripeptide (Schwartz et al. *Appl Environ Microbiol* 1996, 62, 570-577) biosynthesis pathways, the first NRPS is not juxtaposed with the second NRPS gene. In concrete, in the pristamycin biosynthetic pathway the first structural gene (snbA) and the second structural gene (snbC) are 130 kb apart. This is not the case for the safracin gene cluster where the results of the heterologous expression with the pL30P cosmid clearly demonstrates that there is no NRPS gene missing since there is heterologous safracin production.

Thirdly, even though the question about the mechanism by which the dipeptide Ala-Gly is formed remains open, the presence in sacA of an extra C domain at the amino terminus of the first NRPS gene, suggests the possibility of a bifunctional adenylation activation activity by this gene. We propose that the Ala would be first charged on the phosphopantetheinyl arm of SacA (FIGS. 3 *a** and *b) before being transferred to a waiting position, a condensation domain, located in N-terminal of saca (FIG. 3**, *c). The Gly adenylate would then be charged on the same phosphopantetheinyl arm (FIGS. 3**, *d** and *e), positioned to the elongation site, and elongation would occur (FIG. 3**, *f). The arm of the first module would at this stage be charged with a Ala-Gly dipeptide (FIG. 3**, *g). We proposed that the dipeptide would then be transferred on a waiting position in the second phosphopantetheinyl arm (FIG. 3**, *h**), located in SacB, to continue the synthesis of the safracin tetrapeptide basic skeleton. An alternative biosynthesis mechanism could be the direct incorporation of a dipeptide Ala-Gly into SacA. In this case, the dipeptide could be originated from the activity of highly active peptidyl transferase ribozyme family (Sun et al, *Chem. and Biol.* 2002, 9, 619-626) or from the activity of bacterial proteolysis.

And fourthly, although in most of the prokaryotic peptide synthetases the thioesterase moiety, which appears to be responsible for the release of the mature peptide chain from the enzyme, is fused to the C-terminal end of the last amino acid binding module (Marahiel et al. *Chem. Rev.* 1997, 97, 2651-2673), in the case of safracin synthetases, the TE domain is missing. Probably, in the safracin synthesis after the last elongation step, the tetrapeptide could be released by an alternative strategy for peptide-chain termination that also occurs in the saframycin synthesis (Pospiech et al. *Microbiol.* 1996, 142, 741-746). This particular termination strategy is catalysed by a reductase domain at the carboxy-terminal end of the SacC peptide synthetase which catalyses the reductive cleavage of the associated T-domain-tethered acyl group, releasing a linear aldehyde.

Figure 4:
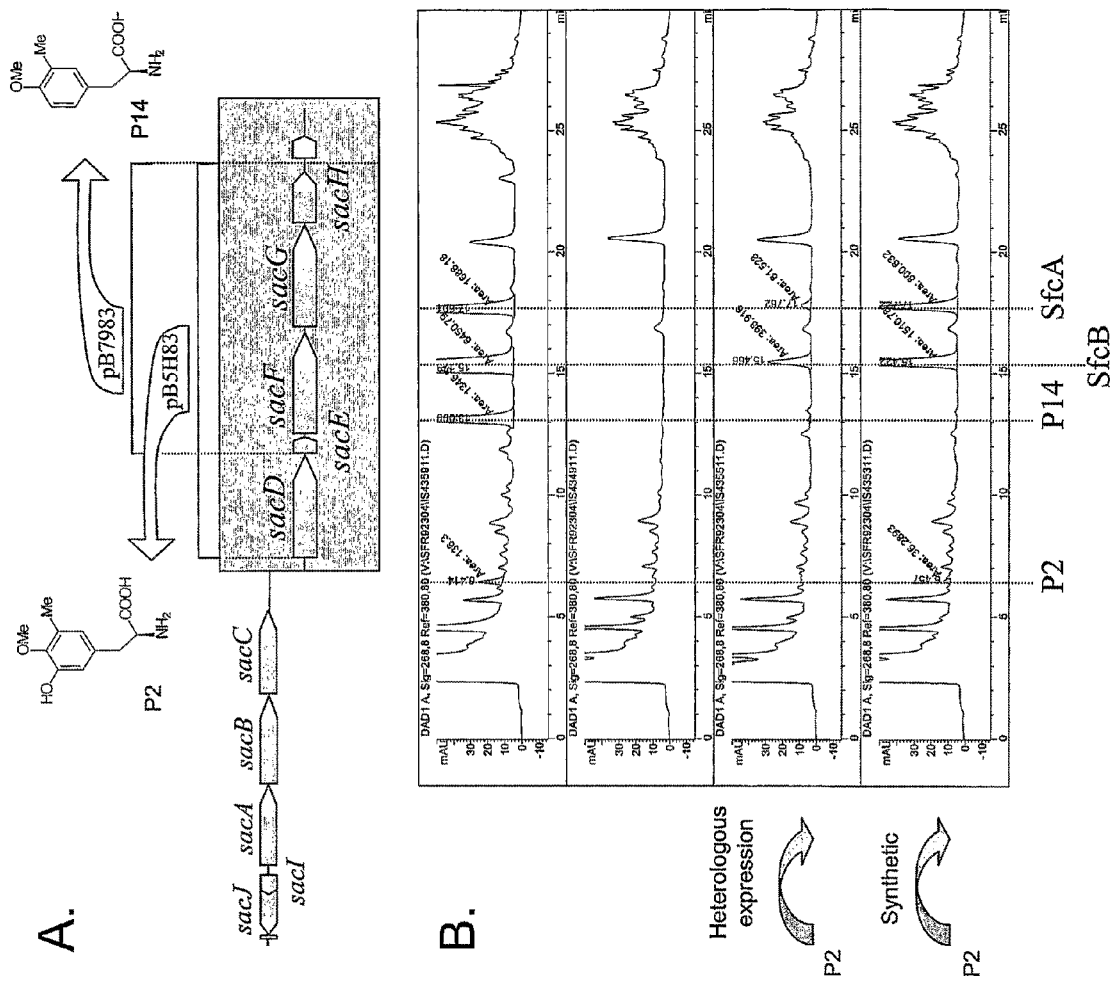
FIG. 4: Cross-feeding experiments. A. Scheme of A2-2 DNA fragments cloned in pBBR1-MCS2 vector and products obtained in the heterologous host. B. HPLC profile of safracin production in wild type strain versus sacF mutant. The addition of P2 precursor to the sacF mutant, provided both in trans and synthetically, yield safracin B production. SfcA, safracin A and SfcB, safracin B.
Figure 5:
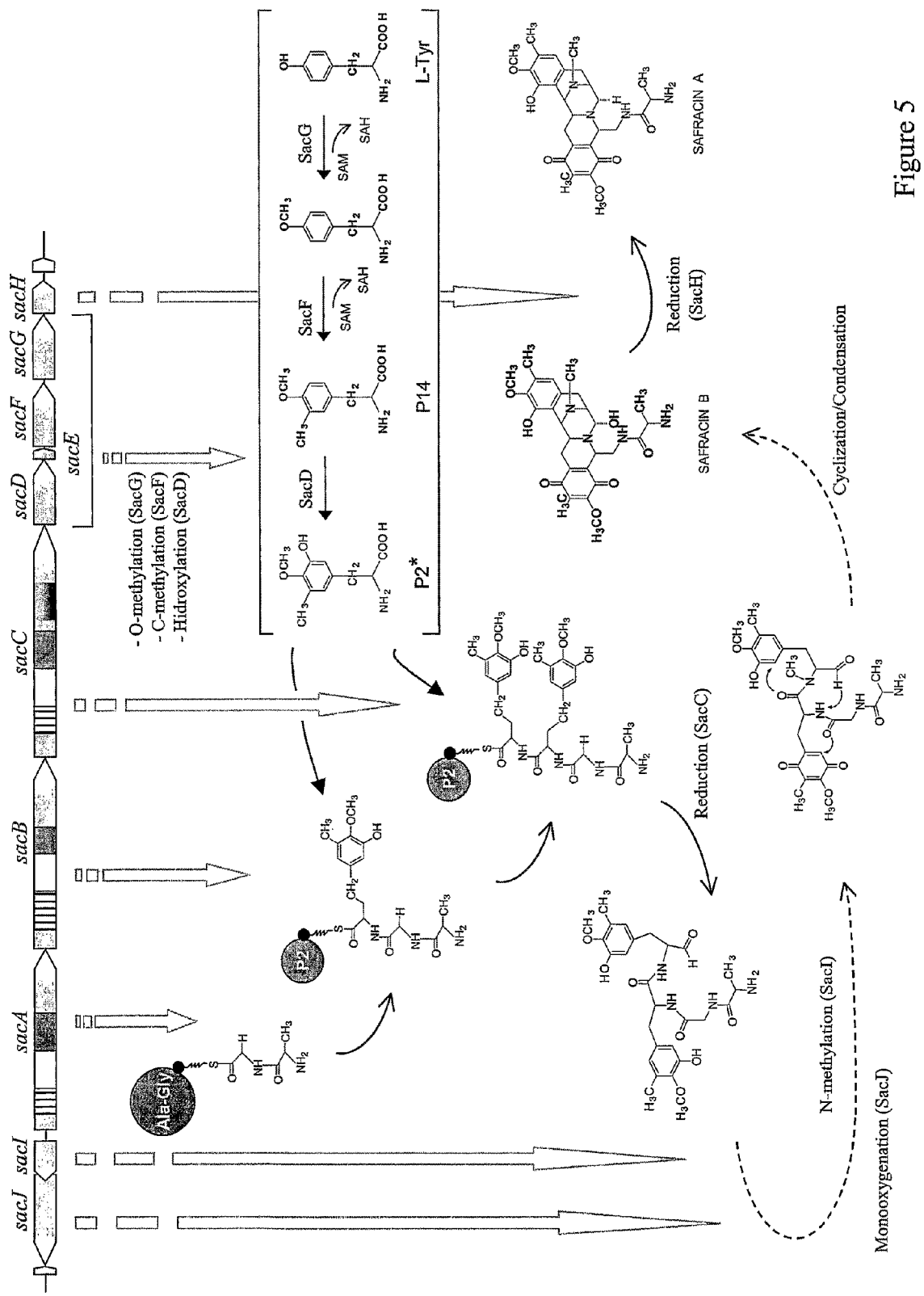
FIG. 5: Scheme of the safracin biosynthesis mechanism and biosynthetic intermediates. Single enzymatic steps are indicated by a continuous arrow and multiple reactions steps are indicated by discontinuous arrows.

Our cross feeding experiments indicate that the last two amino acids incorporated into the safracin molecule are two L-Tyr derivatives called P2 (3-hydroxy-5-methyl-O-methyl-tyrosine) (FIGS. 4, 5), instead of two L-Tyr as it is proposed to occur in saframycin synthesis. First, the products of two genes (sacF and sacG), similar to bacterial methyltransferases, have shown to be involved in the O-, C-methylation of L-Tyr to produce P14 (3-methyl-O-methyltyrosine), precursor of P2. A possible mechanism could envisage that the O-methylation occurs first and then the C-methylation of the amino acid derivative is produced. Secondly, P2, the substrate for the peptide synthetases SacB and SacC, is formed by the hydroxylation of P14 by SacD (FIGS. 4, 5).

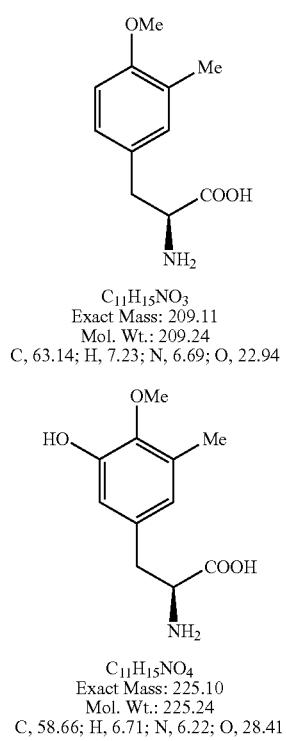

P-14

$C_{11}H_{15}NO_3$
Exact Mass: 209.11
Mol. Wt.: 209.24
C, 63.14; H, 7.23; N, 6.69; O, 22.94

P-2

$C_{11}H_{15}NO_4$
Exact Mass: 225.10
Mol. Wt.: 225.24
C, 58.66; H, 6.71; N, 6.22; O, 28.41

Apart from the safracin biosynthetic genes, in the sacAB-CDEFGH operon there are also found two genes, sacE and sacH, involved in an unknown function and in the safracin resistance mechanism, respectively. We have demonstrated that sacH gene codes for a protein that when is heterologous expressed, in different *Pseudomonas* strains, a highly increase of the safracin B resistance is produced. SacH is a putative transmembrane protein, that transforms the $C_{21}$—OH group of safracin B into a $C_{21}$—H group, to produce safracin A, a compound with less antibiotic and antitumoral activity. Finally, even though still is unknown about the putative function of SacE, homologous of this gene have been found close to various secondary metabolites biosynthetic gene clusters in some microorganisms genomes, suggesting a conserved function of this genes in secondary metabolite formation or regulation.

In the sacIJ operon, the deduced amino acid sequences encoded by sacI and sacJ strongly resemble gene products of methyltransferase and hydroxylase/monoxygenase, respectively. Our data reveals that SacI is the enzyme responsible for the N-methylation present in the safracin structure, and that SacJ is the protein which makes an additional hydroxylation on one of the L-Tyr derivative incorporated into the tetrapeptide to produce the quinone structure present in all safracin molecules. N-Methylation is one of the modifications of non-ribosomally synthesized peptides that significantly contributes to their biological activity. Except for saframycin (Pospiech et al. *Microbiol.* 1996, 142, 741-746), that is produced by bacteria and is N-methylated, all the N-methylated nonribosomal peptides known are produced by fungi or actinomycetes and, in most of the cases, the responsible for the N-methylation is a domain which reside in the nonribosomal peptide synthetase.

TABLE I

Summary of safracin biosynthetic and resistance genes identified in cosmid pL30P.

| ORF name | Protein name | Proposed function | Position start-stop bp | Amino acids | Molecular weight |
|---|---|---|---|---|---|
| sacA | SacA | Peptide synthetase | 3052-6063 | 1004 | 110.4 |
| sacB | SacB | Peptide synthetase | 6068-9268 | 1063 | 117.5 |
| sacC | SacC | Peptide synthetase | 9275-13570 | 1432 | 157.3 |
| sacD | SacD | L-Tyr derivative hidroxylase | 13602-14651 | 350 | 39.2 |
| sacE | SacE | Unknown | 14719-14901 | 61 | 6.7 |
| sacF | SacF | L-Tyr derivative methylase | 14962-16026 | 355 | 39.8 |
| sacG | SacG | L-Tyr O-methylase | 16115-17155 | 347 | 38.3 |
| sacH | SacH | Resistance protein | 17244-17783 | 180 | 19.6 |
| sacI | SacI | methyl-transferase | 2513-1854 | 220 | 24.2 |
| sacJ | SacJ | monooxygenase | 1861-355 | 509 | 55.3 |

The safracin putative synthetic pathway, with indications of the specific amino acid substrates used for each condensation reaction and the various post-condensation activities, is shown in FIG. 5.

Figure 6:
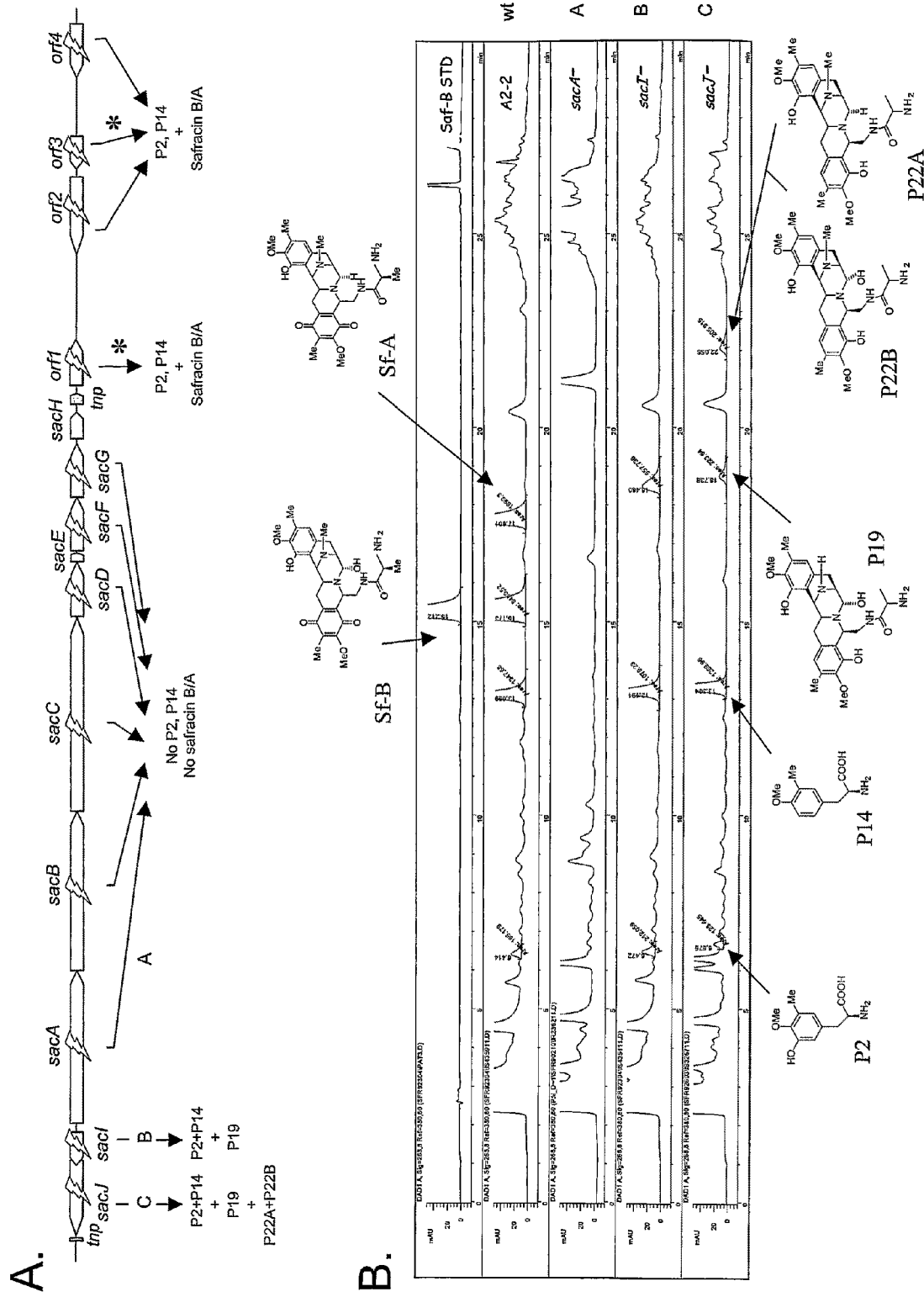
FIG. 6: Safracin gene disruptions and compounds produced. A. Gene disruption and precursor molecules synthesized by the mutants constructed. Gene marked With an asterisk does not belong to the safracin cluster. Inactivation of genes orf1, orj2, orf3 and orf4 has demonstrated to have no effect over safracin production. B. HPLC profile of safracin production in wild type strain and in sacA, sacI and sacJ mutants. Structure of the different molecules obtained is shown.

To further evaluate the role of safracin biosynthetic genes, we constructed knock out mutants of each of the genes of the safracin cluster (FIG. 6). The disruption of the NRPSs genes (sacA, sacB and sacC) as well as sacD, sacF and sacG, resulted in safracin and P2 non producing mutants. Our results indicate that the genes from sacA to sacH are part of the same genetic operon. As a consequence of the sacI and sacJ gene disruptions three new molecules were originated, P19B, P22A and P22B (FIG. 6).

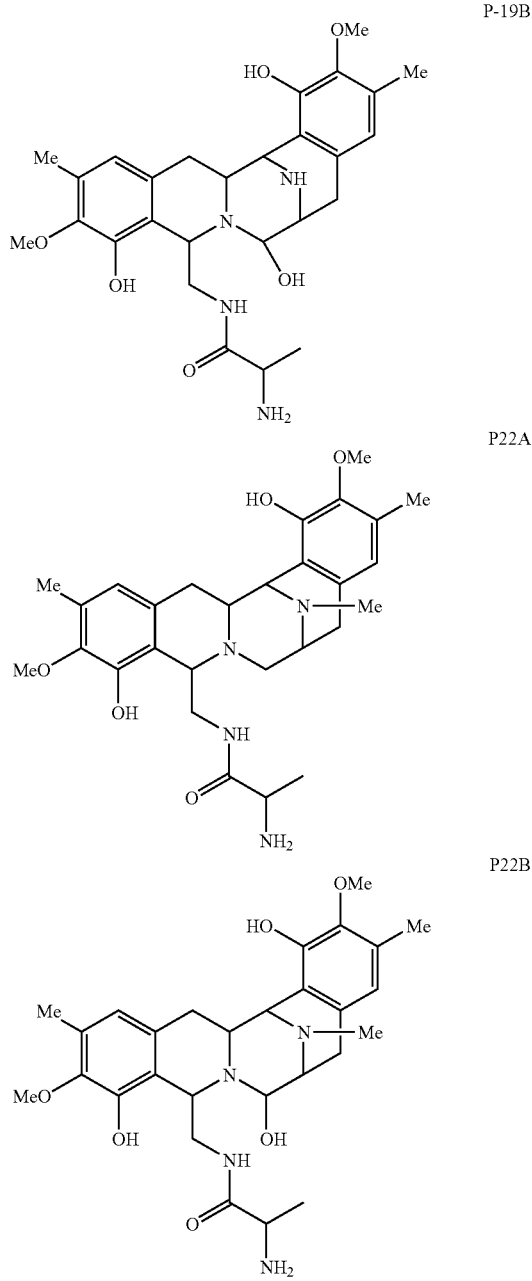

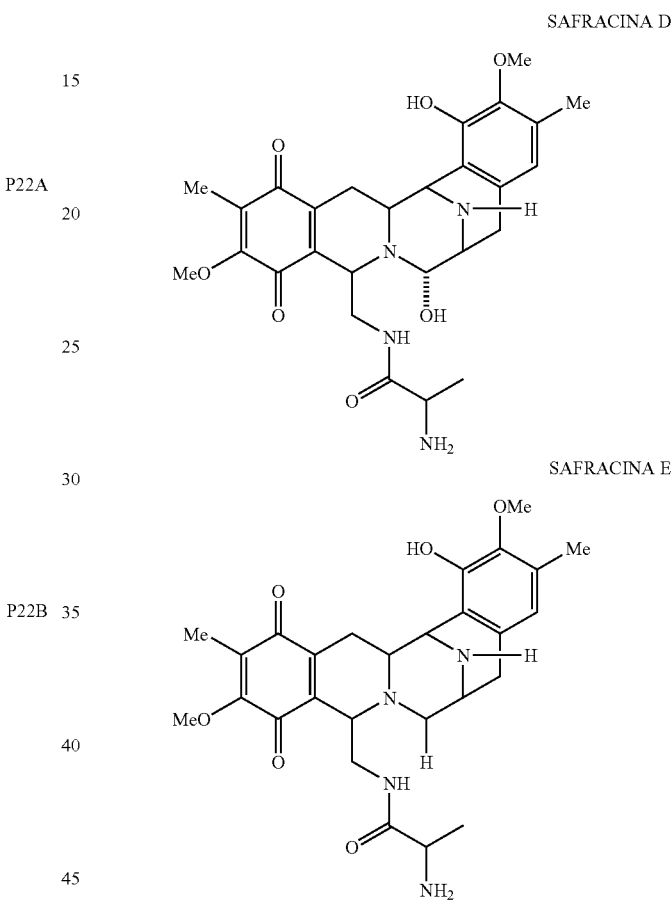

The production of P22A and P22B (FIG. 7a*) by sacJ mutant demonstrated that the role of the SacJ protein is to produce the additional hydroxylation of the left L-Tyr derivatives amino acid of the safracin, the one involved in the quinone ring. The production of P19B (FIG. 7b*) by sacI mutant, a safracin like molecule where the N-methylation and the quinone ring are missing, confirms that SacI is the N-methyltransferase enzyme and suggests that sacIJ is a transcriptional operon. The production of P19B also by sacJ mutant (FIG. 7a*) suggests that probably the N-methylation occurs after the quinone ring has been formed. Even though these new structures have no interesting antimicrobial activity on B. subtilis or no high citotoxic activity on cancer cells, they can serve as interesting new precursors for the hemisynthesis of new active molecules. As far as structure activity is concerned, the observation that P19B, P22A and P22B appear to loose their activity, suggests that the lost of the quinone ring from the safracin structure is directly related with the lost of activity of the safracin family molecules.

Figure 7:
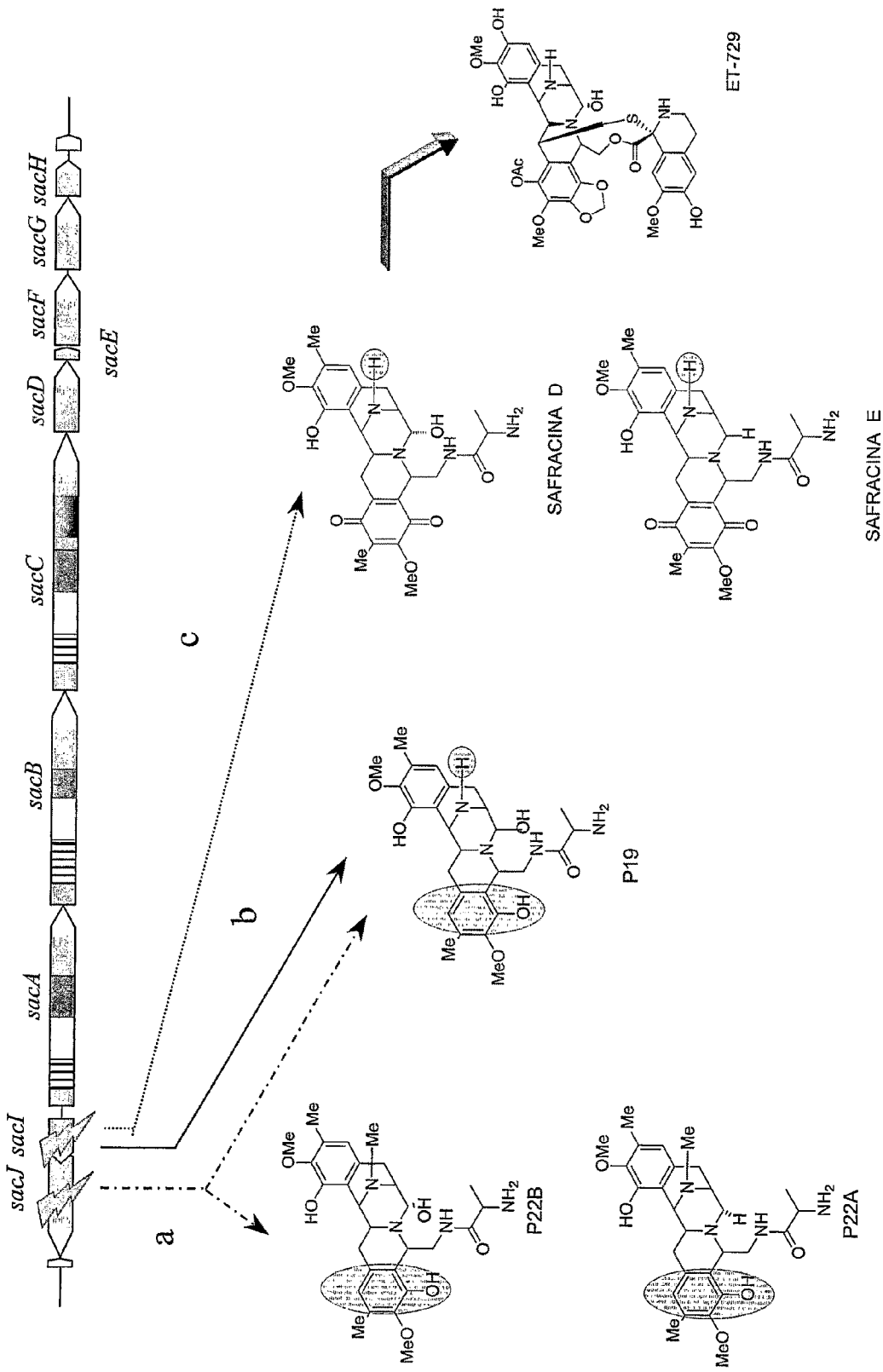
FIG. 7: Structure of the different molecules obtained by gene disruption. Inactivation of SacJ protein (a) yields P22B, P22A and P19 molecules, whereas gene disruption of sacI (b), produces only P19 compound. The sacI disruption, together with the sacJ reconstructed expression, produces two new safracins: safracin D (possible precursor for ET-729 hemi-synthesis) and safracin E (c).

The disruption of sacI gene with the reconstitution of the sacJ gene expression resulted in the production of two new safracins. The two antibiotics produced, at levels of production as high as the levels of safracin A/safracin B production in the wild type strain, have been named as safracin D and safracin E (FIG. 7c*).

The safracin D and safracin E are safracin B and safracin A like molecules, respectively, where the N-methylation is missing. Both, safracin D and safracin E have been shown to possess the same antibacterial and antitumoral activities as safracin B and safracin A, respectively. Apart from its high activities properties, antibacterial and antitumoral, safracin D could be used in the hemi-synthesis of the ecteinascidin ET-729, a potent antitumoral agent, as well as in the hemi-synthesis of new ecteinascidins.

A question arises concerning the role of the aminopeptidase-like protein coded by a gene located at 3'site of the safracin operon. The insertional inactivation of orf1 (PM-S1-14) showed no effect on safracin A/safracin B production. Because of its functionality properties it remains unclear if this protein could play some role in the safracin metabolism. The other genes present in the pL30P cosmid (orf2 to orf4) will have to be studied in more detail.

Another aspect of the invention is that it provides the tools necessary for the production of new specific designed "unnatural" molecules. The addition of a specific modified P2 derivative precursor named P3, a 3-hydroxy-5-methyl-O-ethyltyrosine, to the sacF mutant yields two "unnatural" safracins that incorporated this specific modified precursor, safracin A(OEt) and safracin B(OEt) (FIG. 8).

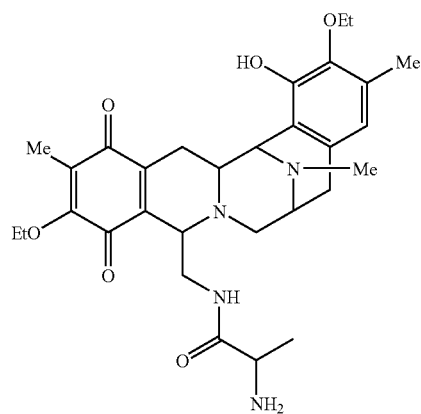

safracin A(OEt)

$C_{30}H_{40}N_4O_6$
Exact Mass: 552.29
Mol. Wt.: 552.66
C, 65.20; H, 7.30; N, 10.14; O, 17.37

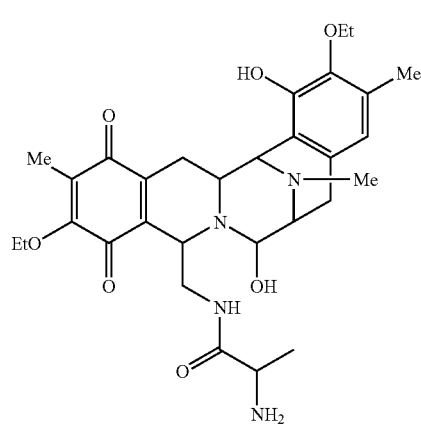

safracin B(OEt)

$C_{30}H_{40}N_4O_7$
Exact Mass: 568.29
Mol. Wt.: 568.66
C, 63.36; H, 7.09; N, 9.85; O, 19.69

The two new safracins are potent antibiotic and antitumoral compounds. The biological activities of safracin A(OEt) and Safracin B(OEt) are as potent as the activities of safracin A and safracin B, respectively. These new safracins could be the source for new potent antitumoral agents, as well as a source of molecules for the hemi-synthesis of new ecteinascidins.

In addition, the genes involved in safracin synthesis could be combined with other non ribosomal peptide synthetases genes to result in the creation of novel "unnatural" drugs and analogs with improved activities.

EXAMPLES

Example 1

Extraction of Nucleic Acid Molecules from *Pseudomonas fluorescens* A2-2

Bacterial Strains

Strains of *Pseudomonas* sp. were grown at 27° C. in Luria-Bertani (LB) broth (Ausubel et al. 1995, J. Wiley and Sons, New York, N.Y). *E. coli* strains were grown at 37° C. in LB medium. Antibiotics were used at the following concentrations: ampicillin (50 μg/ml), tetracycline (20 μg/ml) and kanamycin (50 μg/ml).

TABLE II

| Strains used in this invention. | |
|---|---|
| Code | Genotype |
| PM-S1-001 | *P. fluorescens* A2-2 wild type |
| PM-S1-002 | sacA- |
| PM-S1-003 | sacB- |
| PM-S1-004 | sacC- |
| PM-S1-005 | sacJ- |
| PM-S1-006 | sacI- |
| PM-S1-007 | sacI- with sacJ expression reconstitution |
| PM-S1-008 | sacF- |
| PM-S1-009 | sacG- |
| PM-S1-010 | sacD- |
| PM-S1-014 | orf1- |
| PM-S1-015 | A2-2 + pLAFR3 |
| PM-S1-016 | A2-2 + pL30p |
| PM-19-001 | *P. fluorescens* CECT378 + pLAFR3 |
| PM-19-002 | *P. fluorescens* CECT378 + pL30p |
| PM-19-003 | *P. fluorescens* CECT378 + pBBR1-MCS2 |
| PM-19-004 | *P. fluorescens* CECT378 + pB5H83 |
| PM-19-005 | *P. fluorescens* CECT378 + pB7983 |
| PM-19-006 | *P. fluorescens* CECT378 + pBHPT3 |
| PM-16-001 | *P. aeruginosa* CECT110 + pLAFR3 |
| PM-16-002 | *P. aeruginosa* CECT110 + pL30p |
| PM-17-003 | *P. putida* ATCC12633 + pBBR1-MCS2 |
| PM-17-004 | *P. putida* ATCC12633 + pB5H83 |
| PM-17-005 | *P. putida* ATCC12633 + pB7983 |
| PM-18-003 | *P. stutzeri* ATCC17588 + pBBR1-MCS2 |
| PM-18-004 | *P. stutzeri* ATCC17588 + pB5H83 |
| PM-18-005 | *P. stutzeri* ATCC17588 + pB7983 |

DNA Manipulation

Unless otherwise noted, standard molecular biology techniques for in vitro DNA manipulations and cloning were used (Sambrook et al. 1989, Cold Spring Harbor, N.Y.: Cold Spring Harbor Laboratory).

DNA Extraction

Total DNA from *Pseudomonas fluorescens* A2-2 cultures was prepared as reported (Sambrook et al. 1989, Cold Spring Harbor, N.Y.: Cold Spring Harbor Laboratory).

Computer Analysis

Sequence data were compiled and analysed using DNA-Star software package.

Example 2

Identification of NRPS Genes Responsible for Safracin Production in *Pseudomonas fluorescens* A2-2

Primer Design

Marahiel et at. (Marahiel et at. *Chem. Rev.* 1997, 97, 2651-2673) previously reported highly conserved core motifs of the catalytic domains of cyclic and branched peptide synthetases. Based on multiple sequence alignments of several reported peptide synthetases the conserved regions A2, A3, A4, A6, A7 and A8 of adenylation and T of thiolation modules were targeted for the degenerate primer design (Turgay and Marahiel, *Peptide Res.* 1994, 7, 238-241). The wobble positions were designed in respect to codon preferences within the selected modules and the expected high G/C content of *Pseudomonas* sp. All oligonucleotides were obtained from ISOGEN (Bioscience BV). A PCR fragment was obtained when degenerate oligonucleotides derived from the YGPTE (SEQ ID NO: 35) (A5 core) and LGGXS (SEQ ID NO: 19) (T core) sequences were used. These oligonucleotides were denoted PS34-YG and PS6-FF, respectively.

TABLE III

PCR primers designed for this study.
(SEQ ID NOS: 20 and 21,
respectively, in order of appearance)

| Primer designation and orientation | Sequence | Length |
|---|---|---|
| PS34-YG (forward) | 5'-TAYGGNCCNACNGA-3' | 14-mer |
| PS6-FF (reverse) | 5'-TSNCCNCCNADNTCRAARAA-3' | 20-mer |

PCR Conditions for Amplification of DNA from *P. fluorescens* A2-2

A fragment internal to nonribosomal peptide synthetases (NRPS) was amplified using PS-34-YG and PS6-FF oligonucleotides and *P. fluorescens* A2-2 chromosomal DNA as template. Reaction buffer and Taq polymerase from Promega were used. The cycling profile performed in a Personal thermocycler (Eppendorf) consists on: 30 cycles of 1 min at 95° C., 1 min at 50° C., 2 min at 72° C. PCR products were on the expected size (750 bp aprox.) based on the location of the primers within the NRPS domains of other synthetase genes.

DNA Cloning

PCR amplification fragments were cloned into pGEM-Teasy vector according to the manufacturer (Qiagen, Inc., Valencia, Calif.). In this way, cloned fragments are flanked by two EcoRI restriction sites, in order to facilitate subsequent subclonig in other plasmids (see below). Since NRPSs enzymes are modular, clones from the degenerated PCR primers represents a pool of fragments from different domains.

DNA Sequencing

All sequencing was performed using primers directed against the cloning vector, with an ABI Automated sequencer (Perkin-Elmer). Cloned DNA sequences were identified using the BLAST server of the National Center for Biotechnology Information accessed over the Internet (Altschul et al., *Nucleic Acids Res.* 1997, 25, 3389-3521). All of the sequences have signature regions for NRPSs and show high similarity in BLAST searches to bacterial NRPS showing that they are in fact of peptide origin. Moreover, a probable domain similarity search was performed using the PROSITE (European Molecular Biology Laboratory, Heidelberg, Germany) web server.

Gene Disruption of *Pseudomonas fluorescens* A2-2

Figure 9:
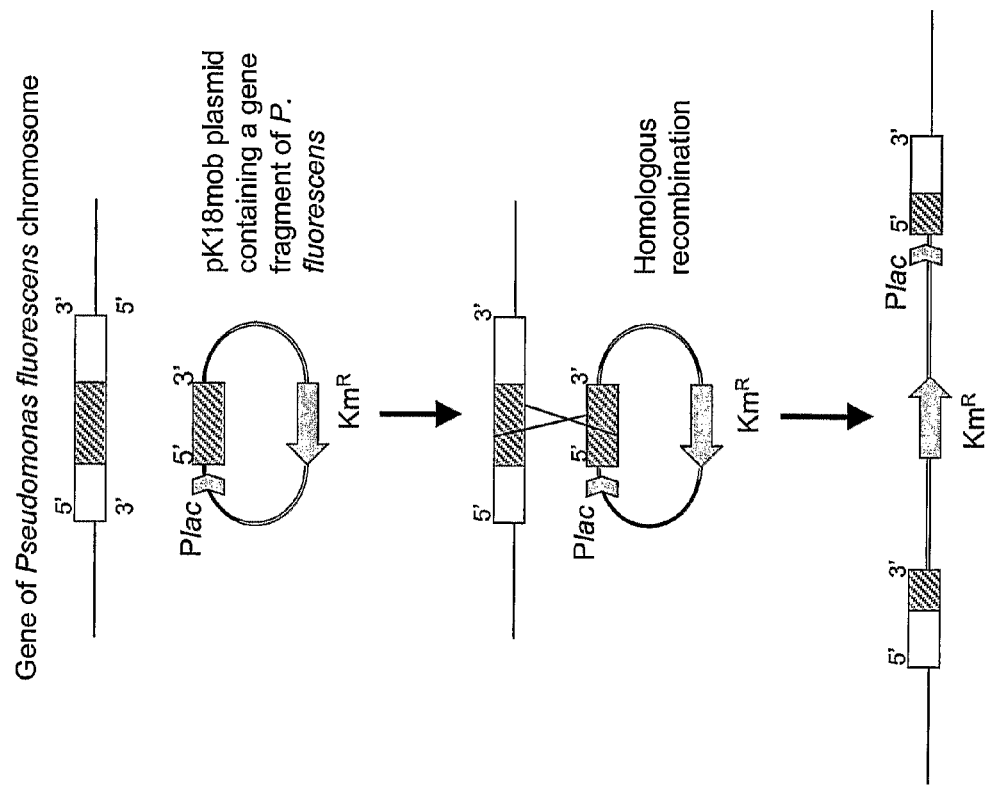
FIG. 9: Scheme of the gene disruption event through simple recombination, using an homologous DNA fragment cloned into pK18:MOB (an integrative plasmid in Pseudomonas).

In order to analyse the function of the genes cloned, these genes were disrupted through homologous recombination (FIG. 9). For this purpose, recombinant plasmids (pG-PS derivatives) harbouring the NRPS gene fragment were digested with EcoRI restriction enzyme. The resulting fragments belonging to the gene to be mutated were cloned into the pK18mob mobilizable plasmid (Schäfer et al. *Gene* 1994, 145, 69-73), a chromosomal integrative plasmid able to replicate in *E. coli* but not in *Pseudomonas* strains. Recombinant plasmids were introduced first in *E. coli* S17-λPIR strain by transformation and then in *P. fluorescens* A2-2 through biparental conjugation (Herrero et al, *J Bacteriol* 1990, 172, 6557-6567). Different dilutions of the conjugation were plated onto LB solid medium containing ampicillin plus kanamycin and incubated overnight at 27° C. Kanamycin-resistant transconjugants, containing plasmids integrated into the genome via homologous recombination, were selected.

Biological Assay (biotest) for Safracin Production

Strains *P. fluorescens* A2-2 and its derivatives were incubated in 50 ml baffled erlenmeyer flasks containing fermentation medium with the corresponding antibiotics. Initially, SA3 fermentation medium was used (Ikeda Y. *J. Ferment. Technol.* 1985, 63, 283-286). In order to increase the productivity of the fermentation process statistical-mathematical methods like Plackett-Burman designed was used to select nutrients and response surface optimisation techniques were tested (Hendrix C. *Chemtech* 1980, 10, 488-497) in order to determine the optimum level of each key independent variable. Experiments to improve the culture conditions like incubation temperature and agitation have also been done. Finally a highly safracin B producer medium named 16B (152 g/l of mannitol, 35 g/l of G20-25 yeast, 26 g/l of $CaCO_3$, 14 g/l of ammonium sulphate, 0.18 g/l of ferric chloride, pH 6.5) was selected.

The safracin production was assay testing the capacity of inhibition a *Bacillus subtilis* solid culture by 10 μl of the supernatant of a 3 days *Pseudomonas* sp. culture incubated at 27° C. (Alijah et al. *Appl Microbiol Biotechnol* 1991, 34, 749-755). *P. fluorescens* A2-2 cultures produce inhibition zones of 10-14 mm diameter while non-producing mutants did not inhibit *B. subtilis* growth. Three isolated clones had the safracin biosynthetic pathway affected. In order to confirm the results, HPLC analysis of safracin production was performed.

HPLC Analysis of Safracin Production

The supernatant was analysed by using HPLC Symmetry C-18. 300 Å, 5 μm, 250×4.6 mm column (Waters) with guard-column (Symmetry C-18, 5 μm 3.9×20 mm, Waters). An ammonium acetate buffer (10 mM, 1% Diethanolamine, pH 4.0)-acetonitrile gradient was the mobile phase. Safracin was detected by absorption at 268 nm. In FIG. 6, HPLC profile of safracin and safracin precursors produce by *P. fluorescens* A2-2 strain and different safracin-like structures produced by *P. fluorescens* mutants are shown.

Example 3

Cloning and Sequence Analysis of Safracin Cluster

Inverse PCR and Phage Library Hybridisation

Southern hybridisation on mutant chromosomal DNAs verified the correct gene disruption and demonstrated that the peptide synthethase fragment cloned into pK18mob plasmid was essential for the production of safracin. Analysis of the non safracin producers mutants obtained demonstrated that all of them had a gene disruption into the same gene, sacA.

Inverse PCR from genomic DNA and screening of a phage library of *P. fluorescens* A2-2 genomic DNA revealed the presence of additional genes flanking sacA gene, probably involved in safracin biosynthesis.

The GenBank accession number for the nucleotide sequence data of the *P. fluorescens* A2-2 safracin biosynthetic cluster is AY061859.

Cosmid Library Construction and Heterologous Expression

To determine whether safracin cluster was able to confer safracin biosynthetic capability to a non producer strain, it was cloned into a wide range cosmid vector (pLAFR3, Staskawicz B. et al. *J Bacteriol* 1987, 169, 5789-5794) and conjugated to a different *Pseudomonas* sp collection strains.

To obtain a clone containing the whole cluster, a cosmid library was constructed and screened. For this purpose, chromosomal DNA was partially digested with the restriction enzyme PstI, the fragments were dephosphorylated and ligated into the PstI site of cosmid vector pLAFR3. The cosmids were packaged with Gigapack III gold packaging extracts (Stratagene) as manufacturer's recommendations. Infected cells of strain XL1-Blue were plated on LB-agar supplemented with 50 µg/ml of tetracycline. Positives clones were selected using colony hybridization with a DIG-labeled DNA fragment belonging to the 3'-end of the safracin cluster. In order to ensure the cloning of the whole cluster, a new colony hybridization with a 5'-end DNA fragment was done. Only cosmid pL30p showed multiple hybridizations with DNA probes. To confirm the accurate cloning, PCR amplification and DNA-sequencing with DNA oligonucleotides belonging to the safracin sequence were carried out. The size of the insert of pL30P was 26,705 bp. The pL30p clone DNA was transformed into *E. coli* S17λPIR and the resulting strain were conjugated with the heterologous *Pseudomonas* sp. strains. The pL30p cosmid was introduced into *P. fluorescens* CECT378 and *P. aeruginosa* CECT110 by biparental conjugation as described above. Once a clone encoding the whole cluster was identified, it was determined whether the candidate was capable of producing safracin. Safracin production in the conjugated strains was assessed by HPLC analysis and biological assay of broth cultures supernatants as previously described.

The strain *P. fluorescens* CECT378 expressing the pL30p cosmid (PM-19-002) was able to produce safracin in considerable amounts, whereas safracin production in *P. aeruginosa* CECT110 strain expressing pL30P (PM-16-002) was 10 times less than the CECT378. Safracin production in these strains was about 22% and 2% of the total production in comparison with the natural producer strain.

Genes Involved in the Formation of Safracin. SEQUENCE Analysis of sacABCDEFGH and sacIJ Operons Computer analyses of the DNA sequence of pL30P revealed 14 ORFs (FIG. 1). A potential ribosome binding site precedes each of the ATG start codons.

In the sacABCDEFGH operon, three very large ORFs, sacA, sacB and sacC (positions 3052 to 6063, 6080 to 9268 and 9275 to 13570 of the *P. fluorescens* A2-2 safracin sequence SEQ ID NO: 1, respectively) can be read in the same direction and encode the putative safracin NRPSs: SacA (1004 amino acids, $M_r$ 110452), SacB (1063 amino acids, $M_r$ 117539) and SacC (1432 amino acids, $M_r$ 157331). The three NRPSs genes contain the domains resembling amino acid activating domains of known peptide synthetases. Specifically, the amino acid activating domains from these NRPS genes are very similar to three of the four amino acid activating domains (Gly, Tyr and Tyr) found in the *Myxococcus xanthus* saframycin NRPSs (Pospiech et al. *Microbiology* 1995, 141, 1793-803; Pospiech et al. *Microbiol.* 1996, 142, 741-746). In particular, SacA (SEQ ID NO:2) shows 33% identity with saframycin Mx1 synthetase B protein (SafB) from *M. xanthus* (NCBI accession number U24657), whereas SacB (SEQ ID NO:3) and SacC (SEQ ID NO:4) share, respectively, 39% and 41% identity with saframycin Mx1 synthetase A (SafA) from *M. xanthus* (NCBI accession number U24657). The FIG. 2 shows a comparison among SacA, SacB y SacC and the different amino acid activating domains of saframycin NRPS.

Downstream sacC five small ORFs reading in the same direction as the NRPSs genes exist (FIG. 1). The first one, sacD (position 13602 to 14651 of *P. fluorescens* A2-2 safracin sequence), encodes a putative protein, SacD (350 amino acids, $M_r$ 39187; SEQ ID NO:5), with no similarities in the GeneBank DB. The next one, sacE (position 14719 to 14901 of *P. fluorescens* A2-2 safracin sequence), encodes a small putative protein called SacE (61 amino acids, $M_r$ 6729; (SEQ ID NO:6)), which shows some similarity with proteins of unknown function in the databases (ORF1 from *Streptomyces viridochromogenes* (NCBI accession number Y17268; 44% identity) and MbtH from *Mycobacterium tuberculosis* (NCBI accession number Z95208; 36% identity). The third ORF, sacF (position 14962 to 16026 of *P. fluorescens* A2-2 safracin sequence), encodes a 355-residue protein with a molecular weigh calculated of 39,834 (SEQ ID NO:7). This protein most closely resembles hydroxyneurosporene methyltransferase (CrtF) from *Chloroflexus aurantiacus* (NCBI accession number AF288602; 25% identity). The nucleotide sequence of the fourth ORF, sacG (position 16115 to 17155 of *P. fluorescens* A2-2 safracin sequence), predicted a gene product of 347 amino acids having a molecular mass of 38,22 kDa (SEQ ID NO:8). The protein, called SacG, is similar to bacterial O-methyltransferases, including O-dimethylpuromycin-O-methyltransferase (DmpM) from *Streptomyces anulatus* (NCBI accession number P42712; 31% identity). A computer search also shows that this protein contains the three sequence motifs found in diverse S-adenosylmethionine-dependent methytransferases (Kagan and Clarke, *Arch Biochem. Biophys.* 1994, 310, 417-427). The fifth gene, sacH (position 17244 to 17783 of *P. fluorescens* A2-2 safracin sequence), encodes a putative protein SacH (180 amino acids, $M_r$ 19632; (SEQ ID NO:9). A computer search for similarities, between the deduced amino acid sequence of SacH and other protein sequences, revealed identity with some conserved hypothetical proteins of unknown function, which contains a well conserved transmembrane motif and a dihydrofolate reductase-like active site (Conserved hypothetical protein from *Pseudomonas aeruginosa* PAO1, NCBI accession number P3469; 35% identity).

Upstream sacABCDEFGH operon, reading in opposite sense, a two genes operon, sacIJ, is located. The sacI gene (position 2513 to 1854) encodes a 220-amino acids protein ($M_r$ 24219; (SEQ ID NO: 10) that most closely resembles ubiquinone/manequinone methyltrasnferase from *Thermotoga maritime* (NCBI accession number AE001745; 32% identity). The sacJ gene (position 1861 to 335) encodes a 509-amino acid protein (SEQ ID NO:11), with a molecular mass of 55341 Da, similar to bacterial monooxygenases/hydroxylases, including putative monooxygenase from *Bacillus subtilis* (NCBI accession number Y14081; 33% identity) and *Streptomyces coelicolor* (NCBI accession number AL109972; 29% identity).

SacABCDEFGH and sacIJ operons are transcribed divergently and are separated by 450 bp approximately. Both operons are flanked by residual transposase fragments.

Related Safracin Cluster Genes

A putative ORF (orf1; position 18322 to 19365 of *P. fluorescens* A2-2 safracin sequence) located at the 3'-end of the safracin sequence has been found (FIG. 1). ORF1 protein (SEQ ID NO:12) shows similarity with aminopeptidases from the Gene Bank DataBase (peptidase M20/M25/M40 family from *Caulobacter crescentus* CB15; NCBI accession number NP422131; 30% identity). Using the strategy described in Example 2, the gene disruption of orf1 do not affect safracin production in *P. fluorescens* A2-2.

At the 3'-end of the safracin sequence cloned in pL30p cosmid, three putative ORFs (orf2, orf3 and orf4), were found. Reading in opposite direction than sacABCDEFGH operon, orf2 gene (position 22885 to 21169 of SEQ ID NO:1) codes for a protein, ORF2 (SEQ ID NO:13), with similarities to *Aquifex aeolicus* HoxX sensor protein (NCBI accession number NC000918.1; 35% identity), whereas orf3 gene (position 23730 to 23041 of SEQ ID NO:1) codes for ORF3 protein (SEQ ID NO:14) which shares 44% identity with a glycosil transferase related protein from *Xanthomonas axonopodis* pv. *Citri* str. 306 (NCBI accession number NP642442).

The third gene is located at the 3'-end of SEQ ID NO:1 (position 25037 to 26095). This gene, named orf4 (position 2513 to 1854), encodes a protein, ORF4 (SEQ ID NO:15), that most closely resembles to a hypothetical isochorismatase family protein YcdL from *Escherichia coli*. (NCBI accession number P75897; 32% identity).

Presumably, these three genes would not be involve in the safracin biosynthetic pathway, however, future gene disruption of these genes will confirm this assumption.

The different DNA sequences found are listed at the end of the description.

Example 4

Functional Analysis of the Safracin Loci and Search for Possible Precursors

Since the pathway for synthesis of safracin in *P. fluorescens* A2-2 is at present unknown, the inactivation of each of the genes described in Example 3 would permit fundamental studies on the mechanism of safracin biosynthesis in this strain.

In order to analyze the functionality of each particular protein in the safracin production pathway, disruption of each particular gene of the cluster, but sacE, was performed. All of the genetic mutants were obtained following the disruption strategy previously described.

FIG. 6 is a summary of the different mutants constructed in this invention as well as a summary of the compounds produced by the mutants as a consequence of the gene disruption. In the wild type strain both safracin A and B and other compounds, P2 and P14, were clearly detected by HPLC (see FIG. 6,WT). The gene disruption of the saca (PM-S1-002), sacB (PM-S1-003), sacC (PM-S1-004), sacD (PM-S1-010), sacF (PM-S1-008), and sacG (PM-S1-009), genes generated mutants that were unable to produce neither safracin A and safracin B, nor the precursor compounds with retention times beneath 15 min, P2 and P14 respectively. The structure elucidation of P14 and P2 revealed that P14 is a 3-methyl-O-methyl tyrosine, where as P2 is a 3-hydroxy-5-methyl-O-methyl tyrosine. Because of the small size of the sacE gene, the sacE$^-$ mutant was not possible to be obtained by gene disruption, but deletion of this gene is in process. The overexpression of SacE protein, in trans, had no effect on safracin B/A production. The sacI$^-$ mutants (PM-S1-006) produced P2, P14 and significant amount of a compound called P19B (FIG. 6; FIG. 7b*). Structure elucidation of P19B revealed that this compound is a safracin-like molecule in which the N-Met and one of the OH from the quinone ring are missing. In the sacJ$^-$ mutants (PM-S1-005), P2, P14, P19B and two new compounds called P22A and P22B were obtained (FIG. 6; FIG. 7a*). Structure elucidation of P22A and P22B revealed that they are safracin A and safracin B like molecules, respectively, without one of the —OH group from the quinone ring. The biological assay of the sacI$^-$ and the sacJ$^-$ mutants extracts revealed very low activity against *Bacillus subtilis*.

The disruption of sacI gene with the reconstitution of the sacJ gene expression resulted in a new safracins producer mutant, PM-S1-007. The two antibiotics produced, at levels of production as high as the levels of safracin A and safracin B in the wild type strain, have been named as safracin D and safracin E (FIG. 7c*). The safracin D and safracin E are safracin B and safracin A like molecules, respectively, where the N-methylation is missing.

These results strongly suggest that i) sacA, sacB and sacC genes encode for the safracin NRPSs; ii) sacD, sacF and sacG genes are responsible for the transformation of L-Tyr into the L-Tyr derivative P2 and iii) sacI and sacJ are responsible for the tailoring modifications that convert P19 and P22 into safracin.

Characterization of Natural Precursors:

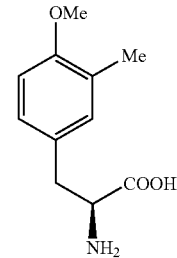

P-14

$C_{11}H_{15}NO_3$
Exact Mass: 209.11
Mol. Wt.: 209.24
C, 63.14; H, 7.23; N, 6.69; O, 22.94

Strain:

*Pseudomonas fluorescens* A2-2 (wild type) (PM-S1-001)

Fermentation Conditions:

Seed medium YMP3 containing 1% glucose; 0.25% beef extract; 0.5% bacto-peptone; 0.25% NaCl; 0,8% CaCO3 was inoculated with 0.1% of a frozen vegetative stock of the microorganism, and incubated on a rotary shaker (250 rpm) at 27° C. After 30 h of incubation, the 2% (v/v) seed culture was transferred into 2000 ml Erlenmeyer flasks containing 250 ml of the M-16B production medium, composed of 15.2% mannitol; 3.5% Dried brewer's yeast; 1.4% $(NH_4)_2 SO_4$; 0.001%; $FeCl_3$; 2.6% $CO_3Ca$. The temperature of the incubation was 27° C. from the inoculation till 40 hours and then, 24° C. to final process (71 hours). The pH was not controlled. The agitation of the rotatory shaker was 220 rpm with 5 cm eccentricity.

Isolation:

After 71 hours of incubation, 2 Erlenmeyer flasks were pooled and the 500 ml of fermentation broth was clarified by 7.500 rpm centrifugation during 15 minutes. 50 grams of the resin XAD-16 (Amberlite) were added to the supernatant and mixed during 30 minutes at room temperature. Then, the resin was recovered from the clarified broth by filtration. The resin was washed twice with distilled water and extracted with 250 ml of isopropanol (2-PrOH). The alcohol extract was dried under high vacuum till obtention of 500 mg crude extract.

This crude was dissolved in methanol and purified by chromatographic column using Sephadex LH-20 and methanol as mobile phase. The P-14 compound was eluted and dried as a 15 mg yellowish solid. The purity was tested by analytical HPLC and $^1$H NMR.

P-14 was also isolated in a similar way from cultures of the sacJ$^-$ - mutant (PM-S1-005), using semipreparative HPLC as the last step in the purification process.

Biological Activities:

NO ACTIVE

Spectroscopic Data:

ESMS m/z 254 ($C_{11}H_{14}NO_3Na_2^+$), 232 ($C_{11}H_{15}NO_3Na^+$), 210 (M+H$^+$). $^1$H RMN (300 MHz, CD$_3$OD): 7.07 (d, J=8.1 Hz, H-9), 7.06 (s, H-5), 6.84 (d, J=8.1 Hz, H-8), 3.79 (s, H-11), 3.72 (dd, J=8.7, 3.9 Hz, H-2), 3.20 (dd, J=14.4, 3.9 Hz, H-3a), 2.91 (dd, J=14.4, 8.9 Hz, H-3b), 2.16 (s, H-10). $^{13}$C RMN (75 MHz, CD$_3$OD): 174.1 (C-1), 158.6 (C-7), 132.5 (C-5), 128.9 (C-9), 128.5 (C-4), 128.0 (C-6), 111.4 (C-8), 57.6 (C-2), 55.8 (C-11), 37.4 (C-3), 16.3 (C-10)

P-2

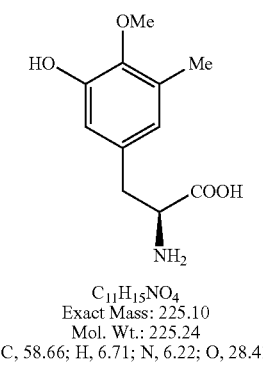

$C_{11}H_{15}NO_4$
Exact Mass: 225.10
Mol. Wt.: 225.24
C, 58.66; H, 6.71; N, 6.22; O, 28.41

Strain:

*Pseudomonas fluorescens* A2-2 (wild type) (PM-S1-001)

Fermentation Conditions:

The same process than P-14

Isolation:

Similar procedure as the P-14, except in the Sephadex chromatography, where the fractions containing P-2 have eluted later. A semi-preparative HPLC step (Symmetry Prep C-18 column, 7.8×150 mm, AcONH$_4$ 10 mM pH=3/CH$_3$CN 95:5 held for 5 min and then gradient from 5 to 6.8% of CH$_3$CN in 3 min) has been necessary to purify the P-2. Also this compound has been isolated from the fermentation broth of the *Pseudomonas putida* ATCC12633+pB5H83 (PM-17-004) as result of heterologous expression.

Biological Activities:

NO ACTIVE

Spectroscopic Data:

ESMS m/z 226 [M+H]$^+$; $^1$H RMN (CD$_3$OD, 300 MHz): 6.65 (d, J=1.8 Hz, H-5), 6.59 (d, J=1.8 Hz, H-9), 3.72 (s, H-11), 3.71 (dd, J=9.0, 4.2 Hz, H-2), 3.16 (dd, J=14.4, 4.2 Hz, H-3a), 2.83 (dd, J=14.4, 9.0 Hz, H-3b), 2.22 (s, H-10). $^{13}$C RMN (DMSO, 75 MHz): 170.88 (s, C-1), 150.025 (s, C-7), 144.56 (s, C-8), 132.28 (s, C-4), 130.36 (s, C-6), 121.73 (d, C-5), 115.55 (d, C-9), 59.06 (q, 7-OMe), 55.40 (d, C-2), 36.21 (t, C-3), 15.86 (q, 6-Me).

Characterization of Safracins like Compounds Obtained by Knock Out

COMPOUND P-22B

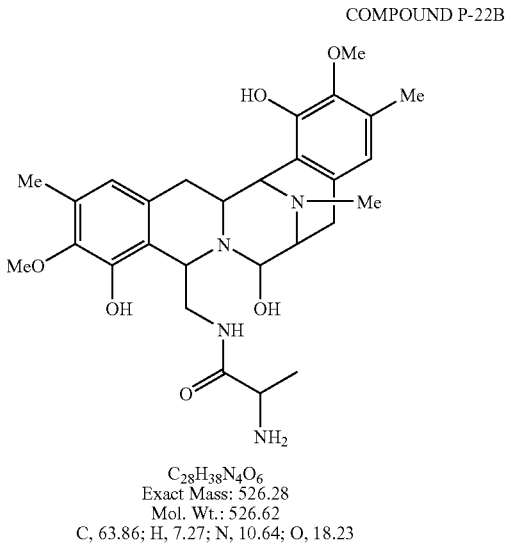

$C_{28}H_{38}N_4O_6$
Exact Mass: 526.28
Mol. Wt.: 526.62
C, 63.86; H, 7.27; N, 10.64; O, 18.23

Strain:

sac J$^-$ mutant from *P. fluorescens* A2-2 (PM-S1-005)

Fermentation conditions:

50 liters of the SAM-7 medium (50 l) composed of dextrose (3.2%), mannitol (9.6%), dry brewer's yeast (2%), ammonium sulphate (1.4%), potassium secondary phosphate (0.03%), potassium chloride (0.8%), Iron (III) chloride 6-hydrtate (0.001%), L-tyrosine (0.1%), calcium carbonate (0.8%), poly-(propylene glycol) 2000 (0.05%) and antifoam ASSAF 1000 (0.2%) was poured into a jar-fermentor (Bioengineering LP-351) with 75 l total capacity and, after sterilization, sterile antibiotics (amplicillin 0.05 g/l and kanamycin 0.05 g/l) were added. Then, it was inoculated with seed culture (2%) of the mutant strain PM-S1-005. The fermentation was carried out during 71 h. under aerated and agitated conditions (1.0 l/l/min and 500 rpm). The temperature was controlled from 27° C. (from the inoculation till 24 hours) to 25° C. (from 24 h to final process). The pH was controlled at pH 6.0 by automatic feeding of diluted sulphuric acid from 22 hours to final process.

Isolation

The whole broth was clarified (Sharples centrifuge). The pH of the clarified broth was adjusted to pH 9.0 by addition of NaOH 10% and extracted with 25 liters of ethyl acetate. After 20' mixing, the two phases were separated. The organic phase was frozen overnight and then, filtered for removing ice and evaporated to a greasy dark green extract (65.8 g). This extract was mixed with 500 ml hexane (250 ml two times) and filtered for removing hexane soluble impurities. The remaining solid, after drying, gave a 27.4 g of a dry green-beige extract.

This new extract was dissolved in methanol and purified by a Sephadex LH-20 chromatography (using methanol as mobile solvent) and the safracins-like compounds were eluted in the central fractions (Analyzed on TLC conditions: Silica normal phase, mobile phase: EtOAc:MeOH 5:3. Aprox. Rf valor: 0.3 for P-22B, 0.25 P-22A and 0.1 for P-19).

The pooled fractions, (7,6 g) containing the three safracin-like compound were purified by a Silica column using a mixture of EtOAc:MeOH from 50:1 to 0:1. and other chromatographic system (isocratic CHCl$_3$:MeOH:H$_2$O:AcOH 50:45:5:0.1). Compounds P22-A, P22-B and P19-B were purified by reversed-phase HPLC (SymmetryPrep C-18 column 150×7.8 mm, 4 mL/min, mobile phase: 5 min MeOH:H$_2$O (0.02% TFA) 5:95 and gradient from MeOH:H$_2$O (0.02% TFA) 5:95 to MeOH 100% in 30 min).

Biological Activities of Safracin P-22B

| Primary Screening | | Prostate | | Ovary | | Breast | Melanoma | NSCL |
|---|---|---|---|---|---|---|---|---|
| | | DU-145 | LN-caP | IGROV | IGROV-ET | SK-BR3 | SK-MEL-28 | A549 |
| Safra-cin P-22B | GI50 | 4.58E−06 | 3.08E−07 | 8.49E−07 | 3.02E−06 | 8.24E−07 | 5.20E−07 | 4.71E−06 |
| | TGI | 8.62E−06 | 6.08E−07 | 2.30E−06 | 7.04E−06 | 2.28E−06 | 9.99E−07 | 8.83E−06 |
| | LC50 | 1.62E−05 | 1.20E−06 | 1.21E−05 | 1.65E−05 | 8.85E−06 | 2.01E−06 | 1.66E−05 |

| Primary Screening | | Leukemia | Pancreas | Colon | | | Cervix | |
|---|---|---|---|---|---|---|---|---|
| | | K-562 | PANC1 | HT29 | LOVO | LOVO-DOX | HELA | HELA-APL |
| Safra-cin P-22B | GI50 | 1.13E−07 | 4.77E−06 | 1.01E−06 | 2.54E−06 | 6.95E−06 | 7.61E−07 | 4.65E−07 |
| | TGI | 4.67E−07 | 1.17E−05 | 2.75E−06 | 6.84E−06 | 1.90E−05 | 1.83E−06 | 9.32E−07 |
| | LC50 | 1.84E−06 | >1.90E−05 | 1.86E−05 | 1.84E−05 | >1.90E−05 | 7.42E−06 | 1.86E−06 |

Antimicrobial activity: On solid medium

*Bacillus subtilis.* 10 μg/disk (6 mm diameter): 10 mm inhibition zone

Spectroscopic Data:

HRFABMS m/z 509.275351 [M-H$_2$O+H]$^+$ (calcd for C$_{28}$H$_{37}$N$_4$O$_5$ 509.276396 Δ1.0 mmu); LRFABMS using m-NBA as matrix m/z (rel intensity) 509 [M-H$_2$O+H]$^+$ (5), 460 (2.7), 391 (3).

$^1$H NMR (CD$_3$OD, 500 MHz): 6.70 (s, H-15), 6.52 (s, H-5), 4.72 (bs, H-11), 4.66 (d, J=2.0 Hz, H-21), 4.62 (dd, J=8.4, 3.7 Hz, H-1), 3.98 (bd, J=7.6 Hz, H-13), 3.74 (s, 7-OMe), 3.71 (s, 17-OMe), 3.63 (m, overlapped signal, H-25), 3.62 (m, overlapped signal, H-3), 3.30 (m, H-22a), 3.29 (m, H-14a), 3.18 (d, J=18.6 Hz, H-14b), 2.90 (m, H-4a), 2.88 (m, H-22b), 2.76 (s, 12-NMe), 2.30 (s, 16-Me), 2.22 (m, H-4b), 1.16 (d, J=7.4 Hz, H-26);

$^{13}$C NMR (CD$_3$OD, 125 MHz): 170.75 (s, C-24), 149.24 (s, C-18), 147.54 (s, C-8), 145.95 (s, C-7), 145.82 (s, C17), 133.93 (s, C-16), 132.31 (s, C-9), 131.30 (s, C-6), 128.95 (s, C-20), 121.93 (d, C-15), 121.76 (d, C-5), 121.44 (s, C-10), 112.45 (s, C-19), 92.87 (d, C-21), 60.86 (q, 7-OMe), 60.76 (q, 17-OMe), 59.39 (d, C-11), 57.96 (d, C-13), 55.51 (d, C-1), 54.29 (d, C-3), 50.08 (d, C-25), 45.55 (t, C-22), 40.43 (q, 12-NMe), 32.56 (t, C-4), 25.84 (t, C-14), 17.20 (q, C-26), 16.00 (q, 16-Me), 15.81 (q, 6-Me).

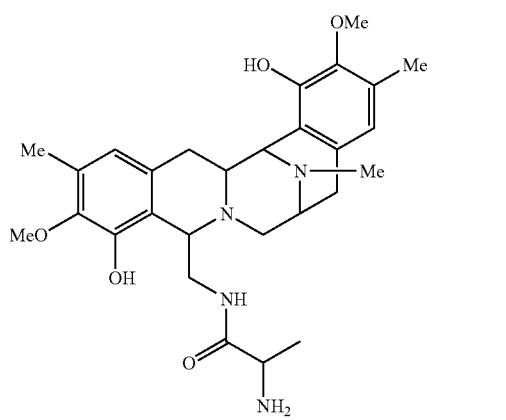

COMPOUND P-22A

Strain:

The same as for P-22B

Fermentation Conditions:

The same as for P-22B

Isolation:

The same as for P-22B

Biological Activities of Safracin P-22A

Antitumor Activities

| Primary Screening | | Cells Lines (Mol/L) | | | | | | |
|---|---|---|---|---|---|---|---|---|
| | | Prostate | | Ovary | | Breast | Melanoma | NSCL |
| | | DU-145 | LN-caP | IGROV | IGROV-ET | SK-BR3 | SK-MEL-28 | A549 |
| Safracin P-22A | GI50 | >1.96E−05 | 4.19E−06 | 7.74E−06 | 1.30E−05 | 1.27E−05 | 5.93E−06 | >1.96E−05 |
| | TGI | >1.96E−05 | 9.26E−06 | 1.96E−05 | >1.96E−05 | >1.96E−05 | 1.33E−05 | >1.96E−05 |
| | LC50 | >1.96E−05 | >1.96E−05 | >1.96E−05 | >1.96E−05 | >1.96E−05 | >1.96E−05 | >1.96E−05 |
| Primary Screening | | Leukemia | Pancreas | Colon | | | Cervix | |
| | | K-562 | PANC1 | HT29 | LOVO | LOVO-DOX | HELA | HELA-APL |
| Safracin P-22A | GI50 | 3.15E−06 | >1.96E−05 | 1.26E−05 | >1.96E−05 | >1.96E−05 | 8.75E−06 | 7.66E−06 |
| | TGI | 7.93E−06 | >1.96E−05 | >1.96E−05 | >1.96E−05 | >1.96E−05 | >1.96E−05 | 1.96E−05 |
| | LC50 | 1.96E−05 | >1.96E−05 | >1.96E−05 | >1.96E−05 | >1.96E−05 | >1.96E−05 | >1.96E−05 |

Antimicrobial activity: On solid medium

*Bacillus subtilis.* 10 μg/disk (6 mm diameter): NO ACTIVE

Spectroscopic data:

HRFABMS m/z 511.290345 [M+H]$^+$ (calcd for $C_{28}H_{39}N_4O_5$ 511.292046 A 1.7 mmu); LRFABMS using m-NBA as matrix m/z (rel intensity) 511 [M+H]$^+$ (61), 409 (25), 391 (4); $^1$H NMR (CD$_3$OD, 500 MHz): 6.68 (s, H-15), 6.44 (s, H-5), 3.71 (s, 7-OMe), 3.67 (s, 17-OMe), 2.72 (s, 12-NMe), 2.28 (s, 16-Me), 2.20 (s, 6-Me), 0.87 (d, J=7.1 Hz, H-26);

COMPOUND P-19B

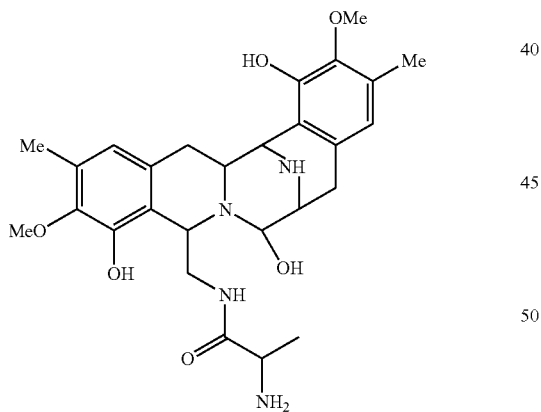

Strain:

The same as for P-22B

Fermentation Conditions:

The same as for P-22B

Isolation

The same as for P-22B

Biological Activities of Safracin P-19B

Antitumor Activities

| | Cells Lines (Mol/L) | | | | | | |
|---|---|---|---|---|---|---|---|
| Primary | Prostate | | Ovary | | Breast | Melanoma | NSCL |
| Screening | DU-145 | LN-caP | IGROV | IGROV-ET | SK-BR3 | SK-MEL-28 | A549 |
| Safracin GI50 | 1.70E−05 | 3.90E−06 | 5.42E−06 | 8.74E−06 | 7.08E−06 | 7.90E−06 | >1.95E−05 |
| P-19B TGI | >1.95E−05 | 8.06E−06 | 1.48E−05 | >1.95E−05 | 1.92E−05 | >1.95E−05 | >1.95E−05 |
| LC50 | >1.95E−05 | 1.67E−05 | >1.95E−05 | >1.95E−05 | >1.95E−05 | >1.95E−05 | >1.95E−05 |
| Primary | Leukemia | Pancreas | Colon | | | Cervix | |
| Screening | K-562 | PANC1 | HT29 | LOVO | LOVO-DOX | HELA | HELA-APL |
| Safracin GI50 | 2.38E−06 | 1.81E−05 | 1.55E−05 | >1.95E−05 | 1.44E−05 | 6.73E−06 | 4.80E−06 |
| P-19B TGI | 5.77E−06 | >1.95E−05 | >1.95E−05 | >1.95E−05 | >1.95E−05 | 1.61E−05 | 1.00E−05 |
| LC50 | 1.40E−05 | >1.95E−05 | >1.95E−05 | >1.95E−05 | >1.95E−05 | >1.95E−05 | 1.95E−05 |

Antimicrobial activity: On solid medium

*Bacillus subtilis.* 10 μg/disk (6 mm diameter): NO ACTIVE

Spectroscopic Data:

HRFABMS m/z 495.260410 [M-H$_2$O+H]$^+$ (calcd for C$_{27}$H$_{35}$N$_4$O$_5$ 495.260746 Δ0.3 mmu); LRFABMS using m-NBA as matrix m/z (rel intensity) 495 [M-H$_2$O+H]$^+$ (13), 460 (3), 391 (2); $^1$H NMR (CD$_3$OD, 500 MHz): 6.67 (s, H-15), 6.5 (s, H-5), 3.73 (s, 7-OMe), 3.71 (s, 17-OMe), 2.29 (s, 16-Me), 2.24 (s, 6-Me), 1.13 (d, J=7.1 Hz, H-26);

New Safracin Compounds Obtained by Knock Out

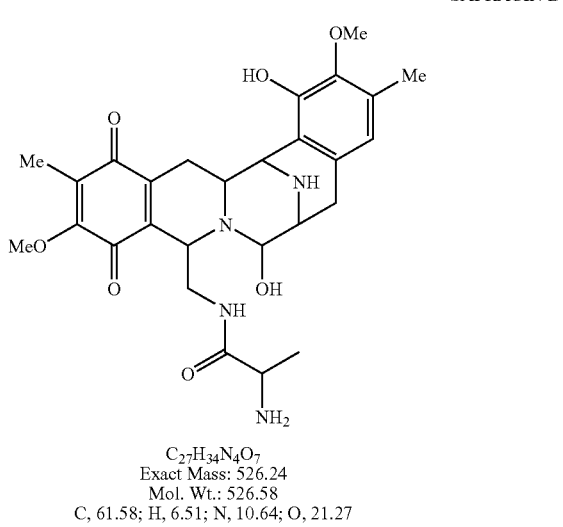

SAFRACIN D

C$_{27}$H$_{34}$N$_4$O$_7$
Exact Mass: 526.24
Mol. Wt.: 526.58
C, 61.58; H, 6.51; N, 10.64; O, 21.27

Strain:

sac I$^-$ with sacJ expression reconstitution from *P. fluorescens* A2-2 (PM-S1-007)

Fermentation Conditions:

50 liters of the SAM-7 medium (50 l) composed of dextrose (3.2%), mannitol (9.6%), dry brewer's yeast (2%), ammonium sulphate (1.4%), potassium secondary phosphate (0.03%), potassium chloride (0.8%), Iron (III) chloride 6-hydrtate (0.001%), L-tyrosine (0.1%), calcium carbonate (0.8%), poly-(propylene glycol) 2000 (0.05%) and antifoam ASSAF 1000 (0.2%) was poured into a jar-fermentor (Bioengineering LP-351) with 75 l total capacity and, after sterilization, sterile antibiotics (amplicillin 0.05 g/l and kanamycin 0.05 g/l) were added. Then, it was inoculated with seed culture (2%) of the mutant strain PM-S1-007. The fermentation was carried out during 89 h. under aerated and agitated conditions (1.0 l/l/min and 500 rpm). The temperature was controlled from 27° C. (from the inoculation till 24 hours) to 25° C. (from 24 h to final process). The pH was controlled at pH 6.0 by automatic feeding of diluted sulphuric acid from 27 hours to final process.

Isolation:

The cultured medium (45 l) thus obtained was, after removal of cells by centrifugation, adjusted to pH 9.5 with diluted sodium hydroxide, extracted with 25 liter of ethyl acetate twice. The mixture was carried out into an agitated-vessel at room temperature for 20 minutes. The two phases were separated by a liquid-liquid centrifuge. The organic phases were frozen at −20° C. and filtered for removing ice and evaporated until obtention of a 35 g. oil-dark-crude extract. After a 5 l. hexane triturating, the extract (12.6 g) was purified by a flash-chromatographic column (5.5 cm diameter, 20 cm length) on silica-normal phase, mobile phase: Ethyl acetate: MeOH: 1 L of each 1:0; 20:1; 10:1; 5:1 and 7:3. 250 ml-fractions were eluted and pooled depending of the TLC (Silica-Normal, EtOAc:MeOH 5:2, Safracin D Rf 0.2, safracin E 0.05). The fraction containing impure safracin D and E was evaporated under high vacuum (2.2 g). An additional purification step was necessary to separate D and E on similar conditions (EtOAc:MeOH from 1:0 to 5:1), from this, the fractions containing safracin D and E are separate and evaporated and further purification by Sephadex LH-20 column chromatography eluted with methanol.

The safracins D and E obtained were independent precipitated from CH$_2$Cl$_2$ (80 ml) and Hexane (1500 ml) as a green/yellowish-dried solid (800 mg safracin D) and (250 mg safracin E).

Biological Activities Safracin D

Antitumor Screening:

| | | Cells Lines (Mol/L) | | | | | | |
|---|---|---|---|---|---|---|---|---|
| Primary | | Prostate | | Ovary | | Breast | Melanoma | NSCL | Leukemia |
| Screening | | DU-145 | LN-caP | IGROV | IGROV-ET | SK-BR3 | SK-MEL-28 | A549 | K-562 |
| Safracin D | GI50 | 5.22E−06 | 1.54E−06 | 2.68E−06 | 1.33E−06 | 4.71E−06 | 3.51E−06 | 6.04E−06 | 6.04E−07 |
| | TGI | 9.99E−06 | 4.12E−06 | 6.02E−06 | 3.34E−06 | 7.82E−06 | 6.21E−06 | 1.07E−05 | 1.16E−06 |
| | LC50 | 1.90E−05 | 9.78E−06 | 1.35E−05 | 9.15E−06 | 1.30E−05 | 1.10E−05 | 1.88E−05 | 3.78E−06 |

| | | Primary | Pancreas | Colon | | | Cervix | |
|---|---|---|---|---|---|---|---|---|
| | | Screening | PANC1 | HT29 | LOVO | LOVO-DOX | HELA | HELA-APL |
| | Safracin D | GI50 | 4.77E−06 | 4.33E−06 | 6.99E−06 | 4.75E−06 | 3.76E−06 | 2.28E−06 |
| | | TGI | 1.10E−05 | 1.79E−05 | 1.82E−05 | 8.85E−06 | 6.68E−06 | 5.24E−06 |
| | | LC50 | >1.90E−05 | >1.90E−05 | >1.90E−05 | 1.65E−05 | 1.19E−05 | 1.21E−05 |

| | Secondary Evaluation (Mol/L) | | | | |
|---|---|---|---|---|---|
| | Macromolecules Synthesis | | | Apoptosis | DNA Binding |
| Secondary Screening | PROTEIN | DNA | RNA | NUCLEOSOMES | GEL |
| Safracin D  IC50 | 1.90E−05 | 1.52E−05 | 3.80E−06 | 2.85E−06 | 6.65E−06 |

Antimicrobial activity: On solid medium

*Bacillus* subtils. 10 μg/disk (6 mm diameter): Inhibition zone: 15 mm diameter

Spectroscopic Data

ESMS: m/z 509 $[M-H_2O+H]^+$; $^1H$ NMR (CDCl$_3$, 300 MHz): 6.50 (s, C-15), 4.02 (s, OMe), 3.73 (s, OMe), 2.22 (s, Me), 1.85 (s, Me), 0.80 (d, J=7.2 Hz); $^{13}C$ NMR (CDCl$_3$, 75 MHz): 186.51, 181.15, 175.83, 156.59, 145.09, 142.59, 140.78, 137.84, 131.20, 129.01, 126.88, 121.57 (2×C), 82.59, 60.92, 60.69, 53.12, 21.40, 50.68, 50.22, 48.68, 40.57, 29.60, 25.01, 21.46, 15.64, 8.44.

SAFRACIN E

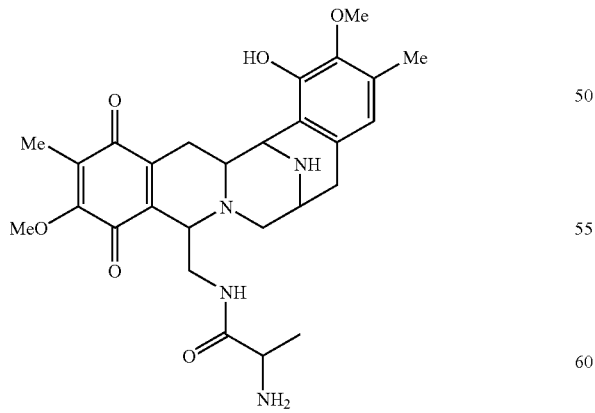

$C_{27}H_{34}N_4O_6$
Exact Mass: 510.25
Mol. Wt.: 510.58
C, 63.51; H, 6.71; N, 10.97; O, 18.80

Strain:

The same than safracin D

Fermentation Conditions:

The same batch as safracin D

Isolation:

See safracin D conditions

Biological Activities Safracin E

Antitumor screening:

and PFSC83 (5p GGTCTAGATAACAGCCAACAAA-CATA-3 SEQ ID NO: 23) were used to amplify sacE to sacH genes; and oligonucleotides 5HPTI-XB (5'-CATCTAGAC-CGGACTGATATTCG-3' SEQ ID NO: 24) and PFSC83 (5'-GGTCTAGATAACAGCCAACAAACATA-3' SEQ ID NO: 25) were used to amplify sacD to sacH genes. The PCR fragments digested with XbaI were cloned into the XbaI restriction site of the pBBR1-MCS2 plasmid (Kovach et al, Gene 1994 2 166p 175-176). The two plasmids, p137983 and pB5H83, were introduce separately into three heterologous bacteria P. fluorescens(CECT 378), P. putida(ATCC 12633)

| | Cells Lines (Mol/L) | | | | | | | |
|---|---|---|---|---|---|---|---|---|
| Primary | | Prostate | | Ovary | | Breast | Melanoma | NSCL | Leukemia |
| Screening | | DU-145 | LN-caP | IGROV | IGROV-ET | SK-BR3 | SK-MEL-28 | A549 | K-562 |
| Safracin E | GI50 | 8.34E−06 | 3.86E−06 | 4.50E−06 | 4.54E−06 | 5.05E−06 | 3.94E−06 | 1.96E−05 | 4.25E−06 |
| | TGI | 1.96E−05 | 7.70E−06 | 8.85E−06 | 8.25E−06 | 9.24E−06 | 6.93E−06 | >1.96E−05 | 8.21E−06 |
| | LC50 | >1.96E−05 | 1.54E−05 | 1.74E−05 | 1.49E−05 | 1.70E−05 | 1.22E−05 | >1.96E−05 | 1.59E−05 |
| | Primary | | Pancreas | | Colon | | | Cervix | |
| | Screening | | PANC1 | HT29 | LOVO | LOVO-DOX | | HELA | HELA-AP |
| | Safracin E | GI50 | 6.05E−06 | 7.89E−06 | 7.15E−06 | 5.07E−06 | | 4.15E−06 | 4.03E−06 |
| | | TGI | 1.47E−05 | 1.96E−05 | >1.96E−05 | 9.44E−06 | | 7.29E−06 | 7.25E−06 |
| | | LC50 | >1.96E−05 | >1.96E−05 | >1.96E−05 | 1.75E−05 | | 1.28E−05 | 1.30E−05 |
| | Secondary Evaluation (Mol/L) | | | | | | | |
| | | Macromolecules Synthesis | | | Apoptosis | | DNA Binding | |
| Secondary Screening | | PROTEIN | DNA | RNA | NUCLEOSOMES | | GEL | |
| Safracin E | IC50 | | | 1.57E−05 | >1.96E−05 | | | |

Antimicrobial activity: On solid medium

Bacillus subtilis. 10 µg/disk (6 mm diameter): 9.5 mm inhibition zone

Spectroscopic Data

ESMS: m/z 511 [M+H]$^+$; $^1$H NMR (CDCl$_3$, 300 MHz): 6.51 (s, C-15), 4.04 (s, OMe), 3.75 (s, OMe), 2.23 (s, Me), 1.89 (s, Me), 0.84 (d, J=6.6 Hz); $^{13}$C NMR (CDCl$_3$, 75 MHz): 186.32, 181.28, 175.83, 156.43, 145.27, 142.75, 141.05, 137.00, 132.63, 128.67, 126.64, 122.00, 120.69, 60.69, 60.21, 59.12, 58.04, 57.89, 50.12, 49.20, 46.72, 39.88, 32.22, 25.33, 21.29, 15.44, 8.23.

Example 5

Cross-Feeding Experiments

Heterologous Expression of Safracin Biosynthetic Precursors Genes for P2 and P14 Production In the attempt to shed light on the mechanism of the P2 and P14 biosynthesis we have cloned and expressed the downstream NRPS genes to determine their biochemical activity.

To overproduce P14, sacEFGH genes were cloned (pB7983) (FIG. 4). To overproduce P2 in a heterologous system, sacD to sacH genes were cloned (pB51183)(FIG. 4). For this purpose we PCR amplified fragments harboring the genes of interest using oligonucleotides that contain a XbaI restriction site at the 5' end. Oligonucleotides PFSC79 (5' CGTCTAGACACCGGCTFFCATGG-3' SEQ ID NO: 22)

and P. stutzeri(ATCC 17588) by conjugation (see table II). When culture broth of the fermentation of the transconjugant strains was checked by HPLC analysis, big amounts of P14 compound was visualized in the three strains containing pB7983 plasmid, whereas big amounts of P2 and some P14 product were observed when pB5H83 plasmid was expressed in the heterologa bacteria.

Cross-Feeding

As it was shown in Example 4, the sacF$^-$ (PM-S1-008) and sacG- (PM-S1-009) mutants were not able to produce neither safracins nor P2 and P14 compounds. The addition of chemically synthesized P2 to these mutants during their fermentation yields safracin production.

Moreover, the co-cultivation of an heterologous strain of P. stutzeri (ATCC 17588) harboring plasmid pB5H83 (PM-18-004), which expression produces P2 and P14, with either one of the two mutants sacF$^-$ and sacG- resulted in safracin production. The co-cultivation of an heterologous strain P. stutzeri (ATCC 17588) harboring plasmid pB7983 (PM-18-005), which expression produces only P14, with either one of the two P. fluorescens A2-2 mutants mentioned before resulted in no safracin production at all. These results suggest that P14 is transformed into P2, a molecule that can easily be transported in and out through the Pseudomonas sp. cell wall and which presence it is absolutely necessary for the biosynthesis of safracin.

Example 6

Biological Production of New "Unnatural" Molecules

The addition of 2 g/L of a specific modified P2 derivative precursor, P3, a 3-hydroxy-5-methyl-O-ethyltyrosine, to the sacF mutant (PM-S1-008) fermentation yielded two "unnatural" safracins that incorporated the modified precursor P3 in its structure, Safracin A(OEt) and Safracin B(OEt).

SAFRACIN B-Etoxi (Safracin B (OEt))

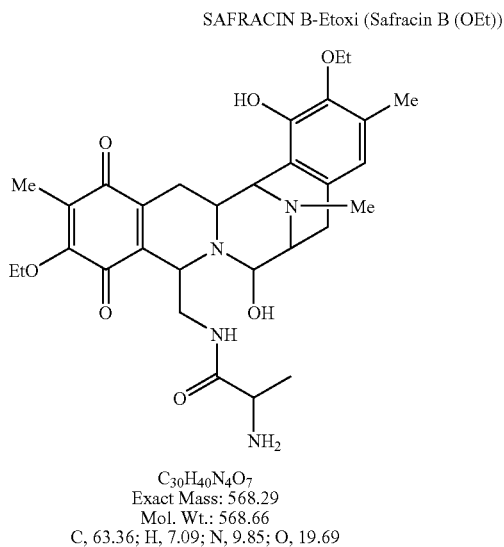

$C_{30}H_{40}N_4O_7$
Exact Mass: 568.29
Mol. Wt.: 568.66
C, 63.36; H, 7.09; N, 9.85; O, 19.69

Strain saf F⁻ mutant from *P. fluorescens* A2-2 (PM-S1-008)

Fermentation Conditions:

Seed medium containing 1% glucose; 0.25% beef extract; 0.5% bacto-peptone; 0.25% NaCl; 0.8% CaCO3 was inoculated with 0.1% of a frozen vegetative stock of the microorganism, and incubated on a rotary shaker (250 rpm) at 27° C. After 30 h of incubation, the 2% (v/v) seed culture of the mutant PM-S1-008 was transferred into 2000 ml Erlenmeyer flasks containing 250 ml of the M-16 B production medium, composed of 15.2% mannitol; 3.5% Dried brewer's yeast; 1.4% $(NH_4)_2$ 0.001%; $FeCl_3$; 2.6% $CO_3Ca$ and 0.2% P3 (3-hydroxy-5-methyl-O-methyltyrosine) The temperature of the incubation was 27° C. from the inoculation till 40 hours and then, 24° C. to final process (71 hours). The pH was not controlled. The agitation of the rotatory shaker was 220 rpm with 5 cm eccentricity.

Isolation

4×2000/250 ml Erlenmeyer flasks were joined together (970 ml), centrifuged (12.000 rpm, 4° C., 10', J2-21 Centrifuge BECKMAN) to remove cells. The clarified broth (765 ml) was adjusted to pH 9.0 by NaOH 10%. Then, the alkali-clarified broth was extracted with 1:1 (v/v) EtOAc (×2). The organic phase was evaporated under high vacuum and a greasy-dark extract was obtained (302 mg).

This extract was washed by an hexane trituration for removing impurities and the solids were purified by a chromatography column using Silica normal-phase and a mixture of Ethyl Acetate: Methanol (from 12:1 to 1:1). The fractions were analyzed under UV on TLC (Silica 60, mobile phase EtOAc:MeOH 5:4. $R_f$ 0.3 (Safracin B-OEt and 0.15 Safracin A-OEt). From this, safracins B OEt (25 mg) and safracin A OEt (20 mg) were obtained.

Biological Activities of Safracin B (OEt)

Antitumor Activities

| | | Cells Lines (Mol/L) | | | | | | | |
|---|---|---|---|---|---|---|---|---|---|
| Primary | | Prostate | | Ovary | | Breast | Melanoma | NSCL | Leukemia |
| Screening | | DU-145 | LN-caP | IGROV | IGROV-ET | SK-BR3 | SK-MEL-28 | A549 | K-562 |
| Safracin B (OEt) | GI50 | 4.01E−07 | 4.84E−08 | 4.06E−08 | 6.82E−07 | 4.82E−08 | 1.69E−07 | 5.01E−07 | 3.97E−08 |
| | TGI | 1.01E−06 | >1.76E−05 | 9.97E−08 | 1.19E−06 | 1.16E−07 | 4.40E−07 | 1.16E−06 | 1.08E−07 |
| | LC50 | 1.60E−05 | 8.28E−07 | 4.27E−06 | 6.37E−06 | 1.02E−06 | 1.13E−06 | 5.66E−06 | 3.69E−06 |

| | | Primary | Pancreas | Colon | | Cervix | |
|---|---|---|---|---|---|---|---|
| | | Screening | PANC1 | HT29 | LOVO | LOVO-DOX | HELA | HELA-APL |
| Safracin B (OEt) | GI50 | 6.49E−07 | 2.44E−07 | 4.43E−07 | 2.09E−06 | 8.92E−08 | 7.70E−08 |
| | TGI | 2.06E−06 | 1.39E−06 | 1.09E−06 | 9.88E−06 | 3.15E−07 | 2.74E−07 |
| | LC50 | 1.35E−05 | >1.76E−05 | >1.76E−05 | >1.76E−05 | 1.35E−06 | 9.76E−07 |

| | | Secondary Evaluation (Mol/L) | | | | |
|---|---|---|---|---|---|---|
| Secondary | | Macromolecules Synthesis | | | Apoptosis | DNA Binding |
| Screening | | PROTEIN | DNA | RNA | NUCLEOSOMES | GEL |
| Safracin B (OEt) | IC50 | >1.76E−05 | 1.76E−06 | 1.76E−07 | 5.28E−08 | 1.76E−05 |

Antimicrobial activity: On solid medium

*Bacillus subtilis*. 10 µg/disk (6 mm diameter): 17,5 mm inhibition zone

Spectroscopic Data:

ESMS: m/z 551 [M-$H_2O$+H]⁺; ¹H NMR (CDCl₃, 300 MHz): 6.48 (s, H-15), 2.31 (s, 16-Me), 2.22 (s, 12-NMe), 1.88

(s, 6-Me), 1.43 (t, J=6.9 Hz, Me-Etoxy), 1.35 (t, J=6.9 Hz, Me-Etoxy), 0.81 (d, J=7.2 Hz, H-26)

Strain:

The same as for Safracin B (OEt)

Fermentation conditions:

The same as for Safracin B (OEt)

Isolation:

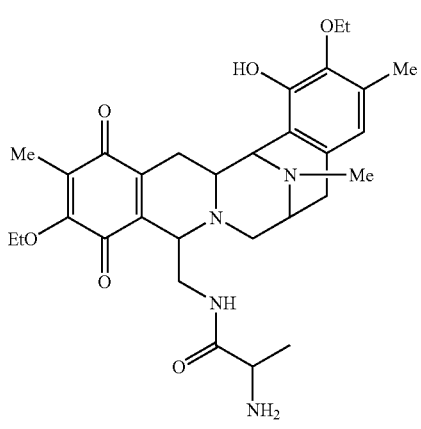

SAFRACIN A-Etoxi (Safracin A (OEt))

$C_{30}H_{40}N_4O_6$
Exact Mass: 552.29
Mol. Wt.: 552.66
C, 65.20; H, 7.30; N, 10.14; O, 17.37

4×2000/250 ml Erlenmeyer flasks were joined together (970 ml), centrifuged (12.000 rpm, 4° C., 10', J2-21 Centrifuge BECKMAN) to remove cells. The clarified broth (765 ml) was adjusted to pH 9,0 by NaOH 10%. Then, the alkali-clarified broth was extracted with 1:1 (v/v) EtOAc (×2). The organic phase was evaporated under high vacuum and a greasy-dark extract was obtained (302 mg).

This extract was washed by an hexane trituration for removing impurities and the solids were purified by a chromatography column using Silica normal-phase and a mixture of Ethyl Acetate: Methanol (from 12:1 to 1:1). The fractions were analysed under UV on TLC (Silica 60, mobile phase EtOAc:MeOH 5:4. Rf 0.3 Safracin B-OEt and 0.15 Safracin A-OEt). From this, safracins B OEt (25 mg) and safracin A OEt (20 mg) were obtained.

Biological Activities of Safracin A (OEt):

Antitumor Activities

| | | Cells Lines (Mol/L) | | | | | | |
|---|---|---|---|---|---|---|---|---|
| Primary | | Prostate | | Ovary | | Breast | Melanoma | NSCL |
| Screening | | DU-145 | LN-caP | IGROV | IGROV-ET | SK-BR3 | SK-MEL-28 | A549 |
| Safracin A (OEt) | GI50 | 2.64E–06 | 3.78E–07 | 4.92E–07 | 2.01E–06 | 5.55E–07 | 7.96E–07 | 4.00E–06 |
| | TGI | 5.39E–06 | 7.42E–07 | 9.28E–07 | 5.10E–06 | 1.16E–06 | 1.90E–06 | 7.17E–06 |
| | LC50 | 1.10E–05 | 1.45E–06 | 1.76E–06 | 1.30E–05 | 5.57E–06 | 5.77E–06 | 1.28E–05 |
| Primary | | Leukemia | Pancreas | Colon | | | Cervix | |
| Screening | | K-562 | PANC1 | HT29 | LOVO | LOVO-DOX | HELA | HELA-AFL |
| Safracin A (OEt) | GI50 | 3.11E–07 | 3.06E–06 | 1.97E–06 | 2.03E–06 | 5.72E–06 | 1.02E–06 | 7.64E–07 |
| | TGI | 6.86E–07 | 5.83E–06 | 4.41E–06 | 4.41E–06 | 9.84E–06 | 2.91E–06 | 2.32E–06 |
| | LC50 | 1.51E–06 | 1.11E–05 | 9.88E–06 | 9.61E–06 | 1.69E–05 | 7.85E–06 | 6.69E–06 |
| | | Secondary Evaluation (Mol/L) | | | | | | |
| | | Macromolecules Synthesis | | | Apoptosis | | DNA Binding | |
| Secondary Screening | | PROTEIN | DNA | RNA | NUCLEOSOMES | | GEL | |
| Safracin A (OEt) | IC50 | | | 6.33E–06 | 1.81E–06 | | | |

Antimicrobial activity: On solid medium

*Bacillus subtilis*. 10 µg/disk (6 mm diameter): 10 mm inhibition zone

Spectroscopic Data:

ESMS: m/z 553 [M+H]$^+$; $^1$H NMR (CDCl$_3$, 300 MHz): 6.48 (s, H-15), 2.33 (s, 16-Me), 2.21 (s, 12-NMe), 1.88 (s, 6-Me), 1.42 (t, J=6.9 Hz, Me-Etoxy), 1.34 (t, J=6.9 Hz, Me-Etoxy), 0.8 (d, J=6.9 Hz, H-26)

Example 7

Enzymatic Transformation of Safracin B into Safracin A

In order to assay the enzymatic activity of conversion of safracin B into safracin A, a 120 hours fermentation cultures (see conditions in Example.2.Biological assay (biotest) for safracin production) of different strains were collected and centrifuged (9.000 rpm×20 min.). The strains assayed were *P. fluorescens* A2-2, as wild type strain, and *P. fluorescens* CECT378+pBHPT3 (PM-19-006), as heterologous expression host. Supernatant were discarded and cells were washed (NaCl 0.9%) twice and resuspended in 60 ml phosphate buffer 100 mM pH 7.2. 20 ml from the cell suspension was distributed into three Erlenmeyer flask:

A. Cell suspension+Safracin B (400 mg/L)
B. Cell suspension heated at 100° C. during 10 min.+Safracin B (400 mg/L) (negative control)
C. Cell suspension without Safracin B (negative control)

The biochemical reaction was incubated at 27° C. at 220 rpm and samples were taken every 10 min. Transformation of safracin B into safracin A was followed by HPLC. The results clearly demonstrated that the gene cloned in pBHPT3, sacH, codes for a protein responsible for the transformation of safracin B into safracin A.

Based on this results we did an assay to find out if this same enzyme was able to recognize a different substrate such as ecteinascidin 743 (ET-743) and transform this compound into Et-745 (with the C-21 hydroxyl missing). The experiment above was repeated to obtain Erlenmeyer flasks containing:

A. Cell suspension+ET-743 (567 mg/L aprox.)
B. Cell suspension heated at 100° C. during 10 min.+ET-743(567 mg/L) (negative control)
C. Cell suspension without ET-743 (negative control)

The biochemical reaction was incubated at 27° C. at 220 rpm and samples were taken at o, 10 min, 1 h, 2 h, 3 h, 4 h, 20 h, 40 h, 44 h, 48 h. Transformation of ET-743 into ET-745 was followed by HPLC. The results clearly demonstrated that the gene cloned in pBHPT3, sacH, codes for a protein responsible for the transformation of Et-743 into Et-745. This demonstrates that this enzymes recognizes ecteinascidin as substrate and that it can be used in the biotransformation of a broad range of structures.

The invention claimed is:

1. An isolated nucleic acid sequence comprising:
   a) the nucleic acid sequence of SEQ ID NO:1;
   b) the sacABCDEFGH operon of SEQ ID NO:1;
   c) the sacA, sacB, sacC, sacD, sacE, sacF, sacG, and sacH genes of SEQ ID NO:1;
   d) a nucleic acid sequence encoding the amino acid sequence SEQ ID NO: 2, 3, 4, 5, 6, 7, 8 or 9; or
   e) a nucleic acid sequence that is the full complement to the sequence in a), b), c), or d).

2. The nucleic acid sequence of claim 1, wherein the nucleic acid sequence comprises:
   a) the nucleic acid sequence of SEQ ID NO:1; or
   b) the nucleic acid sequence which is the full complement to the sequence in a).

3. A vector comprising the nucleic acid sequence of claim 1.

4. The vector of claim 3 which is an expression vector.

5. The vector of claim 3 which is a cosmid.

6. A composition comprising at least one nucleic acid sequence of claim 1.

7. The nucleic acid of claim 1 wherein the nucleic acid sequence comprises the sacABCDEFGH operon.

8. An isolated nucleic acid sequence comprising both the sacABCDEFGH operon and the sacIJ operon of SEQ ID NO:1.

9. The nucleic acid of claim 8 wherein the sacI gene of the sacIJ operon is disrupted.

10. The nucleic acid of claim 8 wherein the sacJ gene of the sacIJ operon is disrupted.

11. The nucleic acid of claim 8 wherein the sacI gene of the sacIJ operon is disrupted and the expression of the sacJ gene has been reconstituted.

12. The nucleic acid of claim 8 wherein the sacF gene and/or the sacG gene of the sacABCDEFGH operon has been disrupted.

13. The nucleic acid sequence of claim 1 wherein the nucleic acid sequence comprises SEQ ID NO: 1.

14. An isolated nucleic acid sequence comprising:
   a) the nucleic acid sequence of SEQ ID NO:1;
   b) the sacABCDEFGH operon of SEQ ID NO:1; or
   c) a nucleic acid sequence that is the full complement to the sequence in a) or b).

* * * * *